US012122741B2

(12) United States Patent
Belser et al.

(10) Patent No.: US 12,122,741 B2
(45) Date of Patent: Oct. 22, 2024

(54) THERAPEUTIC PHENETHYLAMINE COMPOSITIONS AND METHODS OF USE

(71) Applicant: CYBIN IRL LIMITED, Dublin (IE)

(72) Inventors: Alex Belser, Brooklyn, NY (US); Clinton E. Canal, Atlanta, GA (US); Brett J. Greene, Fitchburg, MA (US); Joshua A. Hartsel, Lake Forest, CA (US); Alex Nivorozhkin, West Roxbury, MA (US); Michael Palfreyman, Waltham, MA (US)

(73) Assignee: Cybin IRL Limited, Dublin (IE)

( * ) Notice: Subject to any disclaimer, the term of this patent is extended or adjusted under 35 U.S.C. 154(b) by 0 days.

(21) Appl. No.: 18/041,731

(22) PCT Filed: Aug. 18, 2021

(86) PCT No.: PCT/EP2021/072896
§ 371 (c)(1),
(2) Date: Feb. 15, 2023

(87) PCT Pub. No.: WO2022/038170
PCT Pub. Date: Feb. 24, 2022

(65) Prior Publication Data
US 2023/0312464 A1  Oct. 5, 2023

Related U.S. Application Data

(60) Provisional application No. 63/131,974, filed on Dec. 30, 2020, provisional application No. 63/067,303, filed on Aug. 18, 2020.

(51) Int. Cl.
C07C 323/32 (2006.01)
C07C 217/60 (2006.01)
C07C 323/20 (2006.01)

(52) U.S. Cl.
CPC .......... *C07C 323/32* (2013.01); *C07C 217/60* (2013.01); *C07C 323/20* (2013.01); *C07B 2200/05* (2013.01)

(58) Field of Classification Search
CPC .................. C07C 323/32; C07B 2200/05
See application file for complete search history.

(56) References Cited

U.S. PATENT DOCUMENTS

| 11,246,860 B2 | 2/2022 | Kristensen et al. |
| 11,633,390 B2 | 4/2023 | Kristensen et al. |
| 11,642,336 B2 | 5/2023 | Kristensen et al. |
| 2008/0241255 A1 | 10/2008 | Rose et al. |
| 2022/0267252 A1 | 8/2022 | Traschel et al. |
| 2022/0323378 A1 | 10/2022 | Joseph |

FOREIGN PATENT DOCUMENTS

| CN | 112430187 A | 3/2021 |
| WO | WO 2006/079999 A2 | 8/2006 |
| WO | WO 2008/016677 A2 | 2/2008 |
| WO | WO 2008/016677 A3 | 2/2008 |
| WO | WO 2008/121610 A1 | 10/2008 |
| WO | WO 2020/169850 A1 | 8/2020 |
| WO | WO 2020/181194 A1 | 9/2020 |
| WO | WO 2020/212951 A1 | 10/2020 |
| WO | WO 2020/245133 A1 | 12/2020 |
| WO | WO 2021/003467 A1 | 1/2021 |
| WO | WO 2021/116503 A2 | 6/2021 |
| WO | WO 2021/116503 A8 | 6/2021 |
| WO | WO 2021/234608 A1 | 11/2021 |
| WO | WO 2022/038170 A1 | 2/2022 |
| WO | WO 2022/038171 A1 | 2/2022 |
| WO | WO 2022/069690 A2 | 4/2022 |
| WO | WO 2022/069690 A3 | 4/2022 |
| WO | WO 2022/182602 A2 | 9/2022 |
| WO | WO 2022/221942 A1 | 10/2022 |
| WO | WO 2022/225884 A1 | 10/2022 |
| WO | WO 2022/261240 A2 | 12/2022 |
| WO | WO 2022/271982 A1 | 12/2022 |
| WO | WO 2022/261240 A3 | 1/2023 |
| WO | WO 2023/283386 A2 | 1/2023 |
| WO | WO 2023/288013 A2 | 1/2023 |
| WO | WO 2023/023351 A1 | 2/2023 |
| WO | WO 2023/283386 A3 | 2/2023 |
| WO | WO 2023/036473 A1 | 3/2023 |
| WO | WO 2023/049480 A1 | 3/2023 |
| WO | WO 2023/156450 A1 | 8/2023 |
| WO | WO 2023/156453 A1 | 8/2023 |

(Continued)

OTHER PUBLICATIONS

Li et al. (Neuropsychopharmacology (2011) 36, 940-949).*
Stella (J. Pharmaceutical Sciences, 2010, 99(12), pp. 4755-4765).*
Shah et al. (Journal of Enzyme Inhibition and Medicinal Chemistry, 2007, 22(5), pp. 605-621).*
Patani et al. (Chem. Rev., 1996, 96, pp. 3147-3176).*
Yale, H. (Journal of Medicinal and Pharmaceutical Chemistry, 1959, 1(2), pp. 121-133).*
Blaazer et al. (ChemMedChem, 2008, 3, pp. 1299-1309).*
Von D. Trachsel (Helvetica Chimica Acta, 2003, 86, pp. 2610-2619).*
Google translated, von D. Trachsel (Helvetica Chimica Acta, 2003, 86, pp. 2610-2619).*
AZ04784681(ON) Database accession No. 2022733918, "2-(5-methoxy-2H-1,3-benzoxathiol-6-yl)ethan-1-amine", STN01 Mar. 2019, Chemcats.

(Continued)

Primary Examiner — Susanna Moore
(74) Attorney, Agent, or Firm — Lathrop GPM LLP; Lisa Hillman

(57) ABSTRACT

There are disclosed deuterated 2C—X phenethylamine compounds, the use of such compounds in the treatment of diseases associated with a serotonin 5-HT$_2$ receptor, pharmaceutical compositions such as tablet compositions and kits containing the compounds, methods of delivering the compounds in a mist via inhalation, and methods of treating diseases or disorders associated with a serotonin 5-HT$_2$ receptor, such as central nervous system (CNS) disorders or psychological disorders with the compounds of the invention.

13 Claims, 16 Drawing Sheets

(56) References Cited

FOREIGN PATENT DOCUMENTS

| WO | WO 2023/186867 A1 | 10/2023 |
|---|---|---|
| WO | WO 2023/186963 A1 | 10/2023 |
| WO | WO 2024/089226 A1 | 5/2024 |

OTHER PUBLICATIONS

AZ04786463 Database accession No. 0915409267, "[2-(5-methoxy)-2H-1,3-benzoxythiol-6-yl)ethyl](methyl)amine", STN01 Mar. 2019, Chemcats.
AZ05479357(ON)Database accession No. 1334856705, Azepine H C, "2-(5-methoxy-2H-1,3-benzoxathiol-6-yl)propan-1-amine", STN01 Mar. 2019 (Mar. 1, 2019), Chemcats.
AZ05508757 Database accession No. 0103296540, Azepine O M, "1-(5-methoxy-2H-1,3-benzoxathiol-6-yl)-2-methylpropan-2-amine", STN01 Mar. 2019, Chemcats.
AZ06532047 (ON) Database accession No. 0797974793, Alex Kizi, "2-amino-3-(5-methoxy-2H-1,3-benzoxathiol-6-yl)propanenitrile", STN01 Mar. 2019, Chemcats.
Beaton et al., "A Comparison of the Behavioral Effects of Proteo- and Deutero-N, N-Dimethyltryptamine", Pharmacology Biochemistry & Behavior, 1982, 16: 811-814.
Bijlsma et al., "Fragmentation pathways of drugs of abuse and their metabolites based on QTOF MS/MS and MSE accurate-mass spectra", Journal Of Mass Spectrometry, Sep. 1, 2011, 46(9): 865-875.
Bjornstad et al., "Development and Clinical Application of an LC-MS-MS Method for Mescaline in Urine", Journal of Analytical Toxicology, Apr. 2008, 32(3): 227-231.
Borchardt et al., "General methods for the preparation of [alpha] and/OR [beta] deuterium labelled 6-hydroxydopamine derivatives", Journal of Labelled Compounds and Radiopharmaceuticals, vol. 19, No. 3, Mar. 1, 1982, pp. 433-445.
Cheze et al., "Simultaneous analysis of six amphetamines and analogues in hair, blood and urine by LC-ESI-MS/MS", Forensic Science International, Jul. 26, 2007, 170(2-3): 100-104.
Database Caplus [online] Dec. 29, 2009 (Dec. 29, 2009), Chen: "A series of deuterium labelled phenylalkylamines as drug testing standards", XP055867027, Database accession No. 2010:371880.
Database Registry [online] Oct. 22, 2009 (Oct. 22, 2009), Chemcats N: "2-[4-methyl-2,5-bis(trideuteriomethoxy)phenyl]ethanamine", XP055866937, Database accession No. 1189574-92-2.
Database Registry [online] Chemical Abstracts Service, Columbus, Ohio, US; Oct. 22, 2009 (Oct. 22, 2009), "2,5-(Dimethoxy-d6)-4-methylphenethylamine Hydrochloride", XP055866918, accession No. 1725444279 (Chemcats) Database accession No. 1189467-51-3.
Database Registry [online] Chemical Abstracts Service, Columbus, Ohio, US; Oct. 25, 2009 (Oct. 25, 2009), "2C-B-d6 Hydrochloride", XP055866926, accession No. 2145931586 (Chemcats) Database accession No. 1189978-45-7.
Database Registry [online] Chemical Abstracts Service, Columbus, Ohio, US; Oct. 26, 2007 (Oct. 26, 2007), "Benzeneethanamine, 4-chloro-2,5-di(methoxy-d3)-", XP055866907, accession No. 1144584103 (Chemcats) Database accession No. 951442-78-7.
Database Registry [online] Chemical Abstracts Service, Columbus, Ohio, US; Apr. 5, 2010 (Apr. 5, 2010), "2,5-(Dimethoxy-d6)-4-iodophenethylamine Hydrochloride", XP055866911, accession No. 1819317403 (Chemcats) Database accession No. 1216685-82-3.
Duman et al., "Signaling pathways underlying the rapid antidepressant actions of ketamine", Neuropharmacology, 2012, 62: 35-41.
Duman et al., "Synaptic dysfunction in depression: potential therapeutic targets," Science, 2012, 338: 68-72.
Dwyer et al., "mTOR activation is required for the antidepressant effects of mGluR(2)/(3) blockade", Int. J. Neuropsychoph, 2012, 15: 429-434.
Gardenhire et al., "A Guide To Aerosol Delivery Devices for Respiratory Therapists" 4th Edition, Jan. 1, 2017.
Gillman, "Mini-Review: A Brief History of Nitrous Oxide (N2O) Use in Neuropsychiatry", Current Drug Abuse Reviews, Jun. 2019, 11(1): 12-20.
Gupta et al., "Heliox administration in the pediatric intensive care unit: An evidence-based review", Pediatr Crit Care Med., Mar. 1, 2005, 6(2): 204-211.
Hamishehkar et al., "The Role of Carrier in Dry Powder Inhaler", Recent Advances in Novel Drug Carrier Systems, Oct. 31, 2012, InTech.
Hanan et al., "Pharmacy Practice for Technicians", Fifth Edition, Jan. 3, 2014, p. 261.
Heuer et al., "Comprehensive Respiratory Therapy Exam Preparation Guide", Chapter 12: Administer Medication and Speciality Gases (Section III-D), p. 293, Feb. 22, 2020.
Iida et al, "Preparation of dry powder inhalation by surface treatment of lactose carrier particles." Chem Pharm Bull, 2003, 511150009-2363.
International Search Report and Written Opinion for PCT International Patent Application No. PCT/EP2021/072896, mailed Feb. 4, 2022.
International Search Report and Written Opinion for PCT International Patent Application No. PCT/EP2021/072898, mailed Feb. 4, 2022.
International Search Report and Written Opinion for PCT International Patent Application No. PCT/EP2021/077057, mailed Mar. 18, 2022.
International Search Report and Written Opinion for PCT International Patent Application No. PCT/EP2022/058574, mailed Sep. 12, 2022.
International Search Report and Written Opinion for PCT International Patent Application No. PCT/EP2023/053744, mailed May 19, 2023.
International Search Report and Written Opinion for PCT International Patent Application No. PCT/EP2023/053752, mailed May 11, 2023.
International Search Report and Written Opinion for PCT International Patent Application No. PCT/EP2023/057939, mailed Aug. 14, 2023.
International Search Report and Written Opinion for PCT International Patent Application No. PCT/EP2023/058107, mailed Jul. 23, 2023.
Jernigan et al., "The mTOR signaling pathway in the prefrontal cortex is compromised in major depressive disorde", Prog neuropsychoph, 2011, 35: 1774-1779.
Li et al., "mTOR-dependent synapse formation underlies the rapid antidepressant effects of NMDA antagonists", Science, 2010, 329: 959-964.
Ly et al., "Psychedelics Promote Structural and Functional Neural Plasticity", Cell Rep., 2018, 23(11): 3170-3182.
McKenna et al., "3,4-Methylenedioxyamphetamine (MDA) analogues exhibit differential effects on synaptosomal release of ^3H-dopamine and ^3H-5-hydroxytryptamine", Mar. 1, 1991, 38(3): 505-512.
Monte et al., "Dihydrobenzofuran analogues of hallucinogens. 3. Models of 4-substituted (2,5-dimethoxyphenyl)alkylamine derivatives with rigidified methoxy groups", J Med Chem., Jul. 1996, vol. 39, No. 15, pp. 2953-2961.
Monte et al., "Dihydrobenzofuran analogues of hallucinogens. 4. Mescaline derivatives", Sep. 12, 1997, vol. 40, No. 19, pp. 2997-3008.
Nagele et al, "Nitrous Oxide for Treatment-Resistant Major Depression: A Proof-of-Concept Trial", Biol Psychiatry, Jul. 2015, 78(1): 10-18.
Nagele et al., "A phase 2 trial of inhaled nitrous oxide for treatment-resistant major depression", Science Transl. Med., Jun. 9, 2021, 13(597): eabe1376.
Nichols et al., "1-(2,5-Dimethoxy-4-(trifluoromethyl)phenyl)-2-aminopropane: A Potent Serotonin 5-HT2A/2C Agonist", Journal of Medicinal Chemistry, vol. 37, No. 25, Dec. 1, 1994, pp. 4346-4351.
Partial International Search Report and Invitation to Pay Additional Fees And, Where Applicable, Protest Fee for PCT International Patent Applciation No. PCT/EP2023/057939, mailed Jun. 16, 2023.

(56) References Cited

OTHER PUBLICATIONS

Pham et al., "Ketamine treatment involves medial prefrontal cortex serotonin to induce a rapid antidepressant-like activity in BALB/cJ mice", Neuropharmacology, Jan. 2017, 112(Pt A): 198-209, Epublished May 17, 2016.

Psychonautwiki, 2C-T-x, Retrieved from internet Apr. 21, 2023.

Sepeda et al., "Inhaled 5-methoxy-N,N-dimethyltryptamine: Supportive context associated with positive acute and enduring effects", Journal of Psychadelic Studies, Jun. 1, 2020, 4(2): 114-122.

Sial et al., "Ketamine: The final frontier or another depressing end?", Behav Brain Res., 2020, 383: 112508.

Simmons et al., "Regioselective syntheses of deuterium labelled 6-hydroxydopamines", Journal of Labelled Compounds and Radiopharmaceuticals, vol. 20, No. 3, Mar. 1, 1983, pp. 325-338.

Simoes et al., "Dried blood spots combined to an UPLC-MS/MS method for the simultaneous determination of drugs of abuse in forensic toxicology", Journal Of Pharmaceutical And Biomedical Analysis, Jan. 1, 2018, 147: 634-644.

Tang et al., "Involvement of normalized NMDA receptor and mTOR-related signaling in rapid antidepressant effects of Yueju and ketamine on chronically stressed mice", Sci Rep 5, 2015, 13573.

Trachsel et al., "Synthesis of Fluoro Analogues of 3,4-(Methylenedioxy)amphetamine (MDA) and Its Derivatives", Chemistry & Biodiversity, Mar. 1, 2006, 3(3): 326-336.

Traschel et al., "Flourine in psychadelic phenethylamines", Drug Testing and Analysis, Feb. 28, 2012, 4: 577-590.

Traschel, "Synthesis of Novel (Phenylalkyl)amines for the Investigation of Structure ± Activity Relationships", Helvetica Chimica Acta, 2003, 86: 2610-2619.

Wikipedia, 2C (psychedelics), Retrieved from internet Apr. 21, 2023.

Wikipedia, Substituted phenethylamine, Retrieved from internet Apr. 21, 2023.

Xu et al., "Synthesis of deuterium labeled phenethylamine derivatives", Journal of Labelled Compounds and Radiopharmaceuticals, vol. 49, No. 13, Jan. 1, 2006, pp. 1187-1200.

Heresco-Levy et al., "Synergistic psychedelic—NMDAR modulator treatment forneuropsychiatric disorders", Molecular Psychiatry, Nov. 9, 2023.

International Search Report and Written Opinion for PCT International Patent Application No. PCT/EP2023/080027, mailed Feb. 8, 2024.

Kanamori et al., "A model system for prediction of the in vivo metabolism of designer drugs using three-dimensional culture of rat and human hepatocytes", Forensic Toxicology, Jun. 4, 2011, 29(2): 142-151.

Kanamori et al., "In vivo metabolism of 2, 5-dimethoxy-4-propylthiophenethylamine in rat", Xenobiotica, Jun. 2007, 37(6): 679-692.

Krempien et al., "Randomized, Double-Blind, Placebo-Controlled Study to Evaluate the Safety and Efficacy of CYB003, a Deuterated Psilocybin Analog in Patients with Major Depressive Disorder", ACNP 2023.

\* cited by examiner

THERAPEUTIC PHENETHYLAMINE COMPOSITIONS AND METHODS OF USE

CROSS REFERENCE TO RELATED APPLICATIONS

This application is a 371 of International Application No. PCT/EP2021/072896, filed Aug. 18, 2021, which claims the benefit of U.S. Provisional Application No. 63/067,303 filed Aug. 18, 2020, and U.S. Provisional Application No. 63/131,974 filed Dec. 30, 2020, the entire contents of which are incorporated herein by reference.

FIELD OF THE INVENTION

The present disclosure relates generally to chemical compounds and, in some embodiments, to serotonin 5-$HT_2$ receptor agonists and uses in the treatment of diseases associated with an 5-$HT_2$ receptor.

BACKGROUND OF THE INVENTION

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

There are three, closely related subtypes of serotonin 5-$HT_2$ receptors (5-$HT_2$Rs), 5-$HT_{2A}$, 5-$HT_{2B}$, and 5-$HT_{2C}$, and they are primary targets of classic serotonergic psychedelics, such as lysergic acid diethylamide (LSD), psilocybin, and 2,5-Dimethoxy-4-bromoamphetamine (DOB). Classic serotonergic psychedelics and entactogens have been actively investigated by the research and medical community to alleviate a multitude of central nervous system (CNS) disorders (Reiff, C. M., Richman, E. E., Nemeroff, C. B., Carpenter, L. L., Widge, A. S., Rodriguez, C. I., Kalin, N. H., and McDonald, W. M., 2020, Psychedelics and Psychedelic-Assisted Psychotherapy, *Am J Psychiatry* 177, 391-410), such as: (i) post-traumatic stress disorder (PTSD)(Jerome, L., Feduccia, A. A., Wang, J. B., Hamilton, S., Yazar-Klosinski, B., Emerson, A., Mithoefer, M. C., and Doblin, R., 2020, Long-term follow-up outcomes of MDMA-assisted psychotherapy for treatment of PTSD: a longitudinal pooled analysis of six phase 2 trials, *Psychopharmacology (Berl)* 237, 2485-2497), (ii) major depressive disorder (MDD), (iii) treatment-resistant depression (TRD)(Goldberg, S. B., Pace, B. T., Nicholas, C. R., Raison, C. L., and Hutson, P. R., 2020, The experimental effects of psilocybin on symptoms of anxiety and depression: A meta-analysis, *Psychiatry Res* 284, 112749), (iv) obsessive-compulsive disorder (OCD)(Moreno, F. A., Wiegand, C. B., Taitano, E. K., and Delgado, P. L., 2006, Safety, tolerability, and efficacy of psilocybin in 9 patients with obsessive-compulsive disorder, *J Clin Psychiatry* 67, 1735-1740), (v) social anxiety disorder (ClinicalTrials.gov, number NCT02008396), (vi) substance use disorders, including but not limited to alcohol use disorder, opioid use disorder, amphetamine use disorder, nicotine use disorder, and cocaine use disorder, (vii) anorexia nervosa, (viii) bulimia nervosa (ClinicalTrials.gov, numbers NCT04454684 and NCT04052568), (ix) Alzheimer's disease (ClinicalTrials.gov, number NCT04123314), and (x) cluster headache and migraine (Nichols, D. E., 2016, Psychedelics, *Pharmacol Rev* 68, 264-355; Johnson, M. W., Hendricks, P. S., Barrett, F. S., and Griffiths, R. R., 2019, Classic psychedelics: An integrative review of epidemiology, therapeutics, mystical experience, and brain network function, *Pharmacol Ther* 197, 83-102; Sewell, R. A., Halper, J. H., and Pope, H. G., Jr., 2006, Response of cluster headache to psilocybin and LSD, *Neurology* 66, 1920-1922; ClinicalTrials.gov, number NCT04218539).

These drugs have also been investigated to alleviate conditions of the autonomic nervous system (ANS), including pulmonary disorders (e.g., asthma and chronic obstructive pulmonary disorder (COPD) and cardiovascular disorders (e.g., atherosclerosis), among others (Nichols, D. E., Johnson, M. W, and Nichols, C. D., 2017, Psychedelics as Medicines: An Emerging New Paradigm, *Clin Pharmacol Ther* 101, 209-219; Flanagan, T. W., Sebastian, M. N., Battaglia, D. M., Foster, T. P., Cormier, S. A., and Nichols, C. D., 2019, 5-HT2 receptor activation alleviates airway inflammation and structural remodeling in a chronic mouse asthma model, *Life Sci* 236, 116790; Flanagan, T. W., Sebastian, M. N., Battaglia, D. M., Foster, T. P., Maillet, E. L., and Nichols, C. D., 2019, Activation of 5-HT2 Receptors Reduces Inflammation in Vascular Tissue and Cholesterol Levels in High-Fat Diet-Fed Apolipoprotein E Knockout Mice, *Sci Rep* 9, 13444; Sexton, J. D., Nichols, C. D., and Hendricks, P. S., 2019, Population Survey Data Informing the Therapeutic Potential of Classic and Novel Phenethylamine, Tryptamine, and Lysergamide Psychedelics, *Front Psychiatry* 10, 896).

Some studies have advanced into Phase III trials, for example the use of 3,4-methylenedioxymethamphetamine (MDMA) for the treatment of PTSD (Feduccia, A. A., Jerome, L., Yazar-Klosinski, B., Emerson, A., Mithoefer, M. C., and Doblin, R., 2019, Breakthrough for Trauma Treatment: Safety and Efficacy of MDMA-Assisted Psychotherapy Compared to Paroxetine and Sertraline, *Front Psychiatry* 10, 650), and phase 1 trials of 3,4,5-trimethoxyphenethylamine (mescaline) have begun (ClinicalTrials.gov, number NCT04227756).

Mechanistically, the therapeutic effects of psychedelic phenethylamines are thought to be mediated by their interaction with serotonin (5-HT) receptors, particularly 5-$HT_{2A}$ receptors, though other targets, including the 5-$HT_{1A}$ receptor may also be involved (Nichols, D. E., 2016, Psychedelics, *Pharmacol Rev* 68, 264-355; Canal, C. E., 2018, Serotonergic Psychedelics: Experimental Approaches for Assessing Mechanisms of Action, *Handb Exp Pharmacol* 252, 227-260). A contribution from the 5-HT2c receptor may be responsible for the reported anti-addictive properties of classic psychedelics (Canal, C. E., and Murnane, K. S., 2017, The serotonin 5-HT2C receptor and the non-addictive nature of classic hallucinogens, *J Psychopharmacol* 31, 127-143). The effects of entactogen phenethylamines are mediated primarily by their interaction with monoamine transporters, particular the serotonin (SERT) and dopamine (DAT) transporters (Jayanthi, L. D., and Ramamoorthy, S., 2005, Regulation of monoamine transporters: influence of psychostimulants and therapeutic antidepressants, *AAPS J* 7, E728-738).

Safety aspects of psychedelics and entactogens remain a key challenge for clinical applications (Hasler, F., Grimberg, U., Benz, M. A., Huber, T., and Vollenweider, F. X., 2004, Acute psychological and physiological effects of psilocybin in healthy humans: a double-blind, placebo-controlled dose-effect study, *Psychopharmacology (Berl)* 172, 145-156; Carbonaro, T. M., Bradstreet, M. P., Barrett, F. S., MacLean, K. A., Jesse, R., Johnson, M. W., and Griffiths, R. R., 2016, Survey study of challenging experiences after ingesting psilocybin mushrooms: Acute and enduring positive and negative consequences, *J Psychopharmacol* 30, 1268-1278; Garcia-Romeu, A., Kersgaard, B., and Addy, P. H., 2016, Clinical applications of hallucinogens: A review, *Exp Clin Psychopharmacol* 24, 229-268; Morgan, L., 2020, MDMA-assisted psychotherapy for people diagnosed with treatment-resistant PTSD: what it is and what it isn't, *Ann Gen Psychiatry* 19, 33; Schenk, S., and Newcombe, D., 2018, Methylenedioxymethamphetamine (MDMA) in Psychiatry: Pros, Cons, and Suggestions, *J Clin Psychopharmacol* 38, 632-638).

Clearly, a safe therapeutic window for this class of drugs is very narrow, because of cardiovascular complications associated with prolonged, increased serotonin release and $5-HT_{2B}$ stimulation (Huang, X.-P., Setola, V., Yadav, P. N., Allen, J. A., Rogan, S. C., Hanson, B. J., Revankar, C., Robers, M., Doucette, C., and Roth, B. L., 2009, Parallel Functional Activity Profiling Reveals Valvulopathogens Are Potent 5-Hydroxytryptamine(2B) Receptor Agonists: Implications for Drug Safety Assessment, *Molecular Pharmacology* 76, 710-722; Rothman, R. B., and Baumann, M. H., 2009, Serotonergic drugs and valvular heart disease, *Expert Opin Drug Saf* 8, 317-329), depressive after-effects associated with depletion of central serotonin levels (Parrott, A. C., 2014, The potential dangers of using MDMA for psychotherapy, *J Psychoactive Drugs* 46, 37-43), and numerous other acute adverse effects, including anxiety, fear, tachycardia, hypertension, increased body temperature, nausea and vomiting, with many acute adverse effects being attributed to high drug concentrations ("spiking") in the blood shortly after oral administration (Meyer, J. S., 2013, 3,4-methylenedioxymethamphetamine (MDMA): current perspectives, *Subst Abuse Rehabil* 4, 83-99; Baylen, C. A., and Rosenberg, H., 2006, A review of the acute subjective effects of MDMA/ecstasy, *Addiction* 101, 933-947; Shulgin, A., and Shulgin, Ann., 1991, *Pihkal: a chemical love story*, Transform Press, Berkeley, CA; Barrett, F. S., Bradstreet, M. P., Leoutsakos, J. S., Johnson, M. W., and Griffiths, R. R., 2016, The Challenging Experience Questionnaire: Characterization of challenging experiences with psilocybin mushrooms, *J Psychopharmacol* 30, 1279-1295). Many psychedelics and entactogens are also long acting, and thus require full day supervision considering their narrow therapeutic window, which is a major impediment to their clinical use.

One class of psychedelic phenethylamines is the 2C—X family of phenethylamines (phenethylamines containing 2,4,5 substitution, with methoxy groups at the 2 and 5 positions of the phenyl group). Members of this class, such as 2,5-dimethoxy-4-bromophenethylamine (2C—B), may be used to treat sexual dysfunctions (Shulgin, A., and Shulgin, Ann., 1991, *Pihkal: a chemical love story*, Transform Press, Berkeley, CA), as well as neuropsychiatric conditions, and induce changes in perception, cognition, emotion, and mood that may underlie its reported neuropsychotherapeutic benefits (Johnson, M. W., Hendricks, P. S., Barrett, F. S., and Griffiths, R. R., 2019, Classic psychedelics: An integrative review of epidemiology, therapeutics, mystical experience, and brain network function, *Pharmacol Ther* 197, 83-102).

However, wider clinical testing and finding practical treatment protocols for 2C—X compounds is challenged by the following factors: 1) poor oral bioavailability; 2) low brain penetration; 3) delayed effects from oral administration; 4) therapeutic effects requiring high doses; 5) acute psychiatric adverse events (AE), such as fear, anxiety, and paranoia, cardiovascular events including tachycardia and hypertension, and gastrointestinal effects including nausea; and 6) toxicity. These properties are thought to be due to rapid first-pass metabolism through deamination/oxidation by monoamine oxidases (MAO), MAO-A and MAO-B and O-dealkylation by cytochrome P450 enzymes such as CYP2D6, and also to their relatively hydrophilic nature (e.g., 2,4,5-trimethoxphenethylamine (2C—O) possesses a log P value of 0.98; ChemDraw) which limits distribution to the brain (Suzuki, O., Katsumata, Y., and Oya, M., 1981, Oxidation of beta-phenylethylamine by both types of monoamine oxidase: examination of enzymes in brain and liver mitochondria of eight species, *J Neurochem* 36, 1298-1301; Monte, A. P., Marona-Lewicka, D., Parker, M. A., Wainscott, D. B., Nelson, D. L., and Nichols, D. E., 1996, Dihydrobenzofuran analogues of hallucinogens. 3. Models of 4-substituted (2,5-dimethoxyphenyl)alkylamine derivatives with rigidified methoxy groups, *J Med Chem* 39, 2953-2961; Monte, A. P., Waldman, S. R., Marona-Lewicka, D., Wainscott, D. B., Nelson, D. L., Sanders-Bush, E., and Nichols, D. E., 1997, Dihydrobenzofuran analogues of hallucinogens. 4. Mescaline derivatives, *J Med Chem* 40, 2997-3008). For example, 2,4,5-trimethoxphenethylamine (2C—O) is inactive after oral administration (Shulgin, A. T., 1978, Psychotomimetic Drugs: Structure-activity relationships. Chapter 6, In *Handbook of psychopharmacology, V.11-Stimulants*, pp 243-333, Plenum Press, New York).

The limitations of current 2C—X compounds and formulations thereof, and other psychedelic and entactogen phenethylamines, are apparent—and it has proven difficult to control drug exposure and maintain drug concentrations in the safe and efficacious range.

SUMMARY OF THE INVENTION

In view of the forgoing, there is a need for novel 2C—X phenethylamine compounds which have improved pharmacokinetic properties—that are bioavailable, brain penetrable, have fast onset, and are short acting—and which demonstrate enhanced activity while minimizing psychiatric adverse events and toxicity. There is a further need for efficient, more convenient, and controllable phenethylamine formulations that afford no neurologically toxic (e.g., psychotomimetic toxic) plasma concentration.

Accordingly, it is one object of the present invention to provide novel compounds that meet these criteria.

It is another object of the present disclosure to provide novel pharmaceutical compositions which contain the compounds.

It is another object of the present disclosure to provide novel methods of treating a subject with a disease or disorder associated with a serotonin $5-HT_2$ receptor with the compounds.

It is another object of the present disclosure to provide novel tablet compositions, such as single-layer orally administered tablet compositions, containing the compounds.

It is another object of the present disclosure to provide novel kits containing formulations of the compounds for use in treatment.

It is yet another object of the present disclosure to provide novel methods of delivering the compounds in a mist via inhalation, such as for the treatment of a central nervous system (CNS) disorder or psychological disorder.

It is yet another object of the invention to provide a novel use of the compounds for treating a subject with a disease or disorder associated with a serotonin $5-HT_2$ receptor, such as a central nervous system (CNS) disorder or psychological disorder.

These and other objects, which will become apparent during the following detailed description, have been achieved by the inventors' discovery that the novel compounds described herein (e.g., compounds of Formulas (I) through (IV)) having site-specific deuteration/fluorination maintain preferential binding to G-protein coupled receptors (GPCRs), e.g., 5-HT$_2$ receptors, have improved exposure (e.g., prevent high drug concentrations (spiking) observed acutely after administration), and possess advantageous enzymatic degradation profiles for improved bioavailability, brain penetration, and prevention/reduction of toxic metabolite formation.

Thus, the present invention provides:

(1) A compound having a structure of formula (I):

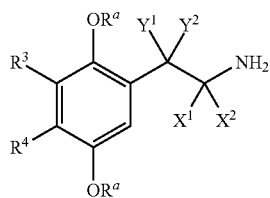

(I)

or a pharmaceutically acceptable salt, solvate, stereoisomer, or prodrug thereof,
wherein:

$X^1$ and $X^2$ are independently hydrogen or deuterium;
$Y^1$ and $Y^2$ are independently hydrogen or deuterium;
$R^3$ is hydrogen or deuterium;
$R^4$ is halogen, a substituted or unsubstituted $C_1$-$C_6$ alkyl, a substituted or unsubstituted $C_3$-$C_{10}$ cycloalkyl, —OR$^b$, or —SR$^b$;
each R$^a$ is independently a substituted or unsubstituted $C_1$-$C_6$ alkyl; and
R$^b$ is hydrogen, deuterium, a substituted or unsubstituted $C_1$-$C_6$ alkyl, or a substituted or unsubstituted $C_3$-$C_{10}$ cycloalkyl;
with the proviso that at least one of $X^1$, $X^2$, $Y^1$, $Y^2$, $R^3$, $R^4$, and R$^a$, comprises deuterium and/or $R^4$ is selected from the group consisting of —SCF$_3$, —SCH$_2$CH$_2$CF$_3$, —SCH$_2$CH$_2$CF$_2$H, —SCH$_2$CH$_2$CFH$_2$, —OCH$_2$CH$_2$CF$_3$, —OCH$_2$CH$_2$CF$_2$H, and —OCH$_2$CH$_2$CFH$_2$.

(2) The compound of (1), wherein $Y^1$ and $Y^2$ are hydrogen.

(3) The compound of (1) or (2), wherein $R^3$ is hydrogen.

(4) The compound of any one of (1) to (3), wherein $X^1$ and $X^2$ are hydrogen.

(5) The compound of any one of (1) to (3), wherein $X^1$ and $X^2$ are deuterium.

(6) The compound of any one of (1) to (5), wherein each R$^a$ is —CH$_3$ or -CD$_3$.

(7) The compound of any one of (1) to (6), wherein $R^4$ is —SMe, —SCD$_3$, —SCF$_3$, —SCH$_2$CH$_2$CF$_3$, —SCH$_2$CH$_2$CF$_2$H, —SCH$_2$CH$_2$CFH$_2$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, —OCH$_2$CH$_2$CF$_3$, —OCH$_2$CH$_2$CF$_2$H, —OCH$_2$CH$_2$CFH$_2$, —Cl, —I, or —Br.

(8) The compound of (1), having a structure of formula (II):

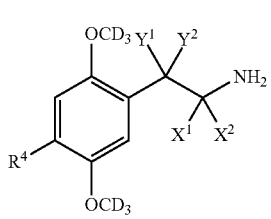

(II)

or a pharmaceutically acceptable salt, solvate, stereoisomer, or prodrug thereof,
wherein:

$X^1$ and $X^2$ are independently hydrogen or deuterium;
$Y^1$ and $Y^2$ are independently hydrogen or deuterium;
$R^4$ is halogen, a substituted or unsubstituted $C_1$-$C_6$ alkyl, a substituted or unsubstituted $C_3$-$C_{10}$ cycloalkyl, —OR$^b$, or —SR$^b$; and
R$^b$ is hydrogen, deuterium, a substituted or unsubstituted $C_1$-$C_6$ alkyl, or a substituted or unsubstituted $C_3$-$C_{10}$ cycloalkyl.

(9) The compound of (8), wherein $X^1$ and $X^2$ are hydrogen.

(10) The compound of (8) or (9), wherein $R^4$ is —SMe, —SCD$_3$, —SCF$_3$, —SCH$_2$CH$_2$CF$_3$, —SCH$_2$CH$_2$CF$_2$H, —SCH$_2$CH$_2$CFH$_2$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, —OCH$_2$CH$_2$CF$_3$, —OCH$_2$CH$_2$CF$_2$H, —OCH$_2$CH$_2$CFH$_2$, —Cl, —I, or —Br.

(11) The compound of any one of (8) to (10), wherein $R^4$ is —SMe, -Me, —OCD$_3$, —CF$_3$, -t-Bu, or -cyclopentyl.

(12) The compound of (1), having a structure of formula (III):

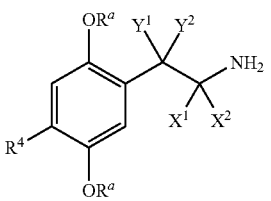

(III)

or a pharmaceutically acceptable salt, solvate, stereoisomer, or prodrug thereof,
wherein:

$X^1$ and $X^2$ are independently hydrogen or deuterium;
$Y^1$ and $Y^2$ are independently hydrogen or deuterium;
$R^4$ is a $C_1$-$C_6$ alkyl substituted with one or more deuterium, a $C_3$-$C_{10}$ cycloalkyl substituted with one or more deuterium, —OR$^b$, or —SR$^b$;
each R$^a$ is independently a substituted or unsubstituted $C_1$-$C_6$ alkyl; and
Re is a $C_1$-$C_6$ alkyl substituted with one or more deuterium or a $C_3$-$C_{10}$ cycloalkyl substituted with one or more deuterium.

(13) The compound of (12), wherein $X^1$ and $X^2$ are hydrogen and each R$^a$ is —CH$_3$.

(14) The compound of (12) or (13), wherein $R^4$ is —SCD$_3$, —CD$_3$, —C(CD$_3$)$_3$, or —OCD$_3$.

(15) The compound of (1), having a structure of formula (IV):

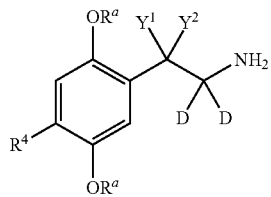

(IV)

or a pharmaceutically acceptable salt, solvate, stereoisomer, or prodrug thereof, wherein:

$Y^1$ and $Y^2$ are independently hydrogen or deuterium;

$R^4$ is halogen, a substituted or unsubstituted $C_1$-$C_6$ alkyl, a substituted or unsubstituted $C_3$-$C_{10}$ cycloalkyl, —$OR^b$, or —$SR^b$;

each $R^a$ is independently a substituted or unsubstituted $C_1$-$C_6$ alkyl; and $R^b$ is hydrogen, deuterium, a substituted or unsubstituted $C_1$-$C_6$ alkyl, or a substituted or unsubstituted $C_3$-$C_{10}$ cycloalkyl.

(16) The compound of any one of (1) to (15), which is selected from the group consisting of

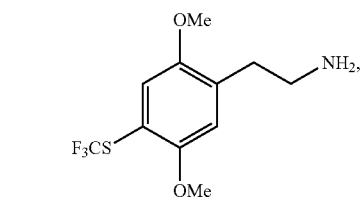

(I-1)

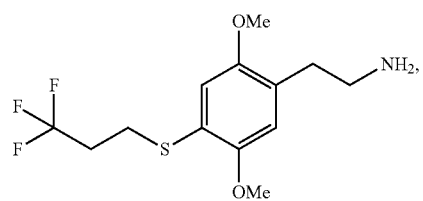

(I-2)

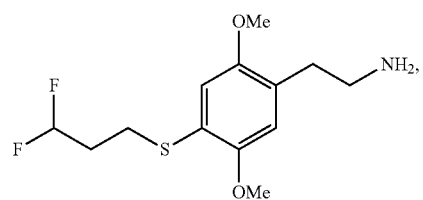

(I-3)

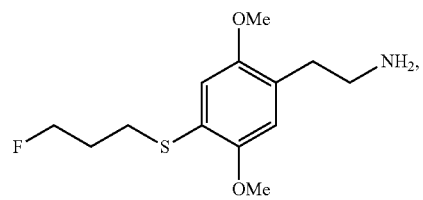

(I-4)

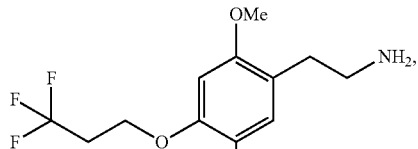

(I-5)

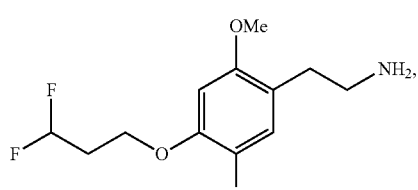

(I-6)

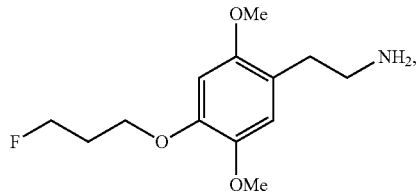

(I-7)

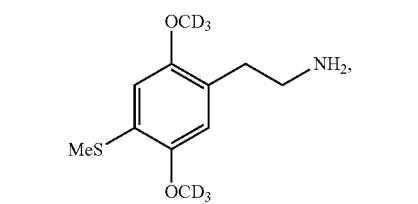

(II-1)

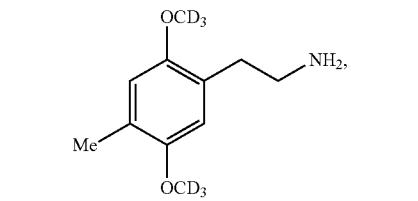

(II-2)

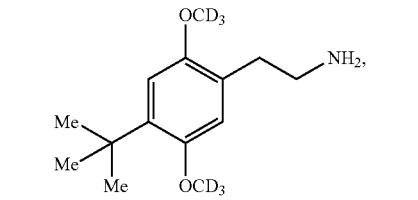

(II-3)

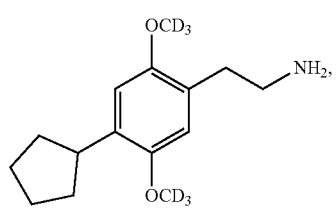

(II-4)

-continued
(II-5)
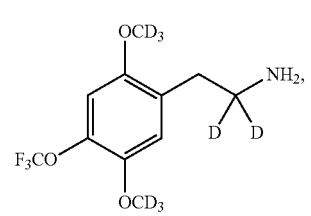
(II-6)
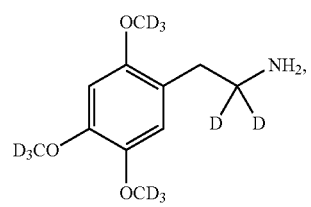
(II-7)
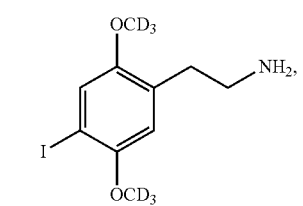
(II-8)
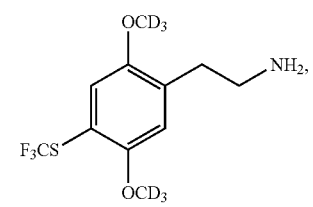
(II-9)
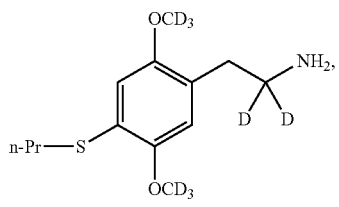
(II-10)
(II-11)
-continued
(II-12)
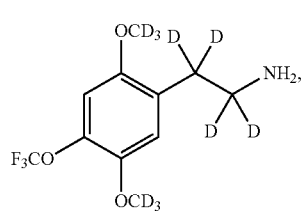
(II-13)
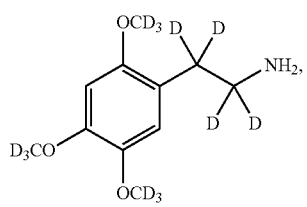
(II-14)
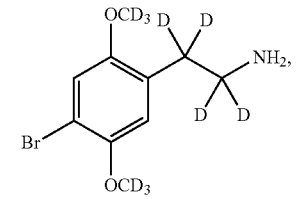
(II-15)
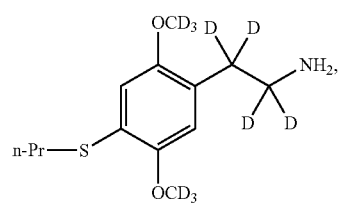
(II-16)
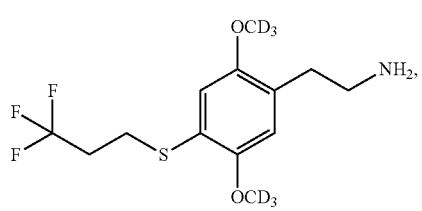
(II-17)
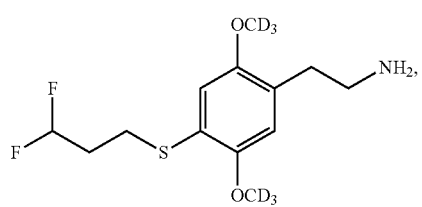
(II-18)
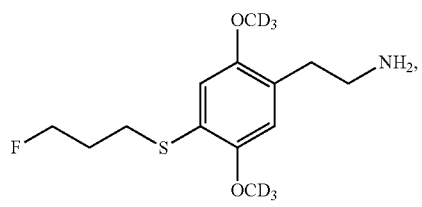

-continued (II-19) (II-20) (II-21) (III-1) (III-2) (IV-1) (IV-2) (IV-3) (IV-4) (IV-5) (IV-6) (IV-7) (IV-8) (IV-9) (IV-10) (IV-11)

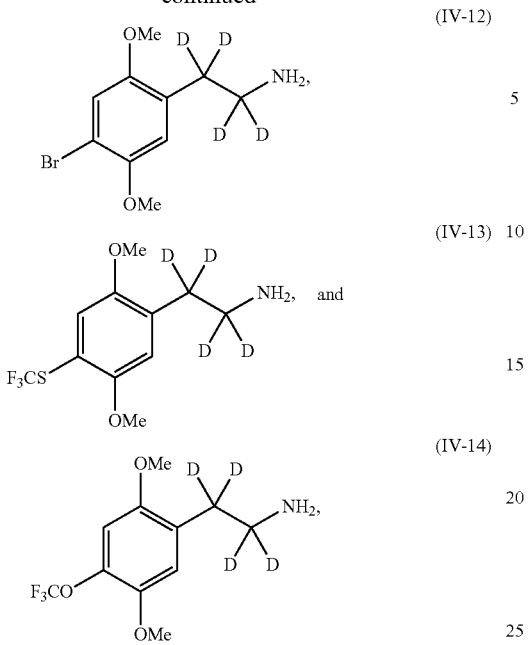

pharmaceutically acceptable salt, solvate, or prodrug thereof.

(17) The compound of any one of (1) to (16), wherein the compound is an agonist of a serotonin 5-$HT_2$ receptor.

(18) The compound of any one of (1) to (17), wherein the compound is an agonist of a serotonin 5-$HT_{2A}$ receptor.

(19) A pharmaceutical composition, comprising the compound of any one of (1) to (18) and a pharmaceutically acceptable excipient.

(20) The pharmaceutical composition of (19), wherein the compound is present in the pharmaceutical composition at a purity of at least 50% by weight based on a total weight of isotopologues of the compound present in the pharmaceutical composition.

(21) The pharmaceutical composition of (19) or (20), wherein any position in the compound having deuterium has a minimum deuterium incorporation of at least 50 atom % at the site of deuteration.

(22) The pharmaceutical composition of any one of (19) to (20), which is substantially free of other isotopologues of the compound.

(23) The pharmaceutical composition of any one of (19) to (22), which is formulated for oral administration.

(24) The pharmaceutical composition of any one of (19) to (22), which is formulated for administration via inhalation.

(25) A method of treating a subject with a disease or disorder associated with a serotonin 5-$HT_2$ receptor, the method comprising:
administering to the subject a therapeutically effective amount of the compound of any one of (1) to (18).

(26) The method of (25), wherein the disease or disorder associated with a serotonin 5-$HT_2$ receptor is a neuropsychiatric disease or disorder or an inflammatory disease or disorder.

(27) The method of (25) or (26), wherein the disease or disorder associated with a serotonin 5-$HT_2$ receptor is a central nervous system (CNS) disorder.

(28) The method of (27), wherein the central nervous system (CNS) disorder is selected from the group consisting of post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), a bipolar disorder and related disorders, cyclothymic disorder, obsessive-compulsive disorder (OCD), generalized anxiety disorder (GAD), social anxiety disorder, a substance use disorder, anorexia nervosa, bulimia nervosa, binge eating disorder, Alzheimer's disease, cluster headache and migraine, attention deficit hyperactivity disorder (ADHD), pain, aphantasia, childhood-onset fluency disorder, major neurocognitive disorder, mild neurocognitive disorder, sexual dysfunction, chronic fatigue syndrome, Lyme disease, and obesity.

(29) The method of (27) or (28), wherein the central nervous system (CNS) disorder is pain.

(30) The method of (27) or (28), wherein the central nervous system (CNS) disorder is sexual dysfunction.

(31) The method of (25) or (26), wherein the disease or disorder associated with a serotonin 5-$HT_2$ receptor is an autonomic nervous system (ANS) disorder.

(32) The method of (31), wherein the autonomic nervous system (ANS) disorder is a pulmonary disorder or a cardiovascular disorder.

(33) The method of any one of (25) to (32), wherein the compound is administered orally, sublingually, buccally, topically, via injection, or via inhalation.

(34) A single-layer orally administered tablet composition comprising the compound of any one of (1) to (18), and a polymer.

(35) The single-layer orally administered tablet composition of (34), wherein the composition is adapted for maximum sustained release.

(36) The single-layer orally administered tablet composition of (34) or (35), wherein the tablet composition comprises a combination of (i) a water-insoluble neutrally charged non-ionic matrix; (ii) a polymer carrying one or more negatively charged groups; and (iii) the compound.

(37) The single-layer orally administered tablet composition of (36), wherein the water-insoluble neutrally charged non-ionic matrix is selected from a cellulose-based polymer, alone or enhanced by mixing with components selected from the group consisting of starches; waxes; neutral gums; polymethacrylates; PVA; PVA/PVP blends; and mixtures thereof.

(38) The single-layer orally administered tablet composition of (37), wherein the cellulose-based polymer is hydroxypropyl methylcellulose (HPMC).

(39) The single-layer orally administered tablet composition of any one of (36) to (38), wherein the polymer carrying one or more negatively charged groups is selected from the group consisting of polyacrylic acid, polylactic acid, polyglycolic acid, polymethacrylate carboxylate, a cation-exchange resin, a clay, a zeolite, hyaluronic acid, an anionic gum, salts thereof, and mixtures thereof.

(40) The single-layer orally administered tablet composition of (39), wherein the anionic gum is selected from the group consisting of a naturally occurring material and a semi-synthetic material.

(41) The single-layer orally administered tablet composition of (40), wherein the naturally occurring material is selected from the group consisting of alginic acid,

(42) The single-layer orally administered tablet composition of (40), wherein the semi-synthetic material is selected from the group consisting of carboxymethylchitin and cellulose gum.

(43) The single-layer orally administered tablet composition of any one of (34) to (42), comprising a therapeutically effective amount of the compound for the treatment of pain.

(44) The single-layer orally administered tablet composition of any one of (34) to (42), comprising a therapeutically effective amount of the compound for the treatment of brain injury.

(45) The single-layer orally administered tablet composition of any one of (34) to (42), comprising a therapeutically effective amount of the compound for the treatment of depression.

(46) The single-layer orally administered tablet composition of any one of (34) to (42), comprising a therapeutically effective amount of the compound for use in treating a disease or disorder associated with a serotonin 5-HT2 receptor.

(47) The single-layer orally administered tablet composition of (46), wherein the disease or disorder is a central nervous system (CNS) disorder selected from the group consisting of post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme disease, and obesity.

(48) The single-layer orally administered tablet composition of (46), wherein the disease or disorder is a condition of the autonomic nervous system (ANS).

(49) The single-layer orally administered tablet composition of (46) or (48), wherein the disease or disorder is a pulmonary disorder.

(50) The single-layer orally administered tablet composition of (46) or (48), wherein the disease or disorder is a cardiovascular disorder.

(51) The single-layer orally administered tablet composition of any one of (34) to (50), wherein the composition achieves a combined concentration of the compound in plasma in the range of 10-500 ng/ml, and maintains this concentration for a duration of release.

(52) The single-layer orally administered tablet composition of any one of (34) to (51), wherein the polymer comprises one or more negatively charged groups.

(53) A tablet composition formulated for oral administration comprising the compound of any one of (1) to (18), and a polymer.

(54) The tablet composition of (53), wherein the polymer comprises one or more negatively charged groups.

(55) The tablet composition of (53) or (54), wherein the polymer comprises one or more acid groups.

(56) The tablet composition of any one of (53) to (55), wherein the polymer comprises a water-insoluble neutrally charged non-ionic matrix.

(57) The tablet composition of (56), wherein the water-insoluble neutrally charged non-ionic matrix is selected from a cellulose-based polymer, alone or enhanced by mixing with components selected from the group consisting of starches; waxes; neutral gums; polymethacrylates; PVA; PVA/PVP blends; and mixtures thereof.

(58) The tablet composition of (57), wherein the cellulose-based polymer is hydroxypropyl methylcellulose (HPMC).

(59) A kit for the treatment of a subject comprising 1) a single-layer orally administered tablet composition of any one of (34) to (52), and 2) instructions for use in the treatment of pain.

(60) The kit of (59), wherein the polymer comprises one or more negatively charged groups.

(61) A kit for the treatment of a subject comprising 1) a single-layer orally administered tablet composition of any one of (34) to (52), and 2) instructions for use in the treatment of brain injury.

(62) The kit of (61), wherein the polymer comprises one or more negatively charged groups.

(63) A kit for the treatment of a subject comprising 1) a single-layer orally administered tablet composition of any one of (34) to (52), and 2) instructions for use in the treatment of depression.

(64) The kit of (63), wherein the polymer comprises one or more negatively charged groups.

(65) A kit for the treatment of a subject comprising 1) a single-layer orally administered tablet composition of any one of (34) to (52), and 2) instructions for use in the treatment of a disease or disorder associated with a serotonin 5-HT2 receptor.

(66) The kit of (65), wherein the polymer comprises one or more negatively charged groups.

(67) A method of delivering a psychedelic drug to a patient in need thereof comprising administering a psychedelic drug dissolved in a liquid phase of a mist via inhalation, wherein the psychedelic drug comprises the compound of any one of (1) to (18).

(68) The method of (67), wherein the psychedelic drug is delivered to the patient's central nervous system.

(69) The method of (67) or (68), wherein the psychedelic drug is delivered with air, oxygen, or a mixture of helium and oxygen.

(70) The method of any one of (67) to (69), wherein the psychedelic drug is delivered with a mixture of helium and oxygen.

(71) The method of (70), wherein the mixture of helium and oxygen is heated to about 50° C. to about 60° C.

(72) The method of (70) or (71), wherein the helium is present in the mixture of helium and oxygen at about 50 to 90% and the oxygen is present in the mixture of helium and oxygen at about 10 to 50%.

(73) The method of any one of (70) to (72), further comprising administering a pretreatment inhalation therapy prior to administration of the mixture of helium d oxygen and the psychedelic drug.

(74) The method of (73), wherein the pretreatment comprises administering via inhalation a mixture of helium and oxygen heated to about 90° C. to about 120° C. to the patient.

(75) The method of any one of (67) to (74), further comprising (i) administering via inhalation a mixture of helium and oxygen heated to about 90° C. to about 120° C. to the patient, and (ii) administering via inhalation to the patient a mist comprising helium and oxygen heated to about 50° C. to about 60° C. and the psychedelic drug.

(76) The method of (75), further comprising repeating steps (i) and (ii) at least one time.

(77) The method of any one of (67) to (76), wherein the psychedelic drug is delivered to the patient's central nervous system with an improvement in drug bioavailability by at least 25% as compared to oral delivery, increased $C_{max}$ by at least 25% as compared to oral delivery, reduced $T_{max}$ by at least 50% as compared to oral delivery, or a combination thereof.

(78) A method of treating a central nervous system (CNS) disorder or psychological disorder comprising administering, via inhalation, a psychedelic drug dissolved in a mist, wherein the psychedelic drug comprises the compound of any one of (1) to (18).

(79) The method of (78), wherein the psychedelic drug is delivered with air, oxygen, or a mixture of helium and oxygen.

(80) The method of (79), wherein the psychedelic drug is delivered with the mixture of helium and oxygen, and the mixture of helium and oxygen is heated to about 50° C. to about 60° C. prior to administering the psychedelic drug to the patient.

(81) The method of any one of (78) to (80), wherein the CNS disorder is post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme disease, or obesity.

(82) A transdermal patch, comprising the compound of any one of (1) to (18).

(83) The transdermal patch of (82), further comprising a pressure sensitive adhesive layer, a backing, and a release liner.

(84) The transdermal patch of (83), wherein the compound is uniformly distributed throughout the pressure sensitive adhesive layer.

(85) The transdermal patch of any one of (82) to (84), comprising 5 mg to 25 mg of the compound.

(86) A method of treating a subject with a disease or disorder associated with a serotonin 5-HT2 receptor, the method comprising:

administering to the subject, via the transdermal patch of any one of (82) to (85), a therapeutically effective amount of the compound.

(87) The method of (86), wherein the disease or disorder associated with a serotonin 5-$HT_2$ receptor is a neuropsychiatric disease or disorder or an inflammatory disease or disorder.

(88) The method of (86) or (87), wherein the disease or disorder associated with a serotonin 5-HT2 receptor is a central nervous system (CNS) disorder.

(89) The method of (88), wherein the central nervous system (CNS) disorder is selected from the group consisting of post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), a bipolar disorder and related disorders, cyclothymic disorder, obsessive-compulsive disorder (OCD), generalized anxiety disorder (GAD), social anxiety disorder, a substance use disorder, anorexia nervosa, bulimia nervosa, binge eating disorder, Alzheimer's disease, cluster headache and migraine, attention deficit hyperactivity disorder (ADHD), pain, aphantasia, childhood-onset fluency disorder, major neurocognitive disorder, mild neurocognitive disorder, sexual dysfunction, chronic fatigue syndrome, Lyme disease, and obesity.

(90) The method of (86) or (87), wherein the disease or disorder associated with a serotonin 5-$HT_2$ receptor is an autonomic nervous system (ANS) disorder.

(91) The method of (90), wherein the autonomic nervous system (ANS) disorder is a pulmonary disorder or a cardiovascular disorder.

(92) The method of any one of (86) to (91), wherein 5 mg to 25 mg of the compound is administered to the subject over a 4 to 72 hour period.

(93) The method of any one of (86) to (92), wherein a serotonergic, but sub-psychoactive concentration of the compound is administered.

(94) A method of treating a subject with a disease or disorder associated with a serotonin 5-$HT_2$ receptor, the method comprising:

administering to the subject transdermally, subcutaneously, or intramuscularly, via an automatic injection device, a therapeutically effective amount of the compound of any one of (1) to (18).

BRIEF DESCRIPTION OF THE DRAWINGS

The forgoing paragraphs have been provided by way of general introduction and are not intended to limit the scope of the following claims. The described embodiments, together with further advantages, will be best understood by reference to the following detailed description when considered in conjunction with the accompanying drawings, wherein:

DETAILED DESCRIPTION

Figure 1:
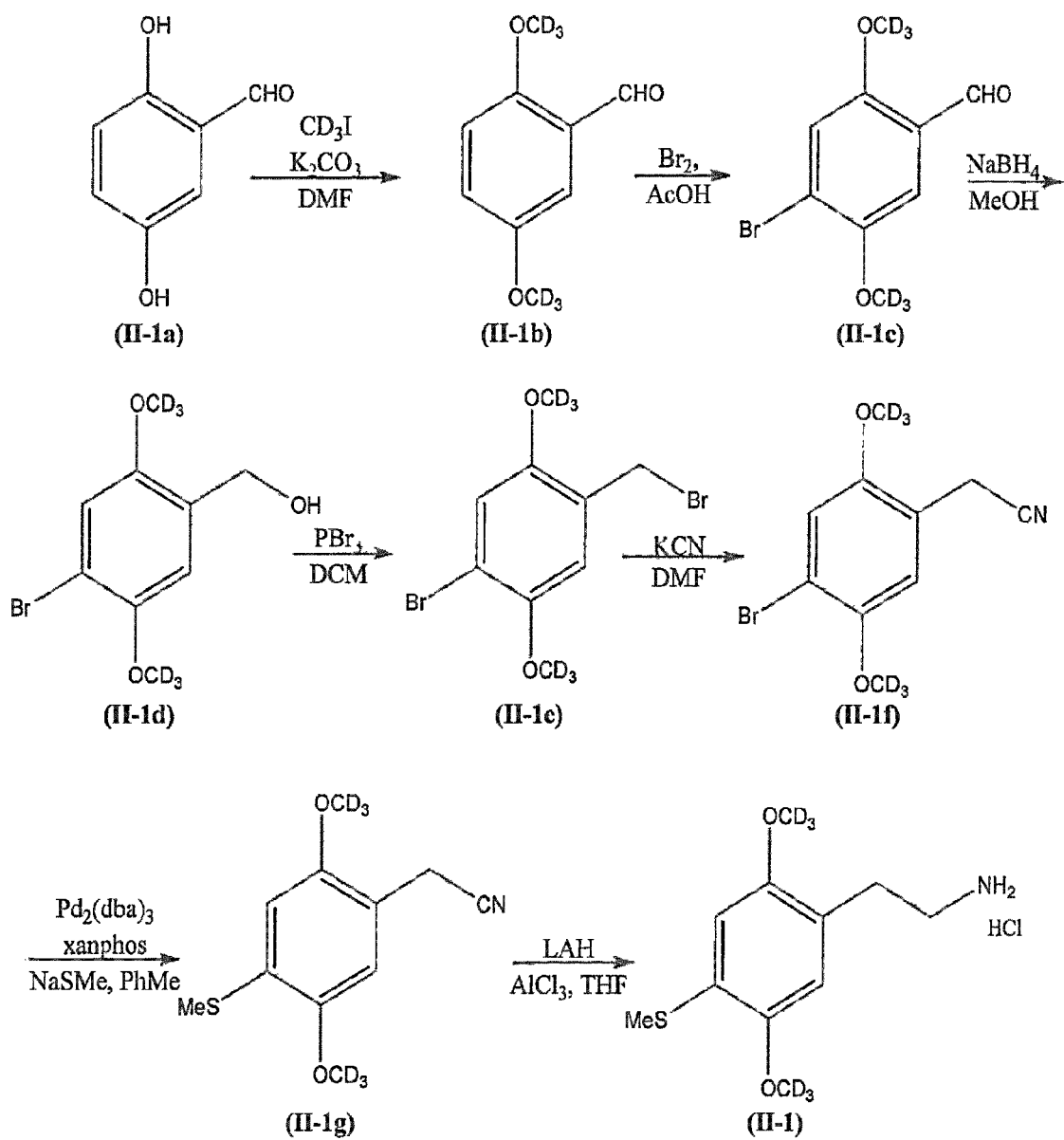
FIG. 1 illustrates the synthetic route for making Compound II-1.

In the following detailed description of the embodiments of the instant disclosure, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the instant disclosure.

Definitions

Unless defined otherwise, all technical and scientific terms used herein have the same meaning as is commonly understood by one of skill in the art to which this disclosure belongs.

"Alkyl" refers to monovalent saturated aliphatic hydrocarbyl groups having from 1 to 10 carbon atoms and such as 1 to 6 carbon atoms, or 1 to 5, or 1 to 4, or 1 to 3, or 1 to 2 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), see-butyl (($CH_3)(CH_3CH_2)CH$—), t-butyl (t-Bu)(($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 10 substituents selected from the group consisting of deuterium, alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NR'R", wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups having from 1 to 6, including, for example, 1 to 3 carbon atoms that are either straight-chained or branched, and which are optionally interrupted with one or more groups selected from —O—, —$NR^{10}$—, —$NR^{10}C(O)$—, —$C(O)NR^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR" where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O- alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms, for example 2 to 4 carbon atoms and having at least 1, for example from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms, for example, 2 to 3 carbon atoms and having at least 1 and for example, from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from deuterium, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O) O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O— cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclohexyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from deuterium, alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and for example, from 1 to 2 double bonds.

The term "substituted cycloalkenyl" refers to cycloalkenyl groups having from 1 to 5 substituents, or from 1 to 3 substituents, selected from deuterium, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring.

In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, benzo[d][1,3]oxathiole, benzo[d][1,3]dioxole, and the like.

Unless otherwise constrained by the definition for the heterocyclic substituent, such heterocyclic groups can be optionally substituted with 1 to 5, or from 1 to 3 substituents, selected from deuterium, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —S.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the ter "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, deuterium, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{8}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as +, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the disclosure and the other a typical counter ion such as chloride, or two ionized compounds disclosed herein can serve as counter ions for such divalent alkali earth ions, or a doubly ionized compound of the disclosure can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, deuterium, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{7}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein, unless specified otherwise. In such cases, the maximum number of such substitutions is three. For example, serial substitutions of substituted aryl groups specifically contemplated herein are limited to substituted aryl-(substituted aryl)-substituted aryl. However, substituent groups defined as e.g., polyethers may contain serial substitution greater than three, e.g., —O—(CH$_2$CH$_2$O)$_n$—H, where n can be 1, 2, 3, or greater.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

When it is defined that a substituent or group "comprise(s) deuterium" or is "comprising deuterium," it is to be understood that the substituent or group may itself be deuterium, or the substituent or group may contain at least one deuterium substitution in its chemical structure. For example, when substituent "—R" is defined to comprise deuterium, it is to be understood that —R may be —D (-deuterium), or a group such as —CD$_3$ that is consistent with the other requirements set forth of —R.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers. All forms such as racemates and optically pure stereoisomers of the compounds are contemplated herein. Chemical formulas and compounds which possess at least one stereogenic center, but are drawn without reference to stereochemistry, are intended to encompass both the racemic compound, as well as the separate stereoisomers, e.g., R- and/or S-stereoisomers, each permutation of diastereomers so long as those diastereomers are geometrically feasible, etc.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautaomeric ring atom arrangements are possible.

It will be appreciated that the compounds herein can exist in different salt, solvate, and stereoisomer forms, and the present disclosure is intended to include all permutations of salts, solvates and stereoisomers, such as a solvate of a pharmaceutically acceptable salt of a stereoisomer of subject compound.

As used herein, the language "maximum sustained release" describes the release window for certain formulations of the present disclosure formulated to increase the release period to a maximum value, which is ultimately limited by the time the gastrointestinal tract naturally excretes all drugs with food.

The language "tamper resistance" is art-recognized to describe aspects of a drug formulation that make it more difficult to use the formulation to abuse the drug moiety of the formulation through extraction for intravenous use, or crushing for freebase use; and therefore reduce the risk for abuse of the drug.

As used herein, the term "steady" describes the stable or steady-state level of a molecule concentration, e.g., concentration of any compound described herein.

As used herein, the term "composition" is equivalent to the term "formulation." As used herein, the language "administration event" describes the administration of a subject a given dose, in the form of one or more pills within a short window of time, e.g., less than 10 minutes.

As used herein, the language "release period" describes the time window in which any compound described herein is released from the matrix to afford plasma concentrations of compounds described herein. The start time of the release period is defined from the point of oral administration to a subject, which is considered nearly equivalent to entry into the stomach, and initial dissolution by gastric enzymes and acid.

The term "treating" or "treatment" as used herein means the treating or treatment of a disease or medical condition in a patient, such as a mammal (particularly a human) that includes: ameliorating the disease or medical condition, such as, eliminating or causing regression of the disease or medical condition in a patient; suppressing the disease or medical condition, for example by, slowing or arresting the development of the disease or medical condition in a patient; or alleviating a symptom of the disease or medical condition in a patient. In some embodiments, prophylactic treatment can result in preventing the disease or medical condition from occurring, in a subject.

"Patient" refers to human and non-human subjects, especially mammalian subjects.

As used herein, and unless otherwise specified, the terms "prevent," "preventing" and "prevention" refer to the prevention of the onset, recurrence or spread of a disease, disorder, or condition, or of one or more symptoms thereof. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the term "managing" encompasses treating a subject who had suffered from the particular disease, disorder, or condition in an attempt to prevent or minimize the recurrence of the disease, disorder, or condition.

"Pharmaceutically effective amount" and "therapeutically effective amount" refer to an amount of a compound sufficient to treat a specified disorder or disease or one or more of its symptoms and/or to prevent the occurrence of the disease or disorder.

As used herein, and unless otherwise specified, a "prophylactically effective amount" of an active agent, is an amount sufficient to prevent a disease, disorder, or condition, or prevent its recurrence. The term "prophylactically effective amount" can encompass an amount that improves overall prophylaxis or enhances the prophylactic efficacy of another prophylactic agent.

The language "neurologically toxic spikes" is used herein to describe spikes in concentration of any compound described herein that would produce side-effects of sedation or psychotomimetic effects, e.g., hallucination, dizziness, and nausea; which can not only have immediate repercussions, but also effect treatment compliance. In particular, side effects may become more pronounced at blood concentration levels above 300 ng/L.

As used herein, and unless otherwise specified, a "neuropsychiatric disease or disorder" is a behavioral or psychological problem associated with a known neurological condition, and typically defined as a cluster of symptoms that co-exist. Examples of neuropsychiatric disorders include, but are not limited to, schizophrenia, cognitive deficits in schizophrenia, attention deficit disorder, attention deficit hyperactivity disorder, bipolar and manic disorders, depression or any combinations thereof.

"Inflammatory conditions or inflammatory disease," as used herein, refers broadly to chronic or acute inflammatory diseases. Inflammatory conditions and inflammatory diseases, include but are not limited to rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), and vascular stent restenosis; ocular diseases including uveitis, corneal disease, iritis, iridocyclitis, and cataracts.

As used herein, the term "and/or" includes any and all combinations of one or more of the associated listed items. As used in the description herein and throughout the claims that follow, the meaning of "a", "a", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

Compounds

The inventors have identified novel 2C—X type phenethylamine compounds that demonstrate preferential binding to G-protein coupled receptors (GPCRs), e.g., 5-HT$_2$ receptors, that are bioavailable (e.g., orally bioavailable), are distributed to the brain, have improved exposure (i.e., prevention of high drug concentrations (spiking) observed acutely after administration), and that possess advantageous enzymatic degradation profiles and clearance. As a result, the disclosed compounds have reduced side effects and/or toxicity, reduced interpatient variability, fast onset, and are relatively short acting, thereby enabling practical use in clinical settings. In addition to oral administration routes, these novel compounds may also possess properties, such as desirable lipophilicity, which enable their administration via inhalation or through transdermal routes, e.g., in the form of a transdermal patch. The novel 2C—X compounds are based on specific molecular modifications involving e.g., deuteration and/or fluorination to slow or shunt enzymatic degradation at specific sites, and in many cases introducing/maintaining metabolic soft spots at other sites-modifications which have been identified only after significant studies.

Formula (I)

Disclosed herein is a compound according to Formula (I):

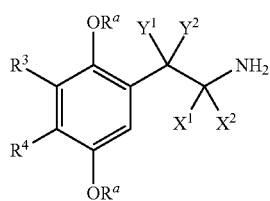

(I)

or a pharmaceutically acceptable salt, solvate, stereoisomer, or prodrug thereof, wherein:

$X^1$ and $X^2$ are independently hydrogen or deuterium;

$Y^1$ and $Y^2$ are independently hydrogen or deuterium;

$R^3$ is hydrogen or deuterium;

$R^4$ is halogen, a substituted or unsubstituted $C_1$-$C_6$ alkyl, a substituted or unsubstituted $C_3$-$C_{10}$ cycloalkyl, —OR$^b$, or —SR$^b$;

each $R^a$ is independently a substituted or unsubstituted $C_1$-$C_6$ alkyl; and $R^b$ is hydrogen, deuterium, a substituted or unsubstituted $C_1$-$C_6$ alkyl, or a substituted or unsubstituted $C_3$-$C_{10}$ cycloalkyl;

with the proviso that at least one of $X^1$, $X^2$, $Y^1$, $Y^2$, $R^3$, $R^4$, and $R^a$, comprises deuterium and/or $R^4$ is selected from the group consisting of —SCF$_3$, —SCH$_2$CH$_2$CF$_3$, —SCH$_2$CH$_2$CF$_2$H, —SCH$_2$CH$_2$CFH$_2$, —OCH$_2$CH$_2$CF$_3$, —OCH$_2$CH$_2$CF$_2$H, and —OCH$_2$CH$_2$CFH$_2$.

$X^1$ and $X^2$ may be the same, or different. In some embodiments, $X^1$ and $X^2$ are the same. In some embodiments, $X^1$ and $X^2$ are hydrogen. In some embodiments, $X^1$ and $X^2$ are deuterium.

$Y^1$ and $Y^2$ may be the same, or different. In some embodiments, $Y^1$ and $Y^2$ are the same. In some embodiments, $Y^1$ and $Y^2$ are hydrogen. In some embodiments, $Y^1$ and $Y^2$ are deuterium.

In some embodiments, $R^3$ is deuterium. In some embodiments, $R^3$ is hydrogen.

In some embodiments, $R^4$ is halogen, for example —Br, —F, —Cl, or —I.

In some embodiments, $R^4$ is a substituted or unsubstituted $C_1$-$C_6$ alkyl. In some embodiments, $R^4$ is an unsubstituted $C_1$-$C_6$ alkyl, examples of which include, but are not limited to, methyl, ethyl, n-propyl, isopropyl, n-butyl, isobutyl, sec-butyl, t-butyl, n-pentyl, neopentyl, and hexyl. Preferred unsubstituted alkyl groups are methyl and t-butyl. In some embodiments, $R^4$ is a substituted $C_1$-$C_6$ alkyl. Preferred substituents may include, but are not limited to, deuterium, halogen (e.g., fluorine), polar substituents such as hydroxyl or polyether substituents, etc. The alkyl group may contain one, or more than one, substituent. For example, when the alkyl group is a $C_1$ alkyl group (i.e., methyl group), the substituted $C_1$ alkyl group may be —CDH$_2$, —CD$_2$H, —CD$_3$, —CFH$_2$, —CF$_2$H, —CF$_3$, etc.

In some embodiments, $R^4$ is a substituted or unsubstituted $C_3$-$C_{10}$ cycloalkyl. In some embodiments, $R^4$ is an unsubstituted $C_3$-$C_{10}$ cycloalkyl, examples of which may include, but are not limited to, adamantyl, cyclopropyl, cyclobutyl, cyclopentyl, cyclohexyl, and cyclooctyl. In some embodiments, $R^4$ is a substituted $C_3$-$C_{10}$ cycloalkyl. Preferred substituents may include, but are not limited to, alkyl, deuterium, halogen (e.g., fluorine), polar substituents such as hydroxyl or polyether substituents, etc. The cycloalkyl group may contain one, or more than one, substituent.

In some embodiments, $R^4$ is —OR$^b$, wherein $R^b$ is hydrogen, deuterium, a substituted or unsubstituted $C_1$-$C_6$ alkyl, or a substituted or unsubstituted $C_3$-$C_{10}$ cycloalkyl, preferably a substituted or unsubstituted $C_1$-$C_6$ alkyl, or a substituted or unsubstituted $C_3$-$C_{10}$ cycloalkyl, such as those substituted $C_1$-$C_6$ alkyl groups, unsubstituted $C_1$-$C_6$ alkyl groups, substituted $C_3$-$C_{10}$ cycloalkyl groups, or unsubstituted $C_3$-$C_{10}$ cycloalkyl groups defined and exemplified above.

In some embodiments, $R^4$ is —SR$^b$, wherein $R^b$ is hydrogen, deuterium, a substituted or unsubstituted $C_1$-$C_6$ alkyl, or a substituted or unsubstituted $C_3$-$C_{10}$ cycloalkyl, preferably a substituted or unsubstituted $C_1$-$C_6$ alkyl, or a substituted or unsubstituted $C_3$-$C_{10}$ cycloalkyl, such as those substituted $C_1$-$C_6$ alkyl groups, unsubstituted $C_1$-$C_6$ alkyl groups, substituted $C_3$-$C_{10}$ cycloalkyl groups, or unsubstituted $C_3$-$C_{10}$ cycloalkyl groups defined and exemplified above.

In some embodiments, $R^4$ is selected from the group consisting of —SMe, —SCD$_3$, —SCF$_3$, —SCH$_2$CH$_2$CF$_3$, —SCH$_2$CH$_2$CF$_2$H, —SCH$_2$CH$_2$CFH$_2$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, —OCH$_2$CH$_2$CF$_3$, —OCH$_2$CH$_2$CF$_2$H, —OCH$_2$CH$_2$CFH$_2$, —Cl, —I, or —Br. In some embodiments, $R^4$ is selected from the group consisting of —SMe, -Me, —OCD$_3$, —CF$_3$, -t-Bu, or -cyclopentyl. In some embodiments, $R^4$ is selected from the group consisting of —SCF$_3$, —SCH$_2$CH$_2$CF$_3$, —SCH$_2$CH$_2$CF$_2$H, —SCH$_2$CH$_2$CFH$_2$, —OCH$_2$CH$_2$CF$_3$, —OCH$_2$CH$_2$CF$_2$H, and —OCH$_2$CH$_2$CFH$_2$. When $R^4$ is —SCF$_3$, —SCH$_2$CH$_2$CF$_3$, —SCH$_2$CH$_2$CF$_2$H, —SCH$_2$CH$_2$CFH$_2$, —OCH$_2$CH$_2$CF$_3$, —OCH$_2$CH$_2$CF$_2$H, or —OCH$_2$CH$_2$CFH$_2$, the other substituents (i.e., $X^1$, $X^2$, $Y^1$, $Y^2$, $R^3$, and $R^a$) may, or may not, comprise deuterium.

Each $R^a$ may be the same, or different. In some embodiments, each $R^a$ is the same. Each $R^a$ may be, independently, a substituted or unsubstituted $C_1$-$C_6$ alkyl, preferably a substituted or unsubstituted $C_1$-$C_3$ alkyl, preferably a substituted or unsubstituted $C_1$ alkyl, examples of which include, but are not limited to, —CH$_3$, —CDH$_2$, —CD$_2$H, —CD$_3$, —CFH$_2$, —CF$_2$H, —CF$_3$. In some embodiments, each $R^a$ is —CH$_3$. In some embodiments, each $R^a$ is —CD$_3$. In some embodiments, each $R^a$ is different, e.g., one $R^a$ is —CH$_3$, while another is —CD$_3$.

In some embodiments, $Y^1$ and $Y^2$ are each hydrogen or each deuterium; $R^3$ is hydrogen; $X^1$ and $X^2$ are each hydrogen or each deuterium; each $R^a$ is —CH$_3$ or -CD$_3$; and $R^4$ is —SMe, —SCD$_3$, —SCF$_3$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, or —Br.

As stated above, any of the above embodiments of the compound of Formula (I) may be provided as long as at least one of $X^1$, $X^2$, $Y^1$, $Y^2$, $R^3$, $R^4$, and $R^a$, comprises deuterium and/or $R^4$ is selected from the group consisting of —SCF$_3$, —SCH$_2$CH$_2$CF$_3$, —SCH$_2$CH$_2$CF$_2$H, —SCH$_2$CH$_2$CFH$_2$, —OCH$_2$CH$_2$CF$_3$, —OCH$_2$CH$_2$CF$_2$H, and —OCH$_2$CH$_2$CFH$_2$.

Formula (II)

In some embodiments, the compound has a structure of formula (II):

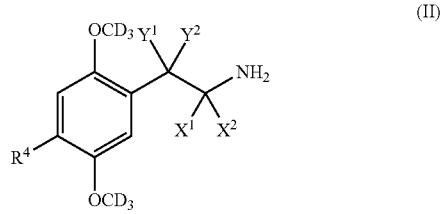

(II)

or a pharmaceutically acceptable salt, solvate, stereoisomer, or prodrug thereof, wherein:

$X^1$ and $X^2$ are independently hydrogen or deuterium;

$Y^1$ and $Y^2$ are independently hydrogen or deuterium;

$R^4$ is halogen, a substituted or unsubstituted $C_1$-$C_6$ alkyl, a substituted or unsubstituted $C_3$—$C_{10}$ cycloalkyl, —OR$^b$, or —SR$^b$; and $R^b$ is hydrogen, deuterium, a substituted or unsubstituted $C_1$-$C_6$ alkyl, or a substituted or unsubstituted $C_3$-$C_{10}$ cycloalkyl.

$X^1$ and $X^2$ may be the same, or different. In some embodiments, $X^1$ and $X^2$ are the same. In some embodiments, $X^1$ and $X^2$ are hydrogen. In some embodiments, $X^1$ and $X^2$ are deuterium.

$Y^1$ and $Y^2$ may be the same, or different. In some embodiments, $Y^1$ and $Y^2$ are the same. In some embodiments, $Y^1$ and $Y^2$ are hydrogen. In some embodiments, $Y^1$ and $Y^2$ are deuterium.

In some embodiments, $R^4$ is halogen, for example —Br, —F, —Cl, or —I.

In some embodiments, $R^4$ is a substituted or unsubstituted $C_1$-$C_6$ alkyl. In some embodiments, $R^4$ is an unsubstituted $C_1$-$C_6$ alkyl, examples of which include, but are not limited to, methyl, ethyl, n-propyl, isopropyl, n-butyl, isobutyl, sec-butyl, t-butyl, n-pentyl, neopentyl, and hexyl. Preferred unsubstituted alkyl groups are methyl and t-butyl. In some embodiments, $R^4$ is a substituted $C_1$-$C_6$ alkyl. Preferred substituents may include, but are not limited to, deuterium, halogen (e.g., fluorine), polar substituents such as hydroxyl or polyether substituents, etc. The alkyl group may contain one, or more than one, substituent. For example, when the alkyl group is a $C_1$ alkyl group (i.e., methyl group), the substituted $C_1$ alkyl group may be —CDH$_2$, —CD$_2$H, —CD$_3$, —CFH$_2$, —CF$_2$H, —CF$_3$, etc.

In some embodiments, $R^4$ is a substituted or unsubstituted $C_3$-$C_{10}$ cycloalkyl. In some embodiments, $R^4$ is an unsubstituted $C_3$-$C_{10}$ cycloalkyl, examples of which may include, but are not limited to, adamantyl, cyclopropyl, cyclobutyl, cyclopentyl, cyclohexyl, and cyclooctyl. In some embodiments, $R^4$ is a substituted $C_3$-$C_{10}$ cycloalkyl. Preferred substituents may include, but are not limited to, alkyl, deuterium, halogen (e.g., fluorine), polar substituents such as hydroxyl or polyether substituents, etc. The cycloalkyl group may contain one, or more than one, substituent.

In some embodiments, $R^4$ is —OR$^b$, wherein $R^b$ is hydrogen, deuterium, a substituted or unsubstituted $C_1$-$C_6$ alkyl, or a substituted or unsubstituted $C_3$-$C_{10}$ cycloalkyl, preferably a substituted or unsubstituted $C_1$-$C_6$ alkyl, or a substituted or unsubstituted $C_3$-$C_1$® cycloalkyl, such as those substituted $C_1$-$C_6$ alkyl groups, unsubstituted $C_1$-$C_6$ alkyl groups, substituted $C_3$-$C_{10}$ cycloalkyl groups, or unsubstituted $C_3$-$C_{10}$ cycloalkyl groups defined and exemplified above.

In some embodiments, $R^4$ is —SR$^b$, wherein $R^b$ is hydrogen, deuterium, a substituted or unsubstituted $C_1$-$C_6$ alkyl, or a substituted or unsubstituted $C_3$-$C_{10}$ cycloalkyl, preferably a substituted or unsubstituted $C_1$-$C_6$ alkyl, or a substituted or unsubstituted $C_3$-$C_{10}$ cycloalkyl, such as those substituted $C_1$-$C_6$ alkyl groups, unsubstituted $C_1$-$C_6$ alkyl groups, substituted $C_3$-$C_{10}$ cycloalkyl groups, or unsubstituted $C_3$-$C_{10}$ cycloalkyl groups defined and exemplified above.

In some embodiments, $R^4$ is selected from the group consisting of —SMe, —SCD$_3$, —SCF$_3$, —SCH$_2$CH$_2$CF$_3$, —SCH$_2$CH$_2$CF$_2$H, —SCH$_2$CH$_2$CFH$_2$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, —OCH$_2$CH$_2$CF$_3$, —OCH$_2$CH$_2$CF$_2$H, —OCH$_2$CH$_2$CFH$_2$, —Cl, —I, or —Br. In some embodiments, $R^4$ is selected from the group consisting of —SMe, -Me, —OCD$_3$, —CF$_3$, -t-Bu, or -cyclopentyl.

In some embodiments, $Y^1$ and $Y^2$ are each hydrogen or each deuterium, $X^1$ and $X^2$ are each hydrogen or each deuterium, and $R^4$ is —SMe, —SCD$_3$, —SCF$_3$, —SCH$_2$CH$_2$CF$_3$, —SCH$_2$CH$_2$CF$_2$H, —SCH$_2$CH$_2$CFH$_2$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, —OCH$_2$CH$_2$CF$_3$, —OCH$_2$CH$_2$CF$_2$H, —OCH$_2$CH$_2$CFH$_2$, —Cl, —I, or —Br, preferably $R^4$ is —SMe, -Me, —OCD$_3$, —CF$_3$, -t-Bu, or -cyclopentyl.

The compounds of Formula (II) containing deuteration in the form of —OCD$_3$ groups at the 2- and 5-position of the phenyl ring can have beneficial effects by slowing or shunting O-demethylation (primarily mediated by CYP2D6 enzymes) at these positions, thereby improving the pharmacokinetics, specifically the bioavailability, and safety as a result of lower exposure to toxic metabolites.

Formula (III)

In some embodiments, the compound has a structure of formula (III):

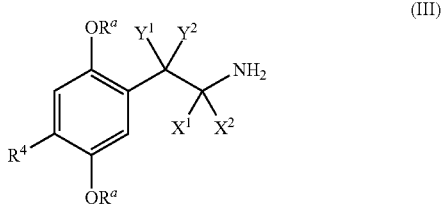

or a pharmaceutically acceptable salt, solvate, stereoisomer, or prodrug thereof, wherein:

$X^1$ and $X^2$ are independently hydrogen or deuterium;

$Y^1$ and $Y^2$ are independently hydrogen or deuterium;

$R^4$ is a $C_1$-$C_6$ alkyl substituted with one or more deuterium, a $C_3$-$C_{10}$ cycloalkyl substituted with one or more deuterium, —OR$^b$, or —SR$^b$;

each $R^a$ is independently a substituted or unsubstituted $C_1$-$C_6$ alkyl; and $R^b$ is a $C_1$-$C_6$ alkyl substituted with one or more deuterium or a $C_3$-$C_{10}$ cycloalkyl substituted with one or more deuterium.

$X^1$ and $X^2$ may be the same, or different. In some embodiments, $X^1$ and $X^2$ are the same. In some embodiments, $X^1$ and $X^2$ are hydrogen. In some embodiments, $X^1$ and $X^2$ are deuterium.

$Y^1$ and $Y^2$ may be the same, or different. In some embodiments, $Y^1$ and $Y^2$ are the same. In some embodiments, $Y^1$ and $Y^2$ are hydrogen. In some embodiments, $Y^1$ and $Y^2$ are deuterium.

In some embodiments, $R^4$ is a $C_1$-$C_6$ alkyl substituted with one or more deuterium, examples of which include, but are not limited to, methyl, ethyl, n-propyl, isopropyl, n-butyl, isobutyl, sec-butyl, t-butyl, n-pentyl, neopentyl, and hexyl groups containing one or more deuterium substitutions. The alkyl group may contain one, or more than one, deuterium substituent, such as 1, 2, 3, 4, 5, 6, 7, 8, or 9 deuterium substituents. Exemplary $C_1$-$C_6$ alkyl groups substituted with one or more deuterium include, but are not limited to, —CD$_3$ and —C(CD$_3$)$_3$.

In some embodiments, $R^4$ is a $C_3$-$C_{10}$ cycloalkyl substituted with one or more deuterium, for example, adamantyl, cyclopropyl, cyclobutyl, cyclopentyl, cyclohexyl, or cyclooctyl groups substituted with one or ore deuterium. The cycloalkyl group may contain one, or more than one, substituent, such as 1, 2, 3, 4, 5, 6, 7, 8, or 9 deuterium substituents.

In some embodiments, $R^4$ is —OR$^b$, wherein $R^b$ is a $C_1$-$C_6$ alkyl substituted with one or more deuterium, or a $C_3$-$C_{10}$ cycloalkyl substituted with one or more deuterium, such as those $C_1$-$C_6$ alkyl groups substituted with one or more deuterium or $C_3$-$C_{10}$ cycloalkyl groups substituted with one or more deuterium defined and exemplified above. In some embodiments, $R^4$ is —OCD$_3$.

In some embodiments, $R^4$ is —SR$^b$, wherein $R^b$ is a $C_1$-$C_6$ alkyl substituted with one or more deuterium, or a $C_3$-$C_{10}$ cycloalkyl substituted with one or more deuterium, such as those $C_1$-$C_6$ alkyl groups substituted with one or more deuterium or $C_3$-$C_{10}$ cycloalkyl groups substituted with one or more deuterium defined and exemplified above. In some embodiments, $R^4$ is —SCD$_3$.

In some embodiments, $R^4$ is selected from the group consisting of $R^4$ is —SCD$_3$, —CD$_3$, —C(CD$_3$)$_3$, and —OCD$_3$.

Each $R^a$ may be the same, or different. In some embodiments, each $R^a$ is the same. Each $R^a$ may be, independently, a substituted or unsubstituted $C_1$-$C_6$ alkyl, preferably a substituted or unsubstituted $C_1$-$C_3$ alkyl, preferably a substituted or unsubstituted $C_1$ alkyl, examples of which include, but are not limited to, —CH$_3$, —CDH$_2$, —CD$_2$H, —CD$_3$, —CFH$_2$, —CF$_2$H, —CF$_3$. In some embodiments, each $R^a$ is —CH$_3$. In some embodiments, each $R^a$ is —CD$_3$. In some embodiments, each $R^a$ is different, e.g., one $R^a$ is —CH$_3$, while another is —CD$_3$.

In some embodiments, $X^1$ and $X^2$ are each hydrogen or each deuterium, $Y^1$ and $Y^2$ are each hydrogen or each deuterium, each $R^a$ is —CH$_3$, and $R^4$ is —SCD$_3$, —CD$_3$, —C(CD$_3$)$_3$, or —OCD$_3$.

The compounds of Formula (III) containing deuterated alkyl/cycloalkyl groups in the $R^4$ position of the phenyl ring can have beneficial effects by allowing for the incorporation of lipophilic groups for improved brain penetrability, while at the same time slowing or shunting metabolism at this position, for improved pharmacokinetics, specifically bioavailability.

Formula (IV)

In some embodiments, the compound has a structure of formula (IV):

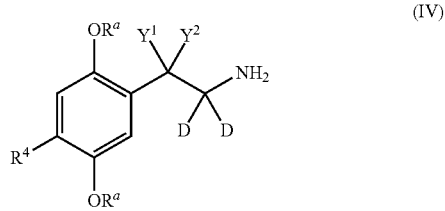

or a pharmaceutically acceptable salt, solvate, stereoisomer, or prodrug thereof, wherein:

$Y^1$ and $Y^2$ are independently hydrogen or deuterium;

$R^4$ is halogen, a substituted or unsubstituted $C_1$-$C_6$ alkyl, a substituted or unsubstituted $C_3$-$C_{10}$ cycloalkyl, —OR$^b$, or —SR$^b$;

each $R^a$ is independently a substituted or unsubstituted $C_1$-$C_6$ alkyl; and $R^b$ is hydrogen, deuterium, a substituted or unsubstituted $C_1$-$C_6$ alkyl, or a substituted or unsubstituted $C_3$-$C_{10}$ cycloalkyl.

$Y^1$ and $Y^2$ may be the same, or different. In some embodiments, $Y^1$ and $Y^2$ are the same.

In some embodiments, $Y^1$ and $Y^2$ are hydrogen. In some embodiments, $Y^1$ and $Y^2$ are deuterium.

In some embodiments, $R^4$ is halogen, for example —Br, —F, —Cl, or —I.

In some embodiments, $R^4$ is a substituted or unsubstituted $C_1$-$C_6$ alkyl. In some embodiments, $R^4$ is an unsubstituted $C_1$-$C_6$ alkyl, examples of which include, but are not limited to, methyl, ethyl, n-propyl, isopropyl, n-butyl, isobutyl, sec-butyl, t-butyl, n-pentyl, neopentyl, and hexyl. Preferred unsubstituted alkyl groups are methyl and t-butyl. In some embodiments, $R^4$ is a substituted $C_1$-$C_6$ alkyl. Preferred substituents may include, but are not limited to, deuterium, halogen (e.g., fluorine), polar substituents such as hydroxyl or polyether substituents, etc. The alkyl group may contain one, or more than one, substituent. For example, when the alkyl group is a $C_1$ alkyl group (i.e., methyl group), the substituted $C_1$ alkyl group may be —CDH$_2$, —CD$_2$H, —CD$_3$, —CFH$_2$, —CF$_2$H, —CF$_3$, etc.

In some embodiments, $R^4$ is a substituted or unsubstituted $C_3$-$C_{10}$ cycloalkyl. In some embodiments, $R^4$ is an unsubstituted $C_3$-$C_{10}$ cycloalkyl, examples of which may include, but are not limited to, adamantyl, cyclopropyl, cyclobutyl, cyclopentyl, cyclohexyl, and cyclooctyl. In some embodiments, $R^4$ is a substituted $C_3$-$C_{10}$ cycloalkyl. Preferred substituents may include, but are not limited to, alkyl, deuterium, halogen (e.g., fluorine), polar substituents such as hydroxyl or polyether substituents, etc. The cycloalkyl group may contain one, or more than one, substituent.

In some embodiments, $R^4$ is —$OR^b$, wherein $R^b$ is hydrogen, deuterium, a substituted or unsubstituted $C_1$-$C_6$ alkyl, or a substituted or unsubstituted $C_3$-$C_{10}$ cycloalkyl, preferably a substituted or unsubstituted $C_1$-$C_6$ alkyl, or a substituted or unsubstituted $C_3$-$C_{10}$ cycloalkyl, such as those substituted $C_1$-$C_6$ alkyl groups, unsubstituted $C_1$-$C_6$ alkyl groups, substituted $C_3$-$C_{10}$ cycloalkyl groups, or unsubstituted $C_3$-$C_{10}$ cycloalkyl groups defined and exemplified above.

In some embodiments, $R^4$ is —$SR^b$, wherein $R^b$ is hydrogen, deuterium, a substituted or unsubstituted $C_1$-$C_6$ alkyl, or a substituted or unsubstituted $C_3$-$C_{10}$ cycloalkyl, preferably a substituted or unsubstituted $C_1$-$C_6$ alkyl, or a substituted or unsubstituted $C_3$-$C_{10}$ cycloalkyl, such as those substituted $C_1$-$C_6$ alkyl groups, unsubstituted $C_1$-$C_6$ alkyl groups, substituted $C_3$-$C_{10}$ cycloalkyl groups, or unsubstituted $C_3$-$C_{10}$ cycloalkyl groups defined and exemplified above.

In some embodiments, $R^4$ is selected from the group consisting of —SMe, —SCD$_3$, —SCF$_3$, —SCH$_2$CH$_2$CF$_3$, —SCH$_2$CH$_2$CF$_2$H, —SCH$_2$CH$_2$CFH$_2$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, —OCH$_2$CH$_2$CF$_3$, —OCH$_2$CH$_2$CF$_2$H, —OCH$_2$CH$_2$CFH$_2$, —Cl, —I, or —Br. In some embodiments, $R^4$ is selected from the group consisting of —SMe, -Me, —OCD$_3$, —CF$_3$, -t-Bu, or -cyclopentyl.

Each $R^a$ may be the same, or different. In some embodiments, each $R^a$ is the same. Each $R^a$ may be, independently, a substituted or unsubstituted $C_1$-$C_6$ alkyl, preferably a substituted or unsubstituted $C_1$-$C_3$ alkyl, preferably a substituted or unsubstituted $C_1$ alkyl, examples of which include, but are not limited to, —CH$_3$, —CDH$_2$, —CD$_2$H, —CD$_3$, —CFH$_2$, —CF$_2$H, —CF$_3$. In some embodiments, each $R^a$ is —CH$_3$. In some embodiments, each $R^a$ is —CD$_3$. In some embodiments, each $R^a$ is different, e.g., one $R^a$ is —CH$_3$, while another is —CD$_3$.

In some embodiments, $Y^1$ and $Y^2$ are each hydrogen or each deuterium, each $R^a$ is —CH$_3$ or -CD$_3$; and $R^4$ is —SMe, —SCD$_3$, —SCF$_3$, —SEt, —Sn—Pr, -Me, —CD$_3$, —CF$_3$, -t-Bu, —C(CD$_3$)$_3$, -cyclopentyl, —OMe, —OCD$_3$, —OCF$_3$, or —Br.

The compounds of Formula (IV) containing deuteration in the ethylene fragment that links the amino group with the benzene ring in phenethylamines, e.g., α-carbon deuteration, may advantageously slow enzymatic degradation compared to compounds which may otherwise be susceptible to MAO mediated deamination/oxidation processes, thereby improving bioavailability as well as enhancing brain levels of the active compound, with the objective to effectively reduce therapeutic doses and to prevent high drug concentrations ("spiking") observed acutely after administration. As a result, such compounds may result in reduced side effects and toxicity, such as acute adverse effects, including anxiety, fear, tachycardia, hypertension, increased body temperature, nausea and vomiting, as well as toxicity caused by activation of 5-HT$_{2B}$ receptors associated with valvular heart disease.

The compounds of Formulas (I) through (IV) may contain a stereogenic center. In such cases, the compounds may exist as different stereoisomeric forms, even though Formulas (I) through (IV) are drawn without reference to stereochemistry. Accordingly, the present disclosure includes all possible stereoisomers and includes not only racemic compounds but the individual enantiomers (enantiomerically pure compounds) and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

In some embodiments, the compounds described herein, e.g., compounds of Formulas (I) through (IV), are racemic. In some embodiments, the compounds described herein, e.g., compounds of Formulas (I) through (IV), are enantiomerically pure.

In some embodiments, the compound is an agonist of a serotonin 5-HT$_2$ receptor.

In some embodiments, the compound can be an agonist of a serotonin 5-HT$_{2A}$ receptor.

In some embodiments, the compound, e.g., the compound of Formulas (I) through (IV) is selected from the group consisting of:

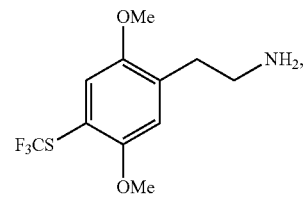

(I-1)

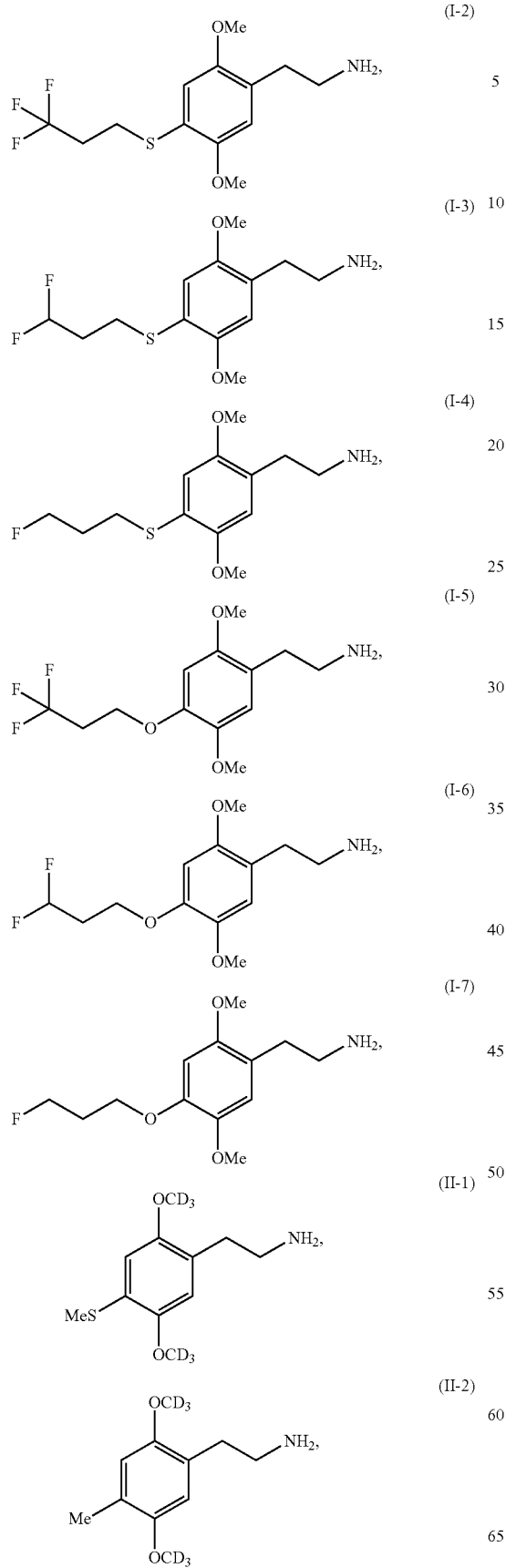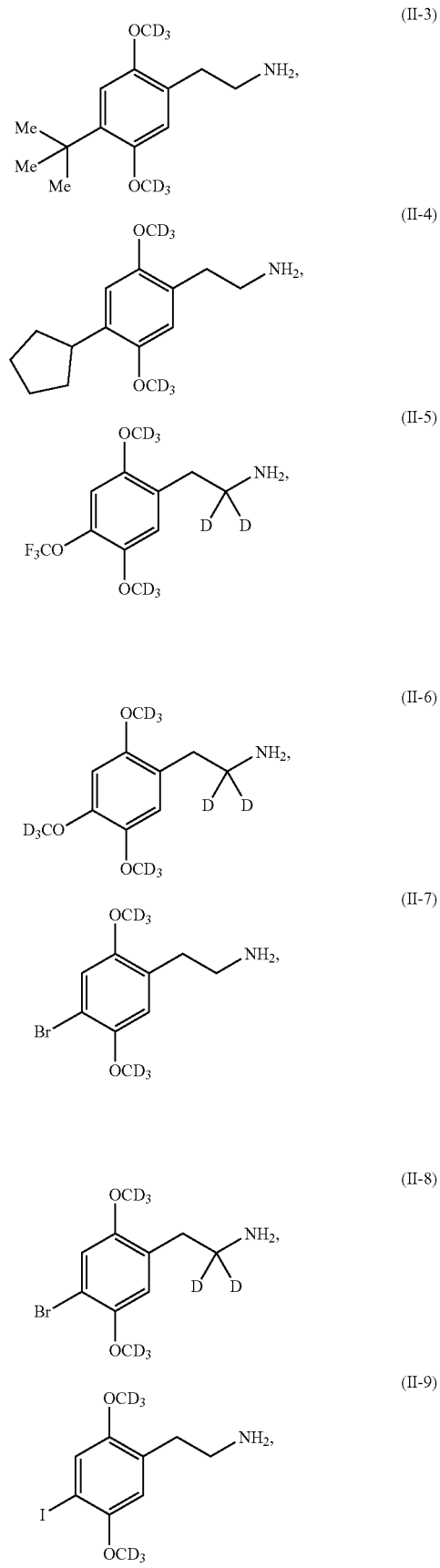

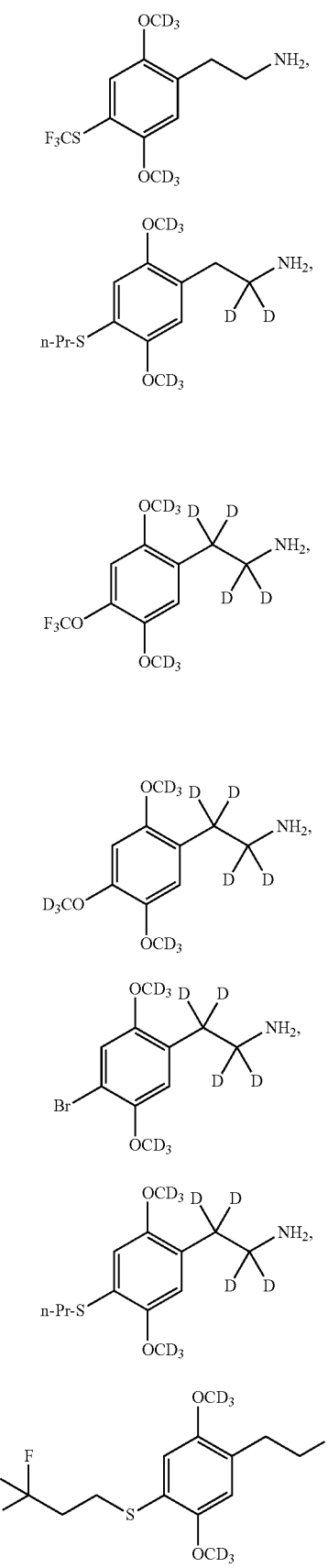
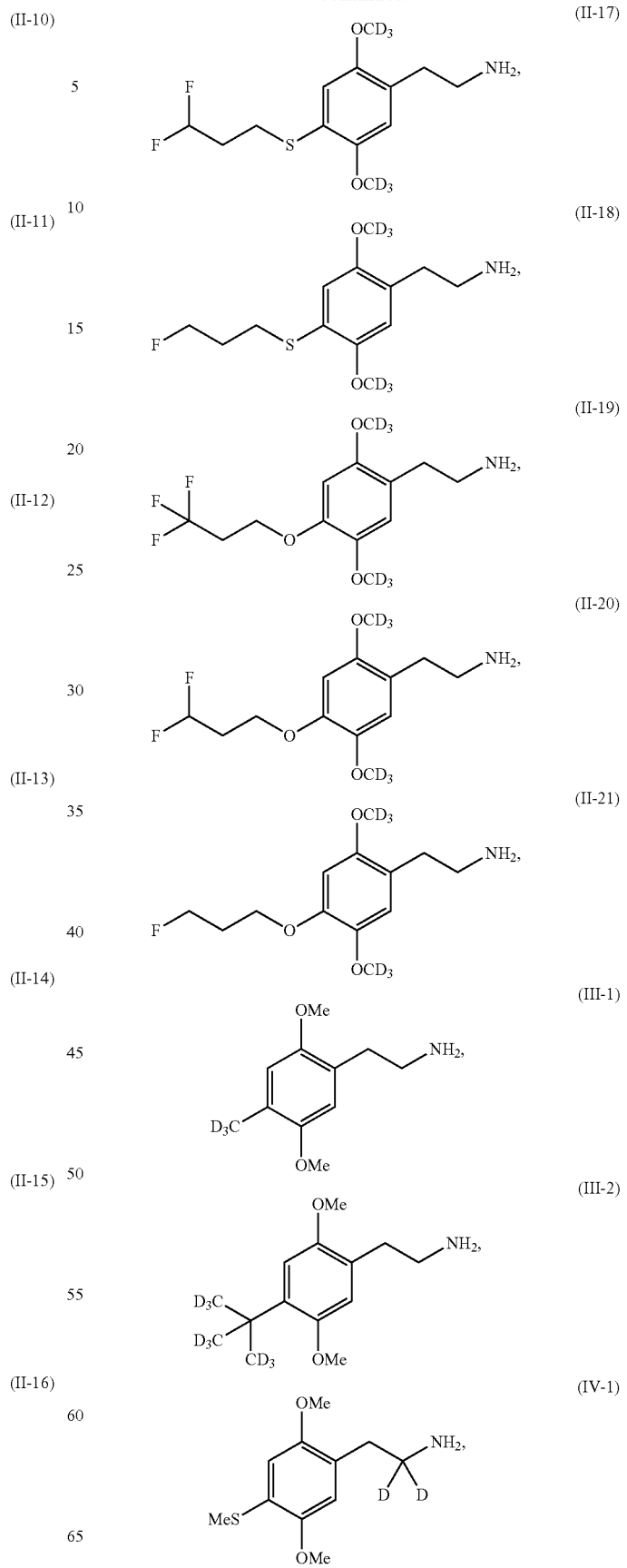

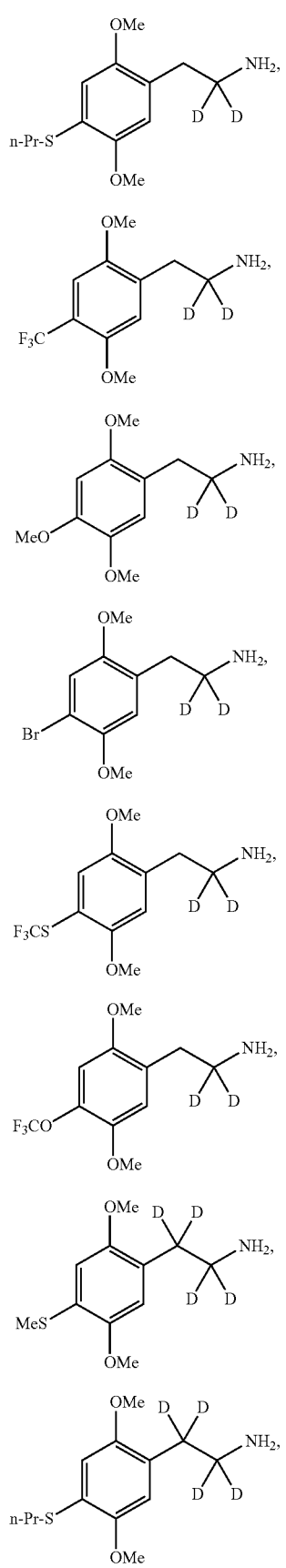
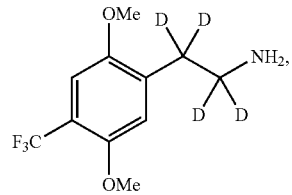
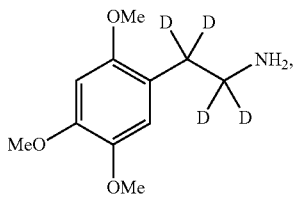
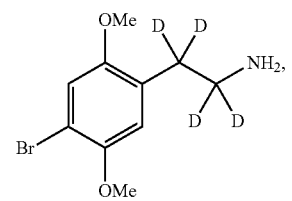
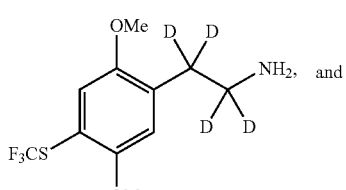
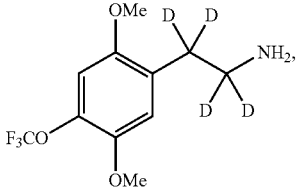
or a pharmaceutically acceptable salt, solvate, or pro drug thereof.
The compound number, IUPAC name, and substituent listing for the above-identified compounds are provided in Table 1.

TABLE 1

Exemplary compounds of Formula (I)

| Compound number and name | | $X^1, X^2$ | $Y^1, Y^2$ | $R^3$ | $R^4$ | $R^a, R^a$ |
|---|---|---|---|---|---|---|
| I-1 | 2-(2,5-dimethoxy-4-((trifluoromethyl)thio)phenyl)ethan-1-amine | H, H | H, H | H | —SCF$_3$ | —Me, —Me, |
| I-2 | 2-(2,5-dimethoxy-4-((3,3,3-trifluoropropyl)thio)phenyl)ethan-1-amine | H, H | H, H | H | —SCH$_2$CH$_2$CF$_3$ | —Me, —Me, |
| I-3 | 2-(4-((3,3-difluoropropyl)thio)-2,5-dimethoxyphenyl)ethan-1-amine | H, H | H, H | H | —SCH$_2$CH$_2$CF$_2$H | —Me, —Me, |
| I-4 | 2-(4-((3-fluoropropyl)thio)-2,5-dimethoxyphenyl)ethan-1-amine | H, H | H, H | H | —SCH$_2$CH$_2$CFH$_2$ | —Me, —Me, |
| I-5 | 2-(2,5-dimethoxy-4-(3,3,3-trifluoropropoxy)phenyl)ethan-1-amine | H, H | H, H | H | —OCH$_2$CH$_2$CF$_3$ | —Me, —Me, |
| I-6 | 2-(4-(3,3-difluoropropoxy)-2,5-dimethoxyphenyl)ethan-1-amine | H, H | H, H | H | —OCH$_2$CH$_2$CF$_2$H | —Me, —Me, |
| I-7 | 2-(4-(3-fluoropropoxy)-2,5-dimethoxyphenyl)ethan-1-amine | H, H | H, H | H | —OCH$_2$CH$_2$CFH$_2$ | —Me, —Me, |
| II-1 | 2-(2,5-bis(methoxy-d3)-4-(methylthio)phenyl)ethan-1-amine | H, H | H, H | H | —SMe | —CD$_3$, —CD$_3$ |
| II-2 | 2-(2,5-bis(methoxy-d3)-4-methylphenyl)ethan-1-amine | H, H | H, H | H | —Me | —CD$_3$, —CD$_3$ |
| II-3 | 2-(4-(tert-butyl)-2,5-bis(methoxy-d3)phenyl)ethan-1-amine | H, H | H, H | H | —t-Bu | —CD$_3$, —CD$_3$ |
| II-4 | 2-(4-cyclopentyl-2,5-bis(methoxy-d3)phenyl)ethan-1-amine | H, H | H, H | H | —C$_5$H$_9$ | —CD$_3$, —CD$_3$ |
| II-5 | 2-(2,5-bis(methoxy-d3)-4-(trifluoromethoxy)phenyl)ethan-1,1-d2-1-amine | D, D | H, H | H | —OCF$_3$ | —CD$_3$, —CD$_3$ |
| II-6 | 2-(2,4,5-tris(methoxy-d3)phenyl)ethan-1,1-d2-1-amine | D, D | H, H | H | —OCD$_3$ | —CD$_3$, —CD$_3$ |
| II-7 | 2-(4-bromo-2,5-bis(methoxy-d3)phenyl)ethan-1-amine | H, H | H, H | H | —Br | —CD$_3$, —CD$_3$ |
| II-8 | 2-(4-bromo-2,5-bis(methoxy-d3)phenyl)ethan-1,1-d2-1-amine | D, D | H, H | H | —Br | —CD$_3$, —CD$_3$ |
| II-9 | 2-(4-iodo-2,5-bis(methoxy-d3)phenyl)ethan-1-amine | H, H | H, H | H | —I | —CD$_3$, —CD$_3$ |
| II-10 | 2-(2,5-bis(methoxy-d3)-4-((trifluoromethyl)thio)phenyl)ethan-1-amine | H, H | H, H | H | —SCF$_3$ | —CD$_3$, —CD$_3$ |
| II-11 | 2-(2,5-bis(methoxy-d3)-4-(propylthio)phenyl)ethan-a1,1-d2-1-mine | D, D | H, H | H | —S-n-Pr | —CD$_3$, —CD$_3$ |
| II-12 | 2-(2,5-bis(methoxy-d3)-4-(trifluoromethoxy)phenyl)ethan-1,1,2,2-d4-1-amine | D, D | D, D | H | —OCF$_3$ | —CD$_3$, —CD$_3$ |
| II-13 | 2-(2,4,5-tris(methoxy-d3)phenyl)ethan-1,1,2,2-d4-1-amine | D, D | D, D | H | —OCD$_3$ | —CD$_3$, —CD$_3$ |
| II-14 | 2-(4-bromo-2,5-bis(methoxy-d3)phenyl)ethan-1,1,2,2-d4-1-amine | D, D | D, D | H | —Br | —CD$_3$, —CD$_3$ |
| II-15 | 2-(2,5-bis(methoxy-d3)-4-(propylthio)phenyl)ethan-1,1,2,2-d4-1-amine | D, D | D, D | H | —S-n-Pr | —CD$_3$, —CD$_3$ |
| II-16 | 2-(2,5-bis(methoxy-d3)-4-((3,3,3-trifluoropropyl)thio)phenyl)ethan-1-amine | H, H | H, H | H | —SCH$_2$CH$_2$CF$_3$ | —CD$_3$, —CD$_3$ |
| II-17 | 2-(4-((3,3-difluoropropyl)thio)-2,5-bis(methoxy-d3)phenyl)ethan-1-amine | H, H | H, H | H | —SCH$_2$CH$_2$CF$_2$H | —CD$_3$, —CD$_3$ |
| II-18 | 2-(4-((3-fluoropropyl)thio)-2,5-bis(methoxy-d3)phenyl)ethan-1-amine | H, H | H, H | H | —SCH$_2$CH$_2$CFH$_2$ | —CD$_3$, -CD$_3$ |
| II-19 | 2-(2,5-bis(methoxy-d3)-4-(3,3,3-trifluoropropoxy)phenyl)ethan-1-amine | H, H | H, H | H | —OCH$_2$CH$_2$CF$_3$ | —CD$_3$, —CD$_3$ |
| II-20 | 2-(4-(3,3-difluoropropoxy)-2,5-bis(methoxy-d3)phenyl)ethan-1-amine | H, H | H, H | H | —OCH$_2$CH$_2$CF$_2$H | —CD$_3$ —CD$_3$ |
| II-21 | 2-(4-(3-fluoropropoxy)-2,5-bis(methoxy-d3)phenyl)ethan-1-amine | H, H | H, H | H | —OCH$_2$CH$_2$CFH$_2$ | —CD$_3$, —CD$_3$ |

TABLE 1-continued

Exemplary compounds of Formula (I)

| | | Formula (I) | | | | |
|---|---|---|---|---|---|---|
| Compound number and name | | $X^1, X^2$ | $Y^1, Y^2$ | $R^3$ | $R^4$ | $R^a, R^a$ |
| III-1 | 2-(2,5-dimethoxy-4-(methyl-d3)phenyl)ethan-1-amine | H, H | H, H | H | —$CD_3$ | —Me, —Me, |
| III-2 | 2-(2,5-dimethoxy-4-(2-(methyl-d3)propan-2-yl-1,1,1,3,3,3-d6)phenyl)ethan-1-amine | H, H | H, H | H | —$C(CD_3)_3$ | —Me, —Me, |
| IV-1 | 2-(2,5-dimethoxy-4-(methylthio)phenyl)ethan-1,1-d2-1-amine | D, D | H, H | H | —SMe | —Me, —Me, |
| IV-2 | 2-(2,5-dimethoxy-4-(propylthio)phenyl)ethan-1,1-d2-1-amine | D, D | H, H | H | —S-n-Pr | —Me, —Me, |
| IV-3 | 2-(2,5-dimethoxy-4-(trifluoromethyl)phenyl)ethan-1,1-d2-1-amine | D, D | H, H | H | —$CF_3$ | —Me, —Me, |
| IV-4 | 2-(2,4,5-trimethoxyphenyl)ethan-1,1-d2-1-amine | D, D | H, H | H | —OMe | —Me, —Me, |
| IV-5 | 2-(4-bromo-2,5-dimethoxyphenyl)ethan-1,1-d2-1-amine | D, D | H, H | H | —Br | —Me, —Me |
| IV-6 | 2-(2,5-dimethoxy-4-((trifluoromethyl)thio)phenyl)ethan-1,1-d2-1-amine | D, D | H, H | H | —$SCF_3$ | —Me, —Me, |
| IV-7 | 2-(2,5-dimethoxy-4-(trifluoromethoxy)phenyl)ethan-1,1-d2-1-amine | D, D | H, H | H | —$OCF_3$ | —Me, —Me, |
| IV-8 | 2-(2,5-dimethoxy-4-(methylthio)phenyl)ethan-1,1,2,2-d4-1-amine | D, D | D, D | H | —SMe | —Me, —Me, |
| IV-9 | 2-(2,5-dimethoxy-4-(propylthio)phenyl)ethan-1,1,2,2-d4-1-amine | D, D | D, D | H | —S-n-Pr | —Me, —Me, |
| IV-10 | 2-(2,5-dimethoxy-4-(trifluoromethyl)phenyl)ethan-1,1,2,2-d4-1-amine | D, D | D, D | H | —$CF_3$ | —Me, —Me |
| IV-11 | 2-(2,4,5-trimethoxyphenyl)ethan-1,1,2,2-d4-1-amine | D, D | D, D | H | —OMe | —Me, —Me |
| IV-12 | 2-(4-bromo-2,5-dimethoxyphenyl)ethan-1,1,2,2-d4-1-amine | D, D | D, D | H | —Br | —Me, —Me |
| IV-13 | 2-(2,5-dimethoxy-4-((trifluoromethyl)thio)phenyl)ethan-1,1,2,2-d4-1-amine | D, D | D, D | H | —$SCF_3$ | —Me, —Me |
| IV-14 | 2-(2,5-dimethoxy-4-(trifluoromethoxy)phenyl)ethan-1,1,2,2-d4-1-amine | D, D | D, D | H | —$OCF_3$ | —Me, —Me |

Therapeutic Applications and Methods

Also disclosed herein is a method of treating a subject with a disease or disorder comprising administering to the subject a therapeutically effective amount of a compound as disclosed herein (e.g., compounds of Formulas (I) through (IV)).

The dosage and frequency (single or multiple doses) of compounds administered can vary depending upon a variety of factors, including, but not limited to, the disease/condition being treated; route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response to the treatment and adjusting the dosage upwards or downwards.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

The administration schedule may be varied depending on the compound employed, the condition being treated, etc. For example, administration may be performed once a day (QD), or in divided dosages throughout the day, such as 2-times a day (BID), 3-times a day (TID), or 4-times a day (QID). In some embodiments administration may be performed nightly (QHS). In some embodiments, the compounds/pharmaceutical compositions may be administered as needed (PRN).

In some embodiments, the use of formulations of the disclosure may be used as a standalone therapy. In some embodiments, the use of formulations of the disclosure may be used as an adjuvant/combination therapy.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The subjects treated herein may have a disease or disorder associated with a serotonin 5-HT$_2$ receptor.

In some embodiments, the disease or disorder is a neuropsychiatric disease or disorder or an inflammatory disease or disorder. In some embodiments, the disease or disorder is selected from the group consisting of central nervous system (CNS) disorders, including post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction (e.g., low libido), chronic fatigue syndrome, Lyme disease, and obesity. In some embodiments, the disease or disorder may include conditions of the autonomic nervous system (ANS). In some embodiments, the disease or disorder may include pulmonary disorders (e.g., asthma and chronic obstructive pulmonary disorder (COPD). In some embodiments, the disease or disorder may include cardiovascular disorders (e.g., atherosclerosis).

In some embodiments, the disclosure provides for the management of different kinds of pain, including but not limited to cancer pain, e.g., refractory cancer pain; neuropathic pain; postoperative pain; opioid-induced hyperalgesia and opioid-related tolerance; neurologic pain; postoperative/post-surgical pain; complex regional pain syndrome (CRPS); shock; limb amputation; severe chemical or thermal burn injury; sprains, ligament tears, fractures, wounds and other tissue injuries; dental surgery, procedures and maladies; labor and delivery; during physical therapy; radiation poisoning; acquired immunodeficiency syndrome (AIDS); epidural (or peridural) fibrosis; orthopedic pain; back pain; failed back surgery and failed laminectomy; sciatica; painful sickle cell crisis; arthritis; autoimmune disease; intractable bladder pain; pain associated with certain viruses, e.g., shingles pain or herpes pain; acute nausea, e.g., pain that may be causing the nausea or the abdominal pain that frequently accompanies sever nausea; migraine, e.g., with aura; and other conditions including depression (e.g., acute depression or chronic depression), depression along with pain, alcohol dependence, acute agitation, refractory asthma, acute asthma (e.g., unrelated pain conditions can induce asthma), epilepsy, acute brain injury and stroke, Alzheimer's disease and other disorders. The pain may be persistent or chronic pain that lasts for weeks to years, in some cases even though the injury or illness that caused the pain has healed or gone away, and in some cases despite previous medication and/or treatment. In addition, the disclosure includes the treatment/management of any combination of these types of pain or conditions.

In some embodiments, the pain treated/managed is acute breakthrough pain or pain related to wind-up that can occur in a chronic pain condition. In some embodiments of the disclosure, the pain treated/managed is cancer pain, e.g., refractory cancer pain. In some embodiments of the disclosure, the pain treated/managed is post-surgical pain. In some embodiments of the disclosure, the pain treated/managed is orthopedic pain. In some embodiments of the disclosure, the pain treated/managed is back pain. In some embodiments of the disclosure, the pain treated/managed is neuropathic pain. In some embodiments of the disclosure, the pain treated/managed is dental pain.

In some embodiments of the disclosure, the condition treated/managed is depression. In some embodiments of the disclosure, the pain treated/managed is chronic pain in opioid-tolerant patients.

In some embodiments, the disclosure provides for the management of sexual dysfunction, which may include, but is not limited to, sexual desire disorders, for example, decreased libido; sexual arousal disorders, for example, those causing lack of desire, lack of arousal, pain during intercourse, and orgasm disorders such as anorgasmia; and erectile dysfunction; particularly sexual dysfunction disorders stemming from psychological factors.

In embodiments, the disclosure relates to a method of treating a disease or condition by modulating N-methyl-D-aspartic acid (NMDA) activity, where the method comprises administering an effective amount of any of the compounds described herein (e.g., any of the compounds described herein (e.g., compounds of Formulas (I) through (IV)) to a subject in need thereof. In embodiments, the disease or condition is selected from: levodopa-induced dyskinesia; dementia (e.g., Alzheimer's dementia), tinnitus, treatment resistant depression (TRD), major depressive disorder, neuropathic pain, agitation resulting from or associated with Alzheimer's disease, pseudobulbar effect, autism, Bulbar function, generalized anxiety disorder, Alzheimer's disease, schizophrenia, diabetic neuropathy, acute pain, depression, bipolar depression, suicidality, neuropathic pain, or post-traumatic stress disorder (PTSD). In embodiments, the disease or condition is a psychiatric or mental disorder (e.g., schizophrenia, mood disorder, substance induced psychosis, major depressive disorder (MDD), bipolar disorder, bipolar depression (BDep), post-traumatic stress disorder (PTSD), suicidal ideation, anxiety, obsessive compulsive disorder (OCD), and treatment-resistant depression (TRD)). In other embodiments, the disease or condition is a neurological disorder (e.g., Huntington's disease (HD), Alzheimer's disease (AD), or systemic lupus erythematosus (SLE)).

For example, in some embodiments, the disclosure provides a method of treating a subject with any of the compounds described herein (e.g., compounds of Formulas (I) through (IV)), or a pharmaceutically acceptable salt thereof, comprising the step of administering to a subject an orally administered tablet composition, e.g., matrix composition, of the disclosure comprising any of the compounds described herein (e.g., compounds of Formulas (I) through (IV)), or a pharmaceutically acceptable salt thereof, such that the subject is treated.

The administering physician can provide a method of treatment that is prophylactic or therapeutic by adjusting the amount and timing of any of the compounds described herein (e.g., compounds of Formulas (I) through (IV)), or a pharmaceutically acceptable salt thereof, on the basis of observations of one or more symptoms of the disorder or condition being treated.

In some embodiments of the disclosure, the subject is a mammal.

In some embodiments of the disclosure, the mammal is a human.

In some embodiments, the disclosure provides a method of continuous oral administration of any of the compounds described herein (e.g., compounds of Formulas (I) through (IV)), or a pharmaceutically acceptable salt thereof. Any of the compounds described herein (e.g., compounds of Formulas (I) through (IV)), or a pharmaceutically acceptable salt thereof, may be formulated into a tablet composition, e.g., single-layer tablet, that provides a steady release of a therapeutically effective concentration of the compound over a complete release period without neurologically toxic spikes, e.g., no sedative or psychotomimetic toxic spikes in plasma concentration of any of the compounds described herein (e.g., compounds of Formulas (I) through (IV)), or a pharmaceutically acceptable salt thereof. The tablet composition may be orally administered to a subject, such that a continuous therapeutically effective concentration of any of the compounds described herein (e.g., compounds of Formulas (I) through (IV)), or a pharmaceutically acceptable salt thereof, is provided to the subject.

Compounds of the present disclosure possess advantageous metabolic degradation profiles which prevent high drug concentrations observed acutely after administration, while also enhancing brain levels of the active compound, so that in some embodiments the therapeutic doses may be reduced. As a result, the compounds may be suitable for microdosing to achieve durable therapeutic benefits, with decreased toxicity, e.g., toxicity associated with activation of 5-HT2a receptors associated with valvular heart disease (Rothman, R. B., and Baumann, M. H., 2009, Serotonergic drugs and valvular heart disease, *Expert Opin Drug Saf* 8, 317-329).

Pharmaceutical Compositions

Also disclosed herein is a pharmaceutical composition comprising a compound as disclosed herein (e.g., compounds of Formulas (I) through (IV)) and a pharmaceutically acceptable excipient.

The compound may be present in the pharmaceutical composition at a purity of at least 50% by weight, at least 60% by weight, at least 70% by weight, at least 80% by weight, at least 90% by weight, at least 95% by weight, at least 99% by weight, based on a total weight of isotopologues of the compound present in the pharmaceutical composition. In preferred compounds and compositions, any position in the compound having deuterium has a minimum deuterium incorporation of at least 10 atom %, at least 20 atom %, at least 25 atom %, at least 30 atom %, at least 40 atom %, at least 45 atom %, at least 50 atom %, at least 60 atom %, at least 70 atom %, at least 80 atom %, at least 90 atom %, at least 95 atom %, at least 99 atom % at the site of deuteration. In preferred embodiments, the composition is substantially free of other isotopologues of the compound, e.g. the composition has less than 20, 15, 10, 9, 8, 7, 6, 5, 4, 3, 2 or 1 or 0.5 mole percent of other isotopologues of the compound.

The pharmaceutical composition may be formulated with an enantiomerically pure compound of the present disclosure, e.g., a compound of Formulas (I) through (IV), or a racemic mixture of the compounds. As described herein, a racemic compound of Formulas (I) through (IV) may contain about 50% of the R- and S-stereoisomers based on a molar ratio (about 48 to about 52 mol %, or about a 1:1 ratio)) of one of the isomers. In some embodiments, a composition, medicament, or method of treatment may involve combining separately produced compounds of the R- and S-stereoisomers in an approximately equal molar ratio (about 48 to 52%). In some embodiments, a medicament or pharmaceutical composition may contain a mixture of separate compounds of the R- and S-stereoisomers in different ratios. In some embodiments, the pharmaceutical composition contains an excess (greater than 50%) of the R-enantiomer. Suitable molar ratios of R/S may be from about 1.5:1, 2:1, 3:1, 4:1, 5:1, 10:1, or higher. In some embodiments, a pharmaceutical composition may contain an excess of the S-enantiomer, with the ratios provided for R/S reversed. Other suitable amounts of R/S may be selected. For example, the R-enantiomer may be present in amounts of at least about 55% to 100%, or at least 65%, at least 75%, at least 80%, at least 85%, at least 90%, about 95%, about 98%, or 100%. In other embodiments, the S-enantiomer may be present in a higher percentage, e.g., in amounts of at least about 55% to 100%, or at least 65%, at least 75%, at least 80%, at least 85%, at least 90%, about 95%, about 98%, or 100%. Ratios between all these exemplary embodiments as well as greater than and less than them while still within the disclosure, all are included. Compositions may contain a mixture of the racemate and a separate compound of Formulas (I) through (IV), in free base and/or in salt form.

The term "excipient" refers to a diluent, adjuvant, vehicle, or carrier with which a compound of the present disclosure is formulated for administration to a mammal. "Pharmaceutically acceptable excipients" may be those diluents, adjuvants, vehicles, or carriers approved by a regulatory agency of the Federal or a state government or listed in the U.S. Pharmacopeia or other generally recognized pharmacopeia for use in mammals, such as humans. Such pharmaceutically acceptable excipients can be solids or liquids, such as water and oils, including those of petroleum, animal, vegetable or synthetic origin, such as peanut oil, soybean oil, mineral oil, sesame oil and the like. The pharmaceutically acceptable excipient can be saline, gum acacia, gelatin, starch paste, talc, keratin, colloidal silica, urea, and the like. In addition, auxiliary, stabilizing, disintegrating, thickening, lubricating, flavorants, buffers, and coloring agents may be used.

When administered to a mammal, the compounds and compositions of the present disclosure may be sterile. In some instances, an aqueous medium is employed as a vehicle when the subject compound is administered intravenously or via inhalation, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments, administration to a mammal will result in systemic release of a compound of the present disclosure (for example, into the bloodstream). Methods of administration may include enteral routes, such as oral, buccal, sublingual, and rectal; topical administration, such as transdermal (e.g., using skin patch formulations of the compounds herein) and intradermal; administration by inhalation via, for example a nebulizer or inhaler, and parenteral administration (e.g., via injection). In addition to intravenous injection, other injectable administration routes may include, but are not limited to transdermal, subcutaneous, and intramuscular administration, for example, using an automatic injection device. In some preferred embodiments, the pharmaceutical composition herein is formulated for oral administration. In some preferred embodiments, the pharmaceutical composition herein is formulated for administration via inhalation. In some preferred embodiments, the pharmaceutical composition herein is formulated in the form of a skin patch for transdermal administration.

In some embodiments, the pharmaceutical composition includes a compound of the present disclosure, and a polymer. In some embodiments, the pharmaceutical composition includes: (i) a water-insoluble neutrally charged non-ionic matrix; and (ii) a polymer carrying one or more negatively charged groups.

In some embodiments, the water-insoluble neutrally charged non-ionic matrix is selected from cellulose-based polymers such as HPMC, alone or enhanced by mixing with components selected from the group consisting of starches; waxes; neutral gums; polymethacrylates; PVA; PVA/PVP blends; and mixtures thereof. In some embodiments, the cellulose-based polymer is hydroxypropyl methylcellulose (HPMC).

In some embodiments, the polymer carrying one or more negatively charged groups is selected from the group consisting of polyacrylic acid, polylactic acid, polyglycolic acid, polymethacrylate carboxylates, cation-exchange resins, clays, zeolites, hyaluronic acid, anionic gums, salts thereof, and mixtures thereof.

In some embodiments, the anionic gum is a naturally occurring material or a semi-synthetic material. In some embodiments, the naturally occurring material is selected from the group consisting of alginic acid, pectin, xanthan gum, carrageenan, locust bean gum, gum arabic, gum karaya, guar gum, and gum tragacanth. In some embodiments, the semi-synthetic material is selected from the group consisting of carboxymethyl-chitin and cellulose gum.

In some embodiments, provided is a modified release oral formulation. In some embodiments, the oral formulation is for low dose maintenance therapy that can be constructed using the compounds described herein, capitalizing on the ability of the phenethylamine-type compounds described herein to bind with anionic polymers.

In some embodiments, the formulation contains a compound of the present disclosure, which is an orally active, peripherally-restricted, 5-$HT_2$ agonist, for the treatment of autonomic nervous system disorders, including pulmonary disorders (e.g., asthma) and cardiovascular disorders (e.g., atherosclerosis).

The pharmaceutical composition may be prepared and administered in a wide variety of dosage formulations. Compounds described may be administered orally, topically (cream or patch), rectally, via inhalation, or by injection (e.g. intravenously, intramuscularly, intracutaneously, subcutaneously, intraduodenally, or intraperitoneally). In some embodiments, the compounds described herein may be administered via an automatic injection device.

Automatic injection devices offer a method for delivery of the compositions disclosed herein to patients. The compositions disclosed herein may be administered to a patient using automatic injection devices through a number of known devices, a non-limiting list of which includes transdermal, subcutaneous, and intramuscular delivery.

In some transdermal, subcutaneous, or intramuscular applications, a composition disclosed herein is absorbed through the skin. Passive transdermal patch devices often include an absorbent layer or membrane that is placed on the outer layer of the skin. The membrane typically contains a dose of a substance that is allowed to be absorbed through the skin to deliver the composition to the patient. Typically, only substances that are readily absorbed through the outer layer of the skin may be delivered with such transdermal patch devices.

Other automatic injection devices disclosed herein are configured to provide for increased skin permeability to improve delivery of the disclosed compositions. Non-limiting examples of structures used to increase permeability to improve transfer of a composition into the skin, across the skin, or intramuscularly include the use of one or more microneedles, which in some embodiments may be coated with a composition disclosed herein. Alternatively, hollow microneedles may be used to provide a fluid channel for delivery of the disclosed compositions below the outer layer of the skin. Other devices disclosed herein include transdermal delivery by iontophoresis, sonophoresis, reverse iontophoresis, or combinations thereof, and other technologies known in the art to increase skin permeability to facilitate drug delivery.

For preparing pharmaceutical compositions from compounds described herein, pharmaceutically acceptable excipients can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets can contain from about 5% to about 70% by weight, or from about 10% to about 60% by weight, or from about 20% to about 50% by weight, or from about 30% to about 40% by weight of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A pharmaceutical preparation can be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted e.g., from 0.001 mg to 100 mg, or 0.001 mg to 75 mg, or 0.001 mg to 50 mg, or 0.001 mg to 25 mg, or 0.001 mg to 10 mg, or 0.01 mg to 8 mg, or 0.1 mg to 5 mg, or 1 mg to 3 mg, or otherwise as deemed appropriate using sound medical judgment, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

Tablet compositions (e.g., single-layer orally administered tablet composition)

Also disclosed herein are tablet compositions—pharmaceutical compositions formulated for oral administration—such as pills, capsules, caplets, troaches, lozenges, caches, gelcaps, caps, pellets, boluses, pastilles, orally disintegrating tablets, sublingual tablets and buccal tablets, e.g., single-layer tablet compositions, comprising any of the compounds described herein (e.g., compounds of Formulas (I) through (IV)), or a pharmaceutically acceptable salt thereof. The pharmaceutical composition may be formulated to ensure the steady release of a therapeutically effective concentration of the compounds described herein without sedative or psychotomimetic toxic spikes in plasma concentration. Such spikes in plasma concentration have been well-documented to have serious psychotomimetic directed side effects including, but not limited to hallucination, dizziness, and nausea; which can not only have immediate repercussions, but also adversely affect treatment compliance. In this regard, the disclosure provides novel and inventive formulations for oral administration comprising, e.g., optimal matrices discovered for the long-term steady release of any of the compounds of Formulas (I) through (IV) or a pharmaceutically acceptable salt thereof, with reduced sedative and psychotomimetic side effects.

In some embodiments, the pharmaceutical composition (e.g., a tablet composition formulated for oral administration such as a single-layer tablet composition), comprises any of the compounds described herein (e.g., compounds of Formulas (I) through (IV)), or a pharmaceutically acceptable salt thereof, and a polymer.

In some embodiments of the disclosure, the tablet composition is a modified-release tablet adapted for sustained release and preferably maximum sustained release.

In some embodiments of the disclosure, the tablet composition is adapted for tamper resistance. In some embodiments, the tablet composition comprises polyethylene oxide (PEO), e.g., MW about 2,000 to about 7,000 KDa, in combination with HPMC. In some embodiments, the tablet composition may further comprise polyethylene glycol (PEG), e.g., PEG 8K. In some embodiments, the tablet composition may further comprise a polymer carrying one or more negatively charged groups, e.g., polyacrylic acid. In specific embodiments, the tablet composition comprising PEO is further subjected to heating/annealing, e.g., extrusion conditions.

In some embodiments of the disclosure, the pharmaceutical composition comprises a combination of (i) a water-insoluble neutrally charged non-ionic matrix; (ii) a polymer carrying one or more negatively charged groups; and (iii) any of the compounds described herein (e.g., compounds of Formulas (I) through (IV)), or a pharmaceutically acceptable salt thereof.

In some embodiments of the disclosure, the polymer carrying one or more negatively charged groups is selected from the group consisting of polyacrylic acid, polylactic acid, polyglycolic acid, polymethacrylate carboxylates, cation-exchange resins, clays, zeolites, hyaluronic acid, anionic gums, salts thereof, and mixtures thereof. In some embodiments, the anionic gum is selected from the group consisting of naturally occurring materials and semi-synthetic materials. In some embodiments, the naturally occurring material is selected from the group consisting of alginic acid, pectin, xanthan gum, carrageenan, locust bean gum, gum arabic, gum karaya, guar gum, and gum tragacanth. In another specific embodiment, the semi-synthetic material is selected from the group consisting of carboxymethyl-chitin and cellulose gum.

Moreover, without wishing to be bound by theory, in some embodiments, the role of the polymer carrying one or more negatively charged groups, e.g., moieties of acidic nature as in those of the acidic polymers described herein, surprisingly offers significant retention of any of the compounds described herein (e.g., compounds of Formulas (I) through (IV)), or a pharmaceutically acceptable salt thereof, in the matrix. In some embodiments, this negative charge may be created in situ, for example, based on release of a proton due to pKa and under certain pH conditions or through electrostatic interaction/creation of negative charge. Further noting that acidic polymers may be the salts of the corresponding weak acids that will be the related protonated acids in the stomach; which, and without wishing to be bound by theory, will neutralize the charge and may reduce the interactions of any of the compounds described herein (e.g., compounds of Formulas (I) through (IV)), or a pharmaceutically acceptable salt thereof, with the matrix. In addition, the release matrix may be further complemented by other inactive pharmaceutical ingredients to aid in preparation of the appropriate solid dose form such as fillers, disintegrants, flow improving agents, lubricants, colorants, taste maskers, In some embodiments of the disclosure, the tablet composition is adapted for tamper resistance. In some embodiments, the tablet composition comprises polyethylene oxide (PEO), e.g., MW about 2,000 to about 7,000 KDa. In specific embodiments, the tablet composition comprising PEO is further subjected to heating/annealing, e.g., extrusion.

In some embodiments of the disclosure, the non-ionic matrix is selected from cellulose-based polymers such as HPMC, alone or enhanced by mixing with components selected from the group consisting of starches; waxes; neutral gums; polymethacrylates; PVA; PVA/PVP blends; and mixtures thereof.

In some embodiments of the disclosure, the cellulose-based polymer is hydroxypropyl methylcellulose (HPMC). In some embodiments, the tablet composition comprises about 20 to 60%, or 30 to 50% hydroxypropyl methylcellulose by weight, about 10 to 30%, or about 15 to 20% starch by weight, or any combination thereof.

In some embodiments, the tablet composition comprises a therapeutically effective amount of any of the compounds described herein for the treatment of pain. In some embodiments, the pain treated is cancer pain, e.g., refractory cancer pain. In some embodiments, the pain treated is post-surgical pain. In some embodiments, the pain treated is orthopedic pain. In some embodiments, the pain treated is back pain. In some embodiments, the pain treated is neuropathic pain. In some embodiments, the pain treated is dental pain. In some embodiments, the pain treated is chronic pain. In some embodiments, the pain treated is chronic pain in opioid-tolerant patients.

In some embodiments, the tablet composition comprises a therapeutically effective amount of any of the compounds described herein for the treatment of depression.

In some embodiments, the tablet composition comprises a therapeutically effective amount of any of the compounds described herein for the treatment of brain injury.

In some embodiments, the tablet composition comprises a therapeutically effective amount of any of the compounds described herein for the treatment of stroke.

In some embodiments, the tablet composition comprises a therapeutically effective amount of any of the compounds described herein for use in migraine, e.g., with aura.

In some embodiments, the tablet composition comprises a therapeutically effective amount of any of the compounds described herein for use in refractory asthma.

In some embodiments, the tablet composition comprises a therapeutically effective amount of any of the compounds described herein for use in treating alcohol dependence.

In some embodiments, the tablet composition comprises a therapeutically effective amount of any of the compounds described herein for use in treating post traumatic stress disorder (PTSD).

In some embodiments, the tablet composition comprises a therapeutically effective amount of any of the compounds described herein for use in treating depression (e.g., treatment resistant depression (TRD) or bipolar depression).

In some embodiments, the tablet composition comprises a therapeutically effective amount of any of the compounds described herein for use in treating major depressive disorder (MDD).

In some embodiments, the tablet composition comprises a therapeutically effective amount of any of the compounds described herein for use in treating anxiety (e.g., generalized anxiety disorder).

In some embodiments, the tablet composition comprises a therapeutically effective amount of any of the compounds described herein for use in treating schizophrenia.

In some embodiments, the tablet composition comprises a therapeutically effective amount of any of the compounds described herein for use in treating bipolar disorder.

In some embodiments, the tablet composition comprises a therapeutically effective amount of any of the compounds described herein for use in treating suicidality or suicidal ideation.

In some embodiments, the tablet composition comprises a therapeutically effective amount of any of the compounds described herein for use in treating autism.

In some embodiments, the tablet composition comprises a therapeutically effective amount of any of the compounds described herein for use in treating diabetic neuropathy.

In some embodiments, the tablet composition comprises a therapeutically effective amount of any of the compounds described herein for use in treating neuropathic pain.

In some embodiments, the tablet composition comprises a therapeutically effective amount of any of the compounds described herein for use in treating acute pain (e.g., acute trauma pain).

In some embodiments, the tablet composition comprises a therapeutically effective amount of any of the compounds described herein for use in treating chronic pain.

In some embodiments, the tablet composition comprises a therapeutically effective amount of any of the compounds described herein for use in treating levodopa-induced dyskinesia.

In some embodiments, the tablet composition comprises a therapeutically effective amount of any of the compounds described herein for use in treating or modulating a pseudobulbar effect or Bulbar function.

In some embodiments, the tablet composition comprises a therapeutically effective amount of any of the compounds described herein for use in treating Alzheimer's disease or conditions associated with Alzheimer's disease (e.g., Alzheimer's dementia or Alzheimer's agitation).

In some embodiments, the tablet composition comprises a therapeutically effective amount of any of the compounds described herein for use in treating tinnitus.

In some embodiments, the tablet composition comprises a therapeutically effective amount of any of the compounds described herein for use in treating a disease or disorder associated with a serotonin 5-HT2 receptor.

In some embodiments, the disease or disorder is selected from the group consisting of central nervous system (CNS) disorders, including post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme disease, and obesity.

In some embodiments, the disease or disorder includes conditions of the autonomic nervous system (ANS).

In some embodiments, the disease or disorder includes pulmonary disorders including asthma and chronic obstructive pulmonary disorder (COPD).

In some embodiments, the disease or disorder includes cardiovascular disorders including atherosclerosis.

In some embodiments, the tablet composition comprises an amount of any of the compounds described herein released from the matrix with a rate 0.05-2 mg/kg/h over a period of 12-24 hours, e.g., 24 hours.

In some embodiments of the disclosure, the composition achieves a combined concentration of any of the compounds described herein (e.g., compounds of Formulas (I) through (IV)), or a pharmaceutically acceptable salt thereof, in plasma in the range of about 10-500 ng/ml, and maintains this concentration for duration of the release period. In some embodiments, the composition achieves a combined concentration of any of the compounds described herein (e.g., compounds of Formulas (I) through (IV)), or a pharmaceutically acceptable salt thereof, in plasma in the range of about 10-300 ng/ml, and maintains this concentration for duration of the release period. In some embodiments, the composition achieves a combined concentration of any of the compounds described herein (e.g., compounds of Formulas (I) through (IV)), or a pharmaceutically acceptable salt thereof, in plasma in the range of about 10-100 ng/ml, or about 50-100 ng/ml, and maintains this concentration for duration of the release period. In some embodiments, the composition achieves a combined concentration of any of the compounds described herein (e.g., compounds of Formulas (I) through (IV)), or a pharmaceutically acceptable salt thereof, in plasma in the range of about 10-20 ng/ml, and maintains this concentration for duration of the release period.

In some embodiments of the disclosure, the release period of any of the compounds described herein (e.g., compounds of Formulas (I) through (IV)), or a pharmaceutically acceptable salt thereof, in the formulations of the disclosure is greater than 4 hours.

In some embodiments of the disclosure, the release period of any of the compounds described herein (e.g., compounds of Formulas (I) through (IV)), or a pharmaceutically acceptable salt thereof, in the formulations of the disclosure is greater than about 8 hours.

In some embodiments of the disclosure, the release period of any of the compounds described herein (e.g., compounds of Formulas (I) through (IV)), or a pharmaceutically acceptable salt thereof, in the formulations of the disclosure is greater than about 12 hours.

In some embodiments of the disclosure, the release period of any of the compounds described herein (e.g., compounds of Formulas (I) through (IV)), or a pharmaceutically acceptable salt thereof, in the formulations of the disclosure is greater than about 16 hours.

In some embodiments of the disclosure, the release period of any of the compounds described herein (e.g., compounds of Formulas (I) through (IV)), or a pharmaceutically acceptable salt thereof, in the formulations of the disclosure is greater than about 20 hours.

In some embodiments of the disclosure, the release period of any of the compounds described herein (e.g., compounds of Formulas (I) through (IV)), or a pharmaceutically acceptable salt thereof, in the formulations of the disclosure is greater than or equal to about 24 hours.

In some embodiments of the disclosure, the release period of any of the compounds described herein (e.g., compounds of Formulas (I) through (IV)), or a pharmaceutically acceptable salt thereof, in the formulations of the disclosure is greater than or equal to about 28 hours.

In some embodiments of the disclosure, the release period of any of the compounds described herein (e.g., compounds of Formulas (I) through (IV)), or a pharmaceutically acceptable salt thereof, in the formulations of the disclosure is greater than or equal to about 32 hours.

In some embodiments of the disclosure, the release period of any of the compounds described herein (e.g., compounds of Formulas (I) through (IV)), or a pharmaceutically acceptable salt thereof, in the formulations of the disclosure is greater than or equal to about 36 hours.

In some embodiments of the disclosure, the release period of any of the compounds described herein (e.g., compounds of Formulas (I) through (IV)), or a pharmaceutically acceptable salt thereof, in the formulations of the disclosure is less than about 48 hours.

In some embodiments of the disclosure, the release period of any of the compounds described herein (e.g., compounds of Formulas (I) through (IV)), or a pharmaceutically acceptable salt thereof, in the formulations of the disclosure is less than about 36 hours.

In some embodiments of the disclosure, the tablet compositions of the disclosure are utilized as a 2-times a day (BID), 3-times a day (TID) or 4-times a day (QID) application. In some embodiments of the disclosure, the tablet compositions of the disclosure are utilized as a once a day (QD) application.

In some embodiments of the disclosure, the tablet compositions of the disclosure are utilized as a nightly (QHS) application.

In some embodiments of the disclosure, the tablet compositions of the disclosure are utilized as an as needed (PRN) application.

In some embodiments of the disclosure, the oral pharmaceutical compositions are enhanced. In some embodiments, due to the efficiency of administration, the pharmaceutical compositions may be formulated with less active compound (e.g., the compounds of Formula (I) through (IV), or pharmaceutically acceptable salts thereof) for treatment, and achieve the same effect as comparative oral tablets not described by the disclosure.

In some embodiments of the disclosure, the oral administration event, which provides the appropriate single unit dose, may comprise one single pill or multiple pills.

In addition, to protect the tablet from the acidic environment in the stomach and maintain a long-term release, various types of enteric coatings may be used in some embodiments.

In some embodiments of the disclosure, a single-layer tablet or caplet is coated with protective layers of inactive pharmaceutical ingredients to form a modified-release formulation, e.g., to ensure steady release of the drug from the matrix and avoid concentration bursts at the early release time points.

Some embodiments of the disclosure provide formulations of any of the compounds described herein (e.g., compounds of Formulas (I) through (IV)), or a pharmaceutically acceptable salt thereof as a modified-release formulation, that ensures the steady release of a therapeutically effective concentration of any of the compounds from such oral modified-release formulations, without sedative or psychotomimetic toxic spikes in plasma concentration of any of the compounds. This formulation comprises any of the compounds described herein (e.g., compounds of Formulas (I) through (IV)), or a pharmaceutically acceptable salt thereof, formulated in an osmotic controlled release pharmaceutical composition, such as a tablet, caplet or granules. In these formulations a single core layer containing any of the compounds described herein (e.g., compounds of Formulas (I) through (IV)), or a pharmaceutically acceptable salt thereof (e.g., as defined by other tablet formulations described herein), is surrounded by semi-permeable membrane with or without drug delivery orifice. Without wishing to be bound by theory, because these systems use water osmotic pressure for the controlled delivery of the active material, delivery rates are expected to be independent of gastrointestinal conditions. In combination with the novel and inventive aspects of the disclosure, osmotic asymmetric-membrane technology or AMT (e.g., technology directed to a single-layer tablet, caplet or granules coated with an insoluble, asymmetric microporous membrane produced by controlled phase separation) may be used to produce formulations useful in the methods of treatment and kits described herein.

In some embodiments of the disclosure, any of the compounds described herein may be formulated as a pharmaceutically acceptable salt thereof, e.g., hydrochloride, aspartate, succinate, etc., such that the counterion does not significantly affect formulation as described herein for any of the compounds described herein (e.g., compounds of Formulas (I) through (IV)), or the ability of any of the compounds to achieve the desired therapeutic effects, i.e., with similar steady release of a therapeutically effective concentration (e.g., based on indication) from an oral pharmaceutical composition, such as a tablet, a caplet, a capsule, a gelcap, a cap or granules, without sedative or psychotomimetic toxic spikes in the concentration of any of the compounds described herein (e.g., compounds of Formulas (I) through (IV)), or a pharmaceutically acceptable salt thereof.

Exemplary salts, within this scope, may include but are not limited to: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid, succinic acid, tartaric acid; and other mineral and carboxylic acids well known to those skilled in the art. Additional examples may include salts with inorganic cations such as sodium, potassium, calcium, magnesium, lithium, aluminum, zinc, etc; and salts formed with pharmaceutically acceptable amines such as ammonia, alkylamines, hydroxyalkylamines, lysine, arginine, N-methylglucamine, procaine and the like. In specific embodiments, the pharmaceutically acceptable salt is a hydrochloride salt.

General Tablet Formulations

The formulations of the disclosure comprise orally administered pharmaceutical compositions, such as tablet, capsule, caplets, gelcap and cap compositions, which may include uncoated tablets or coated tablets, caplets and caps (including film-coated, sugar-coated tablets, and gastro-resistant/enteric-coated tablets). The oral pharmaceutical compositions for oral use may include the active ingredients, e.g., any of the compounds described herein (e.g., compounds of Formulas (I) through (IV)), mixed with pharmaceutically acceptable inactive excipients such as diluents, disintegrating agents, binding agents, lubricating agents, powder flow improving agent, wetting agents, sweetening agents, flavoring agents, coloring agents and preservatives. Moreover, oral pharmaceutical compositions of the disclosure are solid dosage forms intended for oral administration, e.g., obtained by dry granulation with single or multiple compressions of powders or granules. In some embodiments, the oral pharmaceutical compositions may be obtained by using wet granulation techniques. In some embodiments, the oral pharmaceutical compositions may be obtained by molding, heating/annealing, or extrusion techniques.

In some embodiments, the oral tablets are right circular solid cylinders, the end surfaces of which are flat or convex, and the edges of which may be beveled. In some embodiments, the surfaces are convex. In addition, they may have lines or break-marks (scoring), symbols or other markings.

In some embodiments, the break-mark(s) is/are intended to permit accurate subdivision of the tablet in order to provide doses of less than one tablet. In some embodiments of the disclosure, the tablet compositions comprise one or more excipients such as diluents, binders, disintegrating agents, glidants, lubricants, substances capable of modifying the behavior of the dosage forms and the active ingredient(s) in the gastrointestinal tract, coloring matter authorized by the appropriate national or regional authority and flavoring substances. When such excipients are used it is necessary to ensure that they do not adversely affect the stability, dissolution rate, bioavailability, safety or efficacy of the active ingredient(s); there must be no incompatibility between any of the components of the dosage form.

Coated tablets are tablets covered with one or more layers of mixtures of substances such as natural or synthetic resins, polymers, gums, fillers, sugars, plasticizers, polyols, waxes, coloring matters authorized by the appropriate national or regional authority, and flavoring substances. Such coating materials do not contain any active ingredient, e.g., any of the compounds described herein (e.g., compounds of Formulas (I) through (IV)), or a pharmaceutically acceptable salt thereof. The tablets may be coated for a variety of reasons such as protection of the active ingredients from burst release from the matrix, air, moisture or light, masking of unpleasant tastes and odors or improvement of appearance. The substance used for coating may be applied as a solution or suspension.

In some embodiments, the manufacturing processes for the oral pharmaceutical compositions, e.g., tablets, meet the requirements of good manufacturing practices (GMP). In some embodiments, one or more measures are taken in the manufacture of oral pharmaceutical compositions selected from the following: ensure that mixing with excipients is carried out in a manner that ensures homogeneity; ensure that the oral pharmaceutical compositions possess a suitable mechanical strength to avoid crumbling or breaking on subsequent processing, e.g., coating, storage and distribution; minimize the degradation of the active ingredient; minimize the risk of microbial contamination; minimize the risk of cross-contamination. In addition, in the manufacture of scored tablets (tablets bearing a break-mark or marks) for which subdivision is intended in order to provide doses of less than one tablet measures are taken to: ensure the effectiveness of break-marks with respect to the uniformity of mass or content, as appropriate, of the subdivided parts so that the patient receives the intended close.

In general, a suitable dose will be in the range of about 0.01 to about 10 mg per kilogram body weight of the recipient per day, preferably in the range of about 0.1 to about 5 mg per kilogram body weight per day, preferably in the range of about 0.5 to about 3 mg per kilogram body weight per day, preferably in the range of about 1 to about 2 mg per kilogram body weight per day. Additional details on techniques for formulation and administration are well described in the scientific and patent literature, see, e.g., the latest edition of Remington's Pharmaceutical Sciences, Maack Publishing Co, Easton Pa. ("Remington's"). After a pharmaceutical composition has been formulated in an acceptable carrier, it can be placed in an appropriate container and labeled for treatment of an indicated condition. For administration of the formulations comprising any of the compounds described herein (e.g., compounds of Formulas (I) through (IV)), or a pharmaceutically acceptable salt thereof, such labeling would include, e.g., instructions concerning the amount, frequency, method of administration, treatment regimen and indications.

Kits

Some embodiments of the disclosure provides a kit for the treatment of a subject with any of the compounds described herein (e.g., compounds of Formulas (I) through (IV)), or a pharmaceutically acceptable salt thereof, comprising pharmaceutical composition, such as an orally administered pharmaceutical composition like a pill, of any one of the formulations described herein comprising any of the compounds described herein (e.g., compounds of Formulas (I) through (IV)), or a pharmaceutically acceptable salt thereof, and instructions for use in the treatment, prevention or management of a disease, disorder or condition, such as pain, e.g., as described herein.

In some embodiments of the disclosure, the pain treated is cancer pain, e.g., refractory cancer pain. In some embodiments of the disclosure, the pain treated is post-surgical pain. In some embodiments of the disclosure, the pain treated is orthopedic pain. In some embodiments of the disclosure, the pain treated is back pain. In some embodiments of the disclosure, the pain treated is neuropathic pain. In some embodiments of the disclosure, the pain treated is dental pain. In some embodiments of the disclosure, the pain treated is chronic pain. In some embodiments of the disclosure, the pain treated is chronic pain in opioid-tolerant patients.

In some embodiments, the disease or disorder is a disease or disorder associated with a serotonin 5-$HT_2$ receptor.

In some embodiments, the disease or disorder is selected from the group consisting of central nervous system (CNS) disorders, including post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme disease, and obesity. In some embodiments, the disease or disorder includes conditions of the autonomic nervous system (ANS).

In some embodiments, the disease or disorder includes pulmonary disorders including asthma and chronic obstructive pulmonary disorder (COPD).

In some embodiments, the disease or disorder includes cardiovascular disorders including atherosclerosis.

Some embodiments of the disclosure provides a kit for the treatment of a subject with any of the compounds described herein (e.g., compounds of Formulas (I) through (IV)), or a pharmaceutically acceptable salt thereof, comprising a pharmaceutical composition, such as an orally administered tablet pharmaceutical composition like a pill, of any one of the formulations of the disclosure comprising any of the compounds described herein (e.g., compounds of Formulas (I) through (IV)), or a pharmaceutically acceptable salt thereof, and instructions for use in the treatment of brain injury.

Some embodiments of the disclosure provides a kit for the treatment of a subject with any of the compounds described herein (e.g., compounds of Formulas (I) through (IV)), or a pharmaceutically acceptable salt thereof, comprising a pharmaceutical composition, such as an orally administered tablet pharmaceutical composition like a pill, of any one of the formulations of the disclosure comprising any of the compounds described herein (e.g., compounds of Formulas (I) through (IV)), or a pharmaceutically acceptable salt thereof, and instructions for use in the treatment of depression.

Some embodiments of the disclosure provides a kit for the treatment of a subject with any of the compounds described herein (e.g., compounds of Formulas (I) through (IV)), or a pharmaceutically acceptable salt thereof, comprising a pharmaceutical composition, such as an orally administered tablet pharmaceutical composition like a pill, of the formulations of the disclosure comprising any of the compounds described herein (e.g., compounds of Formulas (I) through (IV)), or a pharmaceutically acceptable salt thereof, and instructions for use in the treatment of migraine, e.g., with aura.

Some embodiments of the disclosure provides a kit for the treatment of a subject with any of the compounds described herein (e.g., compounds of Formulas (I) through (IV)), or a pharmaceutically acceptable salt thereof, comprising a pharmaceutical composition, such as an orally administered tablet pharmaceutical composition like a pill, of the disclosure comprising any of the compounds described herein (e.g., compounds of Formulas (I) through (IV)), or a pharmaceutically acceptable salt thereof, and instructions for use in the treatment of refractory asthma.

Some embodiments of the disclosure provides a kit for the treatment of a subject with any of the compounds described herein (e.g., compounds of Formulas (I) through (IV)), or a pharmaceutically acceptable salt thereof, comprising a pharmaceutical composition, such as an orally administered tablet pharmaceutical composition like a pill, of any one of the formulations of the disclosure comprising any of the compounds described herein (e.g., compounds of Formulas (I) through (IV)), or a pharmaceutically acceptable salt thereof, and instructions for use in the treatment of stroke.

Some embodiments of the disclosure provides a kit for the treatment of a subject with any of the compounds described herein (e.g., compounds of Formulas (I) through (IV)), or a pharmaceutically acceptable salt thereof, comprising a pharmaceutical composition, such as an orally administered tablet pharmaceutical composition like a pill, of any one of the formulations of the disclosure comprising any of the compounds described herein (e.g., compounds of Formulas (I) through (IV)), or a pharmaceutically acceptable salt thereof, and instructions for use in the treatment of alcohol dependence.

In some embodiments, the instructions for use form an integrated component of the packaging for the tablet composition.

In embodiments, the disclosure features an oral, modified-release pharmaceutical composition for oral administration to a subject for treating the subject diagnosed with, suffering from or susceptible to a disease, disorder or condition, such as those for which phenethylamine treatment may be indicated, considered or recommended, wherein the subject is in need of treatment with said oral, modified-release pharmaceutical composition, said oral, modified-release pharmaceutical composition comprising:
  (a) a drug selected from a group consisting of any of the compounds described herein (e.g., compounds of Formulas (I) through (IV)), or a pharmaceutically acceptable salt thereof in an effective amount for treating, preventing and/or managing the disease, disorder, or condition in the subject; and
  (b) a pharmaceutically acceptable excipient;
  whereby, upon oral administration of the modified-release pharmaceutical composition to the subject, a steady release of said drug from the modified-release pharmaceutical composition is maintained so that no neurologically toxic spike in the subject's plasma occurs during the release period of said drug from said pharmaceutical composition.

Compliance with Monographs

In some embodiments, the formulations of the disclosure conform to certain industry accepted monographs to afford compliance with the Federal Food Drug and Cosmetic Act. In particular, the formulations of the disclosure conform and are considered acceptable under visual inspection, uniformity of mass analysis, uniformity of content analysis, and/or dissolution/disintegration analysis all of which are established by a relevant monograph.

In some embodiments, throughout manufacturing certain procedures are validated and monitored by carrying out appropriate in-process controls. These are designed to guarantee the effectiveness of each stage of production. In-process controls during tablet production may include the moisture content of the final lubricated blend, the size of granules, the flow of the final mixture and, where relevant, the uniformity of mass of tablet cores before coating. In-process controls during tablet production may also include the dimensions (thickness, diameter), uniformity of mass, hardness and/or crushing force, friability, disintegration or dissolution rate (for example, for modified-release tablets) of the finished dosage form. Suitable test methods that may be used to demonstrate certain of these attributes are known in the art.

In some embodiments, packaging maybe or is required to be adequate to protect the pharmaceutical compositions, including tablets, from light, moisture and damage during transportation.

In additional embodiments, the commercially available formulation (e.g., kit) complies with the labeling requirements established under Good Manufacturing Practices (GMP). Such label includes:
  (1) the name of the pharmaceutical product;
  (2) the name(s) of the active ingredient(s); International Nonproprietary Names (INN) should be used wherever possible;
  (3) the amount of the active ingredient(s) in each tablet and the number of tablets in the container;
  (4) the batch (lot) number assigned by the manufacturer;
  (5) the expiry date and, when required, the date of manufacture;
  (6) any special storage conditions or handling precautions that may be necessary;
  (7) directions for use, warnings, and precautions that may be necessary;
  (8) the name and address of the manufacturer or the person responsible for placing the product on the market;
  (9) for scored tablets where the directions for use include subdivision to provide doses of less than one tablet, the label should also include: the storage conditions for and the period of use of those subdivided part(s) not immediately taken or administered.

In some embodiments, the pharmaceutical compositions, e.g., tablets, can withstand handling, including packaging and transportation, without losing their integrity.

In some embodiments, the disclosure provides a method of formulating any of the compounds described herein (e.g., compounds of Formulas (I) through (IV)), or a pharmaceutically acceptable salt thereof, to ensure the steady release of a therapeutically effective concentration of any of the compounds from an oral tablet without neurologically toxic spikes, e.g., sedative or psychotomimetic toxic spikes, in plasma concentration of any of the compounds.

In some embodiments, the method comprises the step of combining (i) a water-insoluble neutrally charged non-ionic matrix; (ii) a polymer carrying one or more negatively charged groups; and (iii) any of the compounds described herein (e.g., compounds of Formulas (I) through (IV)), or a pharmaceutically acceptable salt thereof, to produce an orally administered tablet composition, e.g., single-layer. In some embodiments, the method comprises the step of combining (i) polyethylene oxide (PEO), e.g., MW about 2,000 to about 7,000 KDa, with HPMC, and (ii) any of the compounds described herein (e.g., compounds of Formulas (I) through (IV)), or a pharmaceutically acceptable salt thereof, to produce an orally administered tablet composition, e.g., single-layer. In some embodiments, the method comprises the step of combining polyethylene oxide (PEO) with HPMC, and any of the compounds described herein (e.g., compounds of Formulas (I) through (IV)), or a pharmaceutically acceptable salt thereof, the tablet composition may further comprise polyethylene glycol (PEG), e.g., PEG 8K, a polymer carrying one or more negatively charged groups, e.g., polyacrylic acid and/or may be further subjected to heating/annealing, e.g., extrusion conditions. In some embodiments, the formulations of the disclosure may be administered in combination with other active therapeutic agents, e.g., opioids to reduce pain. In some embodiments, the formulations of the disclosure serve the purpose of an opioid-sparing medication, i.e., to reduce the amount of opioids necessary to treat a patient.

In some embodiments, the formulations of the disclosure are not administered in combination with other active therapeutic agents.

In some embodiments, the formulations of the disclosure may be administered in combination with another formulation of phenethylamine or derivatives thereof, e.g., a fast release formulation of phenethylamine or derivatives thereof.

In some embodiments, the disclosure provides a method of formulating any of the compounds described herein (e.g., compounds of Formulas (I) through (IV)), or a pharmaceutically acceptable salt thereof, to ensure the steady release of a therapeutically effective concentration of any of the compounds from an oral tablet without sedative or psychotomimetic toxic spikes in plasma concentration of any of the compounds. The method comprises formulation of any of the compounds described herein (e.g., compounds of Formulas (I) through (IV)), or a pharmaceutically acceptable salt thereof, in an osmotic controlled release tablet. In these formulations the single core layer containing any of the compounds described herein (e.g., compounds of Formulas (I) through (IV)), or a pharmaceutically acceptable salt thereof, is surrounded by semi-permeable membrane with or without drug delivery orifice. In some embodiments, combination with the novel and inventive pharmaceutical compositions (e.g., containing any of the compounds described herein (e.g., compounds of Formulas (I) through (IV)), of the disclosure and osmotic asymmetric-membrane technology or AMT (e.g., technology directed to a single-layer tablet coated with an insoluble, asymmetric microporous membrane produced by controlled phase separation) may be used to produce formulations useful in the methods and kits described herein.

Inhalation Administration

Also disclosed herein are methods for mist inhalation administration of psychedelic drugs. Good aqueous solubility of most psychedelics including e.g., DMT (in the salt form) makes inhalation of a mist a possible route of administration.

Psychedelic drugs that can be used for mist inhalation administration include the compounds described herein (e.g., compounds of Formulas (I) through (IV)), or a pharmaceutically acceptable salt thereof.

Dosage of the psychedelic drugs (including the compounds described herein, e.g., compounds of Formulas (I) through (IV), or a pharmaceutically acceptable salt thereof), can vary. A pharmaceutical composition can include compositions wherein the psychedelic drug is contained in a therapeutically effective amount. An "effective amount" or a "therapeutically effective amount" is a sufficient amount of the drug to treat or ameliorate a condition, disorder, or disease. The actual amount effective for a particular application can depend, inter alia, on the condition being treated. The dosage and frequency (single or multiple doses) of psychedelic drug administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans can be determined, e.g., from animal models. For example, a dose for humans can be formulated to achieve a concentration that has been found to be effective in animals. The dosage in humans can be adjusted by monitoring response of the human to the treatment and adjusting the dosage upwards or downwards.

Dosages can be varied depending upon the requirements of the subject and the psychedelic drug being used. The dose administered to a subject, in the context of the psychedelic drugs presented herein, should be sufficient to induce a beneficial therapeutic response in the subject over time. The size of the dose also will be determined by the existence, nature, and extent of any adverse side effects. Treatment can be initiated with smaller dosages, which are less than the optimum dose of the psychedelic drug. Thereafter, the dosage can be increased by small increments until the optimum effect under the circumstances is reached.

Dosage amounts and intervals can be adjusted individually to provide levels of the administered compounds effective for the clinical indication being treated. This will provide a therapeutic regimen that is commensurate with the severity of the individual's disease state.

An effective prophylactic or therapeutic treatment regimen can be planned that does not cause substantial toxicity and yet is entirely effective to treat the clinical symptoms demonstrated by the patient. This planning can involve the choice of psychedelic drug by considering factors such as compound potency, relative bioavailability, patient body weight, presence and severity of adverse side effects, mode of administration, and the toxicity profile of the selected psychedelic drug.

Psychedelic drugs can be administered via mist inhalation at about 1 µg to about 10.0 mg or more (or any range between about 1 µg to about 10.0 mg), e.g., about 1 µg, 2 µg, 5 µg, 6 µg, 10 µg, 13 µg, 15 µg, 20 µg, 30 µg, 40 µg, 50 µg, 60 µg, 7 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 300 µg, 400 µg, 500 µg, 1.0 mg, 2.0 mg, 3.0 mg, 4.0 mg, 5.0 mg, 6.0 mg, 7.0 mg, 8.0 mg, 9.0 mg, 10.0 mg or more per inhalation session. In some embodiments a subject can have about 1, 2, 3, 4, 5 or more inhalation sessions a day. In some embodiments a subject can have about 1, 2, 3, 4, 5 or more inhalation sessions every other day, twice a week, or three times a week.

In some embodiments a subject can have about 1, 2, 3, 4, 5 or more inhalation sessions every other month, twice a month, three times a month, or four times a month.

A pharmaceutical composition comprising a psychedelic drug can be prepared and administered in a wide variety of dosage formulations. Liquid form preparations include solutions and emulsions, for example, water, water/propylene glycol solutions, or organic solvents.

Aqueous solutions suitable for inhalation use can be prepared by dissolving the active psychedelic drug or derivative thereof in water. Suitable stabilizers and thickening agents can also be added. Aqueous emulsions suitable for inhalation use can be made by dispersing the liquid psychedelic drug or derivative thereof in water with viscous material, such as natural or synthetic gums, resins, methylcellulose, sodium carboxymethylcellulose, and other suspending agents.

Some psychedelic drugs can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of an emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

In the salt form, psychedelic drugs or derivatives thereof can also be dissolved in organic solvents. Organic solvents can be, for example, acetonitrile, chlorobenzene, chloroform, cyclohexane, 1,2-dichloromethane, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methybutylketone, methylcyclohexane, N-methylpyrrolidone, nitromethane, pyridine, sulfolane, tetralin, toluene, 1,1,2-trichloroethylene, or xylene. Organic solvents can belong to functional group categories such as ester solvents, ketone solvents, alcohol solvents, amide solvents, ether solvents, hydrocarbon solvents, etc. each of which can be used.

Mists

In some embodiments, methods of delivering psychedelic drugs by mist inhalation are provided. A mist can be delivered using air, oxygen, and/or oxygen and helium mixtures. The air, oxygen, and/or oxygen and helium mixture can be delivered at room temperature or heated. In some embodiments, a mist comprising a psychedelic drug or derivative thereof is delivered via inhalation using heated helium-oxygen (HELIOX) mixtures. Due to very low viscosity of helium, the helium-oxygen mixtures generate gaseous streams characterized by laminar flow that is a highly desirable feature for reaching out into the deep lung areas and reducing deposition of the drug in the respiratory tract, one of the major obstacles in dose delivery via inhalation. A patient can inhale a dissolved free-base or salt formulation of a psychedelic drug or a derivative thereof as a mist into an alveolar region of the patient's lungs. The psychedelic drug or derivative can be delivered to a fluid lining of the alveolar region of the lungs and can be systemically absorbed into patient blood circulation. Advantageously, these formulations can be effectively delivered to the blood stream upon inhalation to the alveolar regions of the lungs.

Devices suitable for delivery of heated or unheated air, oxygen, or helium-oxygen mixtures include, for example, continuous mode nebulizers Flo-Mist (Phillips) and Hope (B&B Medical Technologies) and the accessories such as regulators, e.g., Medipure™ Heliox-LCQ System (PraxAir) and control box, e.g., Precision Control Flow (PraxAir). In some embodiments, a full delivery setup can be a device as described in, for example, Russian patent RU199823U1.

The term "heliox" as used herein refers to breathing gas mixtures of helium gas (He) and oxygen gas ($O_2$). In some embodiments, the heliox mixture can contain helium in the mixture of helium and oxygen at about 50%, 60%, 70%, 80% or 90% and contain oxygen in the mixture of helium and oxygen at about 50%, 40%, 30%, or 10%. The heliox mixture can thus contain helium and oxygen in a 50:50, 60:40, 70:30, 80:20, 90:10 ratio, or any ratio in between. In some embodiments, heliox can generate less airway resistance through increased tendency to laminar flow and reduced resistance in turbulent flow.

The use of heat in heliox mixtures can further enhance drug delivery by increasing permeability of key physical barriers for drug absorption. Heating of mucosal surfaces can increase permeability by enhancing peripheral blood circulation and relaxing the interstitial junction, as well as other mechanisms. Helium has a thermal conductivity almost 10 times higher than oxygen and nitrogen and can facilitate heat transfer more efficiently. A dry heliox mixture can be used safely as a pretreatment step when warmed up to as high as 110° C., which can enable the dry heliox mixture to heat mucosal surfaces of the lung and respiratory tract more efficiently.

Various types of personal vaporizers are known in the art. In general, personal vaporizers are characterized by heating a solid drug or compound. Vaporizers can work by directly heating a solid drug or compound to a smoldering point. Vaporizing a solid or solid concentrate can be done by convection on conduction. Convection heating of solid concentrate involves a heating element coming into contact with water, or another liquid, which then vaporizes. The hot vapor in turn directly heats the solid or solid concentrate to a smoldering point, releasing a vapor to be inhaled by a user. Conduction heating involves direct contact between the solid or solid concentrate and the heating element, which brings the solid to a smoldering point, releasing vapor to be inhaled by a user. Though vaporizers present advantages over smoking in terms of lung damage, the drug/active agent that is vaporized can be substantially deteriorated by the vaporizing heat.

A vapor is a solid substance in the gas phase at a temperature lower than its critical temperature, meaning that the vapor can be condensed to a liquid by increasing the pressure on it without reducing the temperature.

A mist, as used herein, differs from a vapor and is a dispersion of liquid droplets (liquid phase) suspended in a gas phase (e.g., air, oxygen, helium, and mixtures thereof). The liquid droplets of a mist can comprise a psychedelic drug or derivative thereof dissolved in an aqueous liquid or organic solvent. The liquid phase of mist droplets can contain thousands or millions of molecules. The gas phase of a mist can comprise air, oxygen, helium, and mixtures thereof. Mists do not comprise solid particulates. Mists can be created by any suitable methods, including for example, use of an inhaler or nebulizer In some embodiments, psychedelic drugs are delivered via a nebulizer, which generates an aqueous-droplet mist containing the psychedelic drugs, which is optionally combined with a heated helium-oxygen mixture. For example, a preparation of a psychedelic drug can be placed into a liquid medium and put into a mist by a device, such as a nebulizer. In some embodiments, a nebulizer can be, for example, a pneumatic compressor nebulizer, an ultrasonic nebulizer, a vibrating mesh or horn nebulizer, or a microprocessor-controlled breath-actuated nebulizer. In some embodiments, a nebulizer device can be a device as described in, for example, Russian patent RU199823U1.

A nebulizer is a device that turns a drug, such as a psychedelic drug, in solution or suspension into a fine mist for delivery to the lungs. A nebulizer can also be referred to as an atomizer. To atomize is to put a dissolved drug into a mist form. To deliver a drug by nebulization, a drug can be dispersed in a liquid medium, for example, water, ethanol, or propylene glycol. Additionally, psychedelic drugs or derivatives thereof can be carried in a vehicle such as, for example liposomes, polymers, emulsions, micelles, nanoparticles, or polyethylenimine (PEI). Liquid drug formations for nebulizers can be, for example, aqueous solutions or viscous solutions. After application of a dispersing forcer (e.g., jet of gas, ultrasonic waves, or vibration of mesh), the dissolved psychedelic drug is contained within liquid droplets, which are then inhaled. A mist can be liquid droplets containing the drug in air or another gaseous mixture (e.g., a mixture of helium and oxygen).

Jet nebulizers (also known as pneumatic nebulizers or compressor nebulizers) use compressed gas to make a mist. In some embodiments, a jet nebulizer is a microprocessor-controlled breath-actuated nebulizer, also called a breath-actuated nebulizer. A breath-actuated nebulizer creates a mist only when a patient is inhaling, rather than creating a mist continuously. A mist can be generated by, for example, passing air flow through a Venturi in a nebulizer bowl or cup. A Venturi is a system for speeding the flow of a fluid by constricting fluid in a cone shape tube. In the restriction, the fluid must increase its velocity, thereby reducing its pressure and producing a partial vacuum. As the fluid exits the constriction point, its pressure increases back to the ambient or pipe level pressure. This can form a low-pressure zone that pulls up droplets through a feed tube from a solution of drug in a nebulizer bowl, and in turn this creates a stream of atomized droplets, which flow to a mouthpiece. Higher air flows lead to a decrease in particle size and an increase in output. Due to droplets and solvent that saturates the outgoing gas, jet nebulizers can cool a drug solution in the nebulizer and increase solute concentration in the residual volume. A baffle in a nebulizer bowl or cup can be impacted by larger particles, retaining them and returning them to the solution in the nebulizer bowl or cup to be reatomized. Entrainment of air through a nebulizer bowl as the subject inhales can increase mist output during inspiration. Generation of a mist can occur with a smaller particle size distribution, but using smaller particle sizes can result in an increased nebulization time.

The unit of measurement generally used for droplet size is mass median diameter (MMD), which is defined as the average droplet diameter by mass. This unit c also be referred to as the mass mean aerodynamic diameter, or MMAD. The MMD droplet size for jet nebulizers can be about 1.0, 1.5, 2.0, 2.5, 3.0, 3.5, 4.0, 5.0, 6.0, 7.0, 8.0, 9.0, 10.0 μm or more (or any range between about 1.0 and 10.0 μm), which can be smaller than that of ultrasonic nebulizers.

Ultrasonic nebulizers generate mists by using the vibration of a piezoelectric crystal, which converts alternating current to high-frequency (about 1 to about 3 MHz) acoustic energy. The solution breaks up into droplets at the surface, and the resulting mist is drawn out of the device by the patient's inhalation or pushed out by gas flow through the device generated by a small compressor. Ultrasonic nebulizers can include large-volume ultrasonic nebulizers and small-volume ultrasonic nebulizers. Droplet sizes tend to be larger with ultrasonic nebulizers than with jet nebulizers. The MMD droplet size for ultrasonic nebulizers can be about 2.0, 2.5, 3.0, 3.5, 4.0, 4.5, 5.0, 5.5, 6.0, 6.5, 7.0, 7.5, 8.0, 9.0, 10.0 μm or more (or any range between about 2.0 and 10.0 m). Ultrasonic nebulizers can create a dense mist, with droplets at about 100, 150, 200, 250, 300 μm/L or more.

Mesh nebulizer devices use the vibration of a piezoelectric crystal to indirectly generate a mist. Mesh nebulizers include, for example, active mesh nebulizers and passive mesh nebulizers. Active mesh nebulizers use a piezo element that contracts and expands on application of an electric current and vibrates a precisely drilled mesh in contact with the drug solution to generate a mist. The vibration of a piezoelectric crystal can be used to vibrate a thin metal plate perforated by several thousand holes. One side of the plate is in contact with the liquid to be atomized, and the vibration forces this liquid through the holes, generating a mist of tiny droplets. Passive mesh nebulizers use a transducer horn that induces passive vibrations in the perforated plate with tapered holes to produce a mist. Examples of active mesh nebulizers include the Aeroneb® (Aerogen, Galway, Ireland) and the eFlow® (PARI, Starnberg, Germany), while the Microair NE-U22® (Omron, Bannockburn, IL) is a passive mesh nebulizer. Mesh nebulizers are precise and customizable. By altering the pore size of the mesh, the device can be tailored for use with drug solutions of different viscosities, and the output rate changed. Use of this method of atomization can offer several advantages. The size of the droplets can be extremely precise because droplet size can be determined by the size of the holes in the mesh (which may be tailor-made to suit the application). Nebulizer meshes can be manufactured using methods such as electrodeposition, electroplating, and laser cutting to produce a liquid particle in gas in the respirable range. Mesh can be made of metal alloy. The metals used in mesh manufacture can include platinum, palladium, nickel, and stainless steel. The size of the droplet is about twice the size of the mesh hole. Mesh holes, therefore, can be about 0.1, 0.5, 1.0, 1.5, 2.0, 2.5, 3.0, 3.5, 4.0, 4.5, 5.0 μm or more (or any value in between about 0.1 and 5.0 μm). Mist generation in mesh nebulizers can vary based on the shape of the mesh, the material that the mesh is made of, and also the way that the mesh is created. In other words, different meshes can produce different sized liquid particles suspended in gas. Generally, MMD droplet size for mesh nebulizers can be about 1.0, 1.5, 2.0, 2.5, 3.0, 3.5, 4.0, 4.5, 5.0, 5.5, 6.0, 6.1, 6.2, 6.3, 6.4, 6.5, 6.6, 6.7, 6.8, 6.9, 7.0 μm or more (or any value in between about 1.0 and 7.0 μm).

Additionally, droplet size can be programmable. In particular, geometric changes can be made to a nebulizer to provide a specific desired droplet size. Additionally, droplet size can be controlled independently of droplet velocity. The volume of liquid atomized, and the droplet velocity can also be precisely controlled by adjusting the frequency and amplitude of the mesh vibration. Furthermore, the number of holes in the mesh and their layout on the mesh can be tailored. Mesh nebulizers can be powered either by electricity or by battery.

A mist output rate in standing cloud mL per minute (for any atomization methodology described herein) can range from, for example, 0.1, 0.2, 0.3, 0.4, 0.5, 0.6, 0.7, 0.8, 0.9 mL/minute or more (or any range between about 0.1 and 0.9 mL/minute) and the residual volume in any type of nebulizer reservoir can range from a about 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 mL or more (or any range between about 0.01 and 2.0 mL). Precise droplet size control can be advantageous since droplet size can correlate directly to kinetic drug release (KDR). Precise control of KDR can be achievable with precise control of droplet size. Psychedelic drugs or derivatives thereof can be delivered via a mist using any methodology with an MMD droplet size of about 0.5, 1.0, 1.5, 2.0, 2.5, 3.0, 3.5, 4.0, 5.0, 6.0, 7.0, 8.0, 9.0, 10.0 µm or more (or any range between about 0.5 and 10.0 µm).

In some embodiments, a psychedelic drug can be delivered via a continuous positive airway pressure (CPAP) or other pressure-assisted breathing device. A pressure-assisted breathing device forces a continuous column of compressed air or other gas at a fixed designated pressure against the face and nose of the patient, who is wearing a mask or nasal cap. When the patient's glottis opens to inhale, the pressure is transmitted throughout the airway, helping to open it. When the patient exhales, pressure from the deflating lungs and chest wall pushes air out against the continuous pressure, until the two pressures are equal. The air pressure in the airway at the end of exhalation is equal to the external air pressure of the machine, and this helps "splint" the airway open, allowing better oxygenation and airway recruitment. A pressure-assisted breathing device can be coupled with a means for introducing mist particles into the gas flow in the respiratory circuit and or a means for discontinuing the introduction of mist particles into the respiratory circuit when the patient exhales. See, e.g. U.S. Pat. No. 7,267,121.

In some embodiments, a mist can be delivered by a device such as a metered dose inhaler (MDI), which generates an organic solvent-droplet mist containing the psychedelic drugs, which is optionally combined with a heated helium-oxygen mixture. In some embodiments, a psychedelic drug or derivative thereof can be delivered via a metered dose inhaler, MDL MDI devices can include a canister which contains the psychedelic drug or derivative thereof and a propellant, a metering valve which dispenses the medicament from the canister, an actuator body that receives the canister and which forms an opening for oral inhalation, and an actuator stem which receives the drug from the canister and directs it out the opening in the actuator body. Moving the drug canister relative to the actuator body and actuator stem causes the metering valve to release the predetermined amount of the drug. In some embodiments, the psychedelic drug or derivative thereof can be dissolved in a liquid propellant mixture (sometimes including small amounts of a volatile organic solvent) stored in a pressurized container of the MDL The "metered dose" is the dose that is prepackaged in a single-dose inhaler, or which in a multidose inhaler is automatically measured out of a reservoir in preparation for inhalation. MDI devices can be aided with spacers. An MDI spacer is a spacer that goes between the MDI and the mouth of a user of the MDI. An MDI spacer allows droplets in the atomized dose to settle out a bit and mix with air or other gas, thus allowing for more effective delivery of a metered dose into a user's lungs when inhaled. An MDI spacer assists in preventing a user from inhaling the metered dose directly from an MDI where the dose would be traveling so fast that the droplets of the atomized spray from the MDI hit and stick to the back of the user's throat rather than being inhaled into the user's lungs where the drug of the metered dose is designed to be delivered. MDI devices offer the advantage of regular dosing, which can be controlled in the manufacture of the drug.

Delivery of Psychedelic Drugs and Helium Oxygen Mixtures

Methods disclosed herein provide for systemic delivery of small doses of a psychedelic drug or derivatives thereof. In particular, a psychedelic drug or derivatives thereof can be delivered to a patient's CNS. Doses can be optimized for individual patients' metabolisms and treatment needs. Larger doses with deleterious or undesirable side-effects can be avoided by using small doses. Methods of treating various central nervous system (CNS) diseases and other conditions are described herein. The methods can comprise delivering a psychedelic drug or derivative thereof to a patient in need thereof via inhalation of an a mist comprising the drug and an gas such as air, oxygen, helium, or a mixture of helium and oxygen (i.e., a heliox mixture). In some embodiments the air, oxygen, helium, or mixture helium and oxygen can be heated. The method can further comprise a using a device containing a balloon with an oxygen-helium mixture equipped with a reducer and a mask connected to each other by a gas or air connecting tube, which contains an additional heating element capable of heating t gas mixture up to 120° C., a nebulizer with a vibrating porous plate or mesh, ensuring the passage of droplets with a size of less than 5 microns through it, and a disinfection unit.

In some embodiments, a psychedelic drug or derivatives thereof is delivered to the lower respiratory tract, for instance, to a pulmonary compartment such as alveoli, alveolar ducts and/or bronchioles. From there, the drug can enter the blood stream and travel to the central nervous system. In some embodiments of the present disclosure, delivering a psychedelic drug to a patient in need thereof via inhalation of a mist can deliver the psychedelic drug to the patient's CNS without passing through the liver. Administration via inhalation can allow gaseous drugs or those dispersed in a liquid or a mist, to rapidly deliver the psychedelic drug or derivative thereof to the blood stream, bypassing first-pass metabolism. First-pass metabolism, also known as "first-pass effect" or "presystemic metabolism" describes drugs that enter the liver and undergo extensive biotransformation.

In some embodiments, the method provides a treatment step, in which a psychedelic drug can be administered to a patient in need thereof by administering via inhalation a mixture of helium and oxygen heated to about 50° C., 51° C., 52° C., 53° C., 54° C., 55° C., 56° C., 57° C., 58° C., 59° C., 60° C., or more (or any range between 50° C. to 60° C.) and the atomized psychedelic drug or derivative thereof. In some embodiments, a mist or vapor of the psychedelic drug can have a particle size from about 0.1 microns to about 10 microns (e.g., about 10, 5, 4, 3, 2, 1, 0.1 or less microns). In some embodiments, the psychedelic drug or derivative thereof can be atomized via a nebulizer creating an inhalant that is a mist with the dissolved psychedelic drug. In some embodiments, the atomized psychedelic drug is driven down the patient delivery line by the patient's inhalation. In some embodiments, the atomized psychedelic drug is driven down the patient delivery line by the patient's inhalation using a carrier gas. The carrier gas can be air, oxygen, a mix of oxygen and helium, heated air, heated oxygen, or heated helium and oxygen mixture.

In some embodiments, the treatment step can be preceded by a pretreatment step. In some embodiments, the pretreatment step can comprise first administering a pretreatment inhalation therapy prior to administration of the mist of the psychedelic drug or derivative thereof. In some embodiments, the pretreatment inhalation step can comprise (i) administering via inhalation air, oxygen, or mixture of helium and oxygen heated to about 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., or more (or any range between about 90° C. and 120° C.) and no psychedelic drug, and then (ii) administering a treatment step of inhalation air, oxygen, a mix of oxygen and helium, heated air, heated oxygen, or heated helium and oxygen mixture. Heated air, heated oxygen, or heated helium and oxygen mixture, in combination with the atomized psychedelic drug or derivative thereof, can be heated to about 50° C., 51° C., 52° C., 53° C., 54° C., 55° C., 56° C., 57° C., 58° C., 59° C., 60° C., or more (or any range between about 50° C. and 60° C.).

In some embodiments of the present disclosure, step a pretreatment step (i) and a treatment step (ii) can be repeated 0, 1, 2, 3, 4, 5, or more times. In some embodiments of the present disclosure, steps (i) and (ii) can be repeated 0, 1, 2, 3, 4, 5, or more times followed by the treatment step, which can be repeated 0, 1, 2, 3, 4, 5, or more times. In some embodiments of the present disclosure, the treatment step can be repeated 0, 1, 2, 3, 4, 5, or more times with no pretreatment step.

Treatment, with optional pretreatment, can be administered once a week, twice a week, once a day, twice a day, three times a day or more. Each treatment can be for about 1, 5, 10, 20, 30, 45, 60 or more minutes.

A drug delivery procedure can comprise an inhaled priming no-drug hot heliox mixture to effectively preheat the mucosal bed followed by inhaling an atomized psychedelic drug, again driven by the heated heliox, but at lower temperatures, that are now dictated by lower heat tolerance to the wet vs. dry inhaled gas stream. Consequently, this procedure can be conducted in multiple repeated cycles, wherein a target PK and drug exposure is controlled by the concentration of the drug, temperature, flow rate of the helium oxygen mixture, composition of the mixture, number and durations of cycles, time and combinations of the above.

Methods of delivery described herein can be used to treat certain diseases and disorders. Treating and treatment refers to methods of alleviating or abrogating a condition, disorder, disease, one or more symptoms of a condition, disorder, or disease, or combinations thereof. Treating or treatment can include partial or complete halting of the progression of the condition, disorder, disease, or partial or complete reversal of the condition, disorder, disease. A treatment can provide a therapeutic benefit such as the eradication or amelioration of one or more of the physiological or psychological symptoms associated with the underlying condition, disease, or disorder such that an improvement is observed in the patient, notwithstanding the fact that the patient may still be affected by the condition.

Therefore, provided herein are methods of treating a central nervous system (CNS) disorder or psychological disorder comprising administering via inhalation a heated mixture of helium and oxygen heated and an atomized psychedelic drug. The treatment can alleviate one or more symptoms of the disorder.

In some embodiments, the psychedelic drug can be administered for treatment of CNS disease or other disorder. In some embodiments, the psychedelic drug can be administered to treat depression including, but not limited to major depression, melancholic depression, atypical depression, or dysthymia. In some embodiments the psychedelic drug can be administered to treat psychological disorders including anxiety disorder, obsessive compulsive disorder, addiction (narcotic addiction, tobacco addiction, opioid addiction), alcoholism, depression and anxiety (chronic or related to diagnosis of a life-threatening or terminal illness), compulsive behavior, or a related symptom.

In some embodiments, the disease or disorder is selected from the group consisting of central nervous system (CNS) disorders, including post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme disease, and obesity. In some embodiments, the disease or disorder may include conditions of the autonomic nervous system (ANS). In some embodiments, the disease or disorder may include pulmonary disorders (e.g., asthma and chronic obstructive pulmonary disorder (COPD). In some embodiments, the disease or disorder may include cardiovascular disorders (e.g., atherosclerosis).

The methods of delivering a psychedelic drug to the CNS (systemic drug delivery) via nebulizer (including, for example, using a heated helium-oxygen mixture), can lead to advantageous improvements in multiple PK parameters as compared to oral delivery. In particular, a psychedelic drug can cross the blood brain barrier and be delivered to the brain. As compared to oral delivery, the method of delivering a psychedelic drug to the CNS via nebulizer, optionally with a heated heliox mixture, can increase bioavailability by at least 25% as compared to oral delivery. In some embodiments, the method of delivering a psychedelic drug to the CNS via nebulizer as described herein, can increase bioavailability by about 10%, 25%, 30%, 35%, 40%, 50%, 55%, 60%, 65%, 70%, 80%, 85%, 90%, 95%, 99%, 99.9%, or more. The method of delivering a psychedelic drug to the CNS via nebulizer as described herein, can reduce $T_{max}$ by at least 50% as compared to oral delivery. In some embodiments, the method of delivering a psychedelic drug to the CNS via nebulizer as described herein, can reduce $T_{max}$ by at 30%, 40%, 50%, 55%, 60%, 65%, 70%, 80%, 85%, 90%, 95%, 99%, 99.9%, or more. In some embodiments, the method of delivering a psychedelic drug to the CNS via nebulizer as described herein, can increase $C_{max}$ by at least 25% as compared to oral delivery. In some embodiments, the method of delivering a psychedelic drug to the CNS via nebulizer as described herein, can increase $C_{max}$ by about 10%, 25%, 30%, 35%, 40%, 50%, 55%, 60%, 65%, 70%, 80%, 85%, 90%, 95%, 99%, 99.9%, or more. Furthermore, a method of delivering a psychedelic drug to the CNS via nebulizer as described herein, can allow clinical protocols enabling dose titration and more controlled exposure. Controlled exposure enables adjusting the patient experience and providing overall improved therapeutic outcomes.

In some embodiments, a system is provided for administering psychedelic drugs (or salts thereof) that includes a container comprising a solution of a psychedelic drug (or derivative or salt thereof) compound formulation and a nebulizer physically coupled or co-packaged with the container and adapted to produce a mist of the solution having a particle size from about 0.1 microns to about 10 microns (e.g., about 10, 5, 4, 3, 2, 1, 0.1 or less microns).

Topical or Transdermal Dosage Forms and Administration

Dosage forms for the topical or transdermal administration of a compound of the present disclosure (e.g., compounds of Formulas (I) through (IV), or a pharmaceutically acceptable salt thereof) include powders, sprays, ointments, pastes, creams, lotions, gels, solutions, patches and inhalants. The active compound may be mixed under sterile conditions with a pharmaceutically acceptable excipient, and with any preservatives, buffers, absorption enhancers, or propellants which may be required.

The ointments, pastes, creams and gels may contain, in addition to an active compound of the present disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the present disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. That is, the compounds of the present disclosure can be administered via a transdermal patch at a steady state concentration, whereby the compound is gradually administered over time, thus avoiding drug spiking and toxicity associated therewith.

Transdermal patch dosage forms herein may be formulated with various amounts of the active agent, depending on the disease/condition being treated. The quantity of active component in a unit dose preparation may be varied or adjusted e.g., from 5 mg to 25 mg, or 10 mg to 20 mg, or 12 mg to 18 mg, or 13 mg to 16 mg, or 14 mg to 15 mg, or otherwise as deemed appropriate using sound medical judgment, according to the particular application and the potency of the active component. Transdermal patches formulated with the disclosed compounds may be suitable for microdosing to achieve durable therapeutic benefits, with decreased toxicity. In some embodiments, compounds of the present disclosure may be administered via a transdermal patch at serotonergic, but sub-psychoactive concentrations, for example, over an extended period such as over a 24 hour period.

In addition to the compound of the present disclosure and any optional pharmaceutically acceptable excipient(s), the transdermal patch may also include one or more of a pressure sensitive adhesive layer, a backing, and a release liner, as is known to those of ordinary skill in the art.

Transdermal patch dosage forms can be made by dissolving or dispersing the compound in the proper medium. In some embodiments, the compounds of the present disclosure may be dissolved/dispersed directly into a polymer matrix forming the pressure sensitive adhesive layer. Such transdermal patches are called drug-in-adhesive (DIA) patches. Preferred DIA patch forms are those in which the active compound is distributed uniformly throughout the pressure sensitive adhesive polymer matrix. In some embodiments, the compounds of the present disclosure may be provided in a layer containing the active compound plus a polymer matrix which is separate from the pressure sensitive adhesive layer. In any case, the compounds of the present disclosure may optionally be formulated with suitable excipient(s) such as carriers and permeation agents/absorption enhancers to increase the flux of the compound across the skin.

Examples of carrier agents may include, but are not limited to, $C_8$-$C_{22}$ fatty acids, such as oleic acid, undecanoic acid, valeric acid, heptanoic acid, pelargonic acid, capric acid, lauric acid, and eicosapentaenoic acid; $C_8$-$C_{22}$ fatty alcohols such as octanol, nonanol, oleyl alcohol, decyl alcohol and lauryl alcohol; lower alkyl esters of $C_8$-$C_{22}$ fatty acids such as ethyl oleate, isopropyl myristate, butyl stearate, and methyl laurate; di(lower)alkyl esters of $C_6$-$C_{22}$ diacids such as diisopropyl adipate; monoglycerides of $C_8$-$C_{22}$ fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; glycerol; ethyl acetate; acetoacetic ester; N-alkylpyrrolidone; cyclodextrins, such as α-cyclodextrin, β-cyclodextrin, γ-cyclodextrin, or derivatives such as 2-hydroxypropyl-β-cyclodextrin; and terpenes/terpenoids, such as limonene, linalool, myrcene, pinene such as α-pinene, caryophyllene, citral, eucolyptol, and the like; including mixtures thereof.

Examples of permeation agents/absorption enhancers include, but are not limited to, sulfoxides, such as dodecylmethylsulfoxide, octyl methyl sulfoxide, nonyl methyl sulfoxide, decyl methyl sulfoxide, undecyl methyl sulfoxide, 2-hydroxydecyl methyl sulfoxide, 2-hydroxy-undecyl methyl sulfoxide, 2-hydroxydodecyl methyl sulfoxide, and the like; surfactant-lecithin organogel (PLO), such as those formed from an aqueous phase with one or more of poloxamers, CARBOPOL and PEMULEN, and a lipid phase formed from one or more of isopropyl palmitate and PPG-2 myristyl ether propionate, and lecithin; including mixtures thereof.

The pressure sensitive adhesive layer may be formed from polymers including, but not limited to, acrylics (polyacrylates including alkyl acrylics), polyvinyl acetates, natural and synthetic rubbers (e.g., polyisobutylene), ethyleneacetate copolymers, polysiloxanes, polyurethanes, plasticized polyether block amide copolymers, plasticized styrene-butadiene rubber block copolymers, and mixtures thereof. The pressure-sensitive adhesive layer used in the transdermal patch of the present disclosure may be formed from an acrylic polymer pressure-sensitive adhesive, preferably an acrylic copolymer pressure sensitive adhesive. The acrylic copolymer pressure sensitive adhesive may be obtained by copolymerization of one or more alkyl (meth)acrylates (e.g., 2-ethylhexyl acrylate); aryl (meth)acrylates; arylalkyl (meth)acrylate; and (meth)acrylates with functional groups such as hydroxyalkyl (meth)acrylates (e.g., hydroxyethyl acrylate, 2-hydroxypropyl acrylate, 3-hydroxypropyl acrylate, 4-hydroxybutyl acrylate, 2-hydroxyethyl methacrylate, 2-hydroxypropyl methacrylate, 3-hydroxypropyl methacrylate, and 4-hydroxybutyl methacrylate), carboxylic acid containing (meth)acrylates (e.g., acrylic acid), and alkoxy (meth)acrylates (e.g., methoxyethyl acrylate); optionally with one or more copolymerizable monomers (e.g., vinylpyrrolidone, vinyl acetate, etc.). Specific examples of acrylic pressure-sensitive adhesives may include, but are not limited to, DURO-TAK products (Henkel) such as DURO-TAK 87-900A, DURO-TAK 87-9301, DURO-TAK 87-4098, DURO-TAK 87-2074, DURO-TAK 87-235A, DURO-TAK 87-2510, DURO-TAK 87-2287, DURO-TAK 87-4287, and DURO-TAK 87-2516.

The backing used in the transdermal patch of the present disclosure may include flexible backings such as films, nonwoven fabrics, Japanese papers, cotton fabrics, knitted fabrics, woven fabrics, and laminated composite bodies of a nonwoven fabric and a film. Such a backing is preferably composed of a soft material that can be in close contact with a skin and can follow skin movement and of a material that can suppress skin rash and other discomforts following prolonged use of the patch. Examples of the backing materials include, but are not limited to, polyethylene, polypropylene, polyethylene terephthalate, polybutylene terephthalate, polyethylene naphthalate, polystyrene, nylon, cotton, acetate rayon, rayon, a rayon/polyethylene terephthalate composite body, polyacrylonitrile, polyvinyl alcohol, acrylic polyurethane, ester polyurethane, ether polyurethane, a styrene-isoprene-styrene copolymer, a styrene-butadiene-styrene copolymer, a styrene-ethylene-propylene-styrene copolymer, styrene-butadiene rubber, an ethylene-vinyl acetate copolymer, or cellophane, for example. Preferred backings do not adsorb or release the active agent. In order to suppress the adsorption and release of the active agent, to improve transdermal absorbability of the active agent, and to suppress skin rash and other discomforts, the backing preferably includes one or more layers composed of the material above and has a water vapor permeability. Specific examples of backings may include, but are not limited to, 3M COTRAN products such as 3M COTRAN ethylene vinyl acetate membrane film 9702, 3M COTRAN ethylene vinyl acetate membrane film 9716, 3M COTRAN polyethylene membrane film 9720, 3M COTRAN ethylene vinyl acetate membrane film 9728, and the like.

The release liner used in the transdermal patch of the present disclosure may include, but is not limited to, a polyester film having one side or both sides treated with a release coating, a polyethylene laminated high-quality paper treated with a release coating, and a glassine paper treated with a release coating. The release coating may be a fluoropolymer, a silicone, a fluorosilicone, or any other release coating known to those of ordinary skill in the art. The release liner may have an uneven surface in order to easily take out the transdermal patch from a package. Examples of release liners may include, but are not limited to SCOTCH-PAK products from 3M such as 3M SCOTCHPAK 9744, 3M SCOTCHPAK 9755, 3M SCOTCHPAK 9709, and 3M SCOTCHPAK 1022.

Methods disclosed herein using a transdermal patch dosage form provide for systemic delivery of small doses of drug, preferably over extended periods of time such as up to 72 hours, or up to 60 hours, or up to 48 hours, or up to 36 hours, for example from 2 to 72 hours, or 4 to 24 hours, or 10 to 18 hours, or 12 to 14 hours. In particular, the compounds of the present disclosure can be delivered in small, steady, and consistent doses such that deleterious or undesirable side-effects can be avoided. In some embodiments, the compounds of the present disclosure are administered transdermally at serotonergic, but sub-psychoactive concentrations.

Therefore, provided herein are methods of treating a disease or disorder associated with a serotonin 5-HT$_2$ receptor, such as a central nervous system (CNS) disorder, a psychological disorder, or an autonomic nervous system (ANS), comprising administering a compound of the present disclosure (e.g., compounds of Formulas (I) through (IV), or a pharmaceutically acceptable salt thereof) via a transdermal patch. Here, the compound of the present disclosure is one that is capable of diffusing from the matrix of the transdermal patch (e.g., from the pressure sensitive adhesive layer) across the skin of the subject and into the bloodstream of the subject.

In some embodiments, the compound can be administered for treatment of CNS disease or other disorder. In some embodiments, the compound can be administered to treat depression including, but not limited to major depression, melancholic depression, atypical depression, or dysthymia. In some embodiments the psychedelic drug can be administered to treat psychological disorders including anxiety disorder, obsessive compulsive disorder, addiction (narcotic addiction, tobacco addiction, opioid addiction), alcoholism, depression and anxiety (chronic or related to diagnosis of a life-threatening or terminal illness), compulsive behavior, or a related symptom.

In some embodiments, the disease or disorder is selected from the group consisting of central nervous system (CNS) disorders, including post-traumatic stress disorder (PTSD), major depressive disorder (MDD), treatment-resistant depression (TRD), suicidal ideation, suicidal behavior, major depressive disorder with suicidal ideation or suicidal behavior, non-suicidal self-injury disorder (NSSID), bipolar and related disorders including bipolar I disorder, bipolar II disorder, cyclothymic disorder, obsessive-compulsive disorder (OCD), generalized anxiety disorder (GAD), social anxiety disorder, substance use disorders including alcohol use disorder, opioid use disorder, amphetamine use disorder, nicotine use disorder, and cocaine use disorder, anorexia nervosa, bulimia nervosa, binge eating disorder, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, chronic fatigue syndrome, Lyme disease, and obesity. In some embodiments, the disease or disorder may include conditions of the autonomic nervous system (ANS). In some embodiments, the disease or disorder may include pulmonary disorders (e.g., asthma and chronic obstructive pulmonary disorder (COPD). In some embodiments, the disease or disorder may include cardiovascular disorders (e.g., atherosclerosis).

EXAMPLES

I. Synthetic Routes

Compounds of the present disclosure and Reference Compounds may generally be prepared according to, or analogous to, the following synthetic procedures, which are depicted in FIGS. 1-15.

Example 1

Synthesis of 2-(2,5-bis(methoxy-d3)-4-(methylthio) phenyl)ethan-1-amine (II-1)

Synthesis of 2-(2,5-bis(methoxy-d3)-4-(methylthio)phenyl)ethan-1-amine (TI-1) was carried out according to FIG. 1. The phenolic starting material II-1a was deprotonated with potassium carbonate in DMF and placed in the presence of deuterated methyl iodide to yield the bis(methoxy-d3) benzaldehyde intermediate (II-1b, 85%). The bis(methoxy-d3) benzaldehyde (II-1b) was brominated with elemental bromine in glacial acetic acid to yield the benzaldehyde intermediate (II-1c, 37%), which was reduced to the alcohol using sodium borohydride (II-1d, 92%). The alcohol was displaced to yield the benzyl bromide intermediate (II-1e, 94%), which was subsequently displaced with potassium cyanide to yield the benzyl cyanide (II-1f, 32%). A Pd$_2$(dba)$_3$/xanphos-catalyzed cross coupling between bromobenzylcyanide TI-1f and sodium methanethiolate provided intermediate II-1g (44%), which then underwent a reduction with lithium aluminum hydride to yield, after acidic work-up, II-1 (75%), as an HCl salt. The structure of the product was confirmed by H NMR; total yield, 2.9%.

Example 2

Synthesis of 2-(2,5-bis(methoxy-d3)-4-methylphenyl)ethan-1-amine (II-2)

Figure 2:
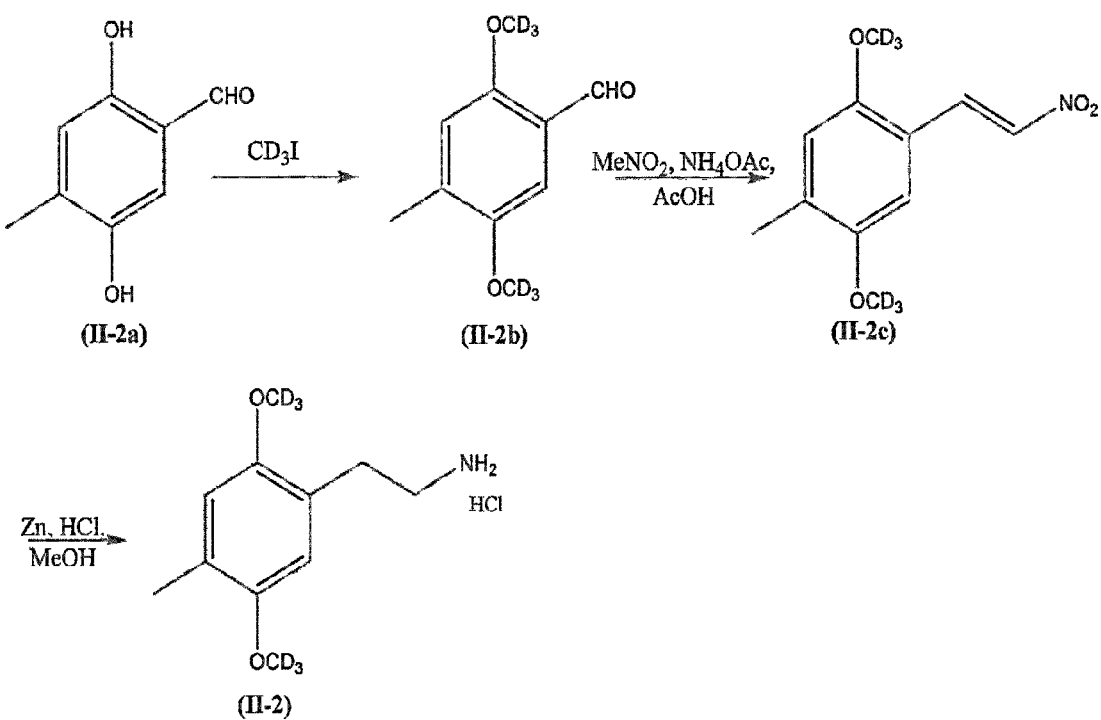
FIG. 2 illustrates the synthetic route for making Compound II-2.

Synthesis of 2-(2,5-bis(methoxy-d3)-4-methylphenyl)ethan-1-amine (II-2) is carried out according to FIG. 2, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). Bis-alkylation of 2,5-dihydroxy-4-methylbenzaldehyde II-2a with CD$_3$I provides intermediate II-2b, which is then subjected to a nitroaldol condensation with nitromethane in buffered acidic conditions to form the p-nitrostyrene II-2c. Subsequent bis-reduction of the nitro group and alkene with zinc dust in methanol containing hydrochloric acid yields the final product (II-2), as an HCl salt. The structure of the product will be confirmed by $^1$H NMR.

Example 3

Synthesis of 2-(4-(tert-butyl)-2,5-bis(methoxy-d3)phenyl)ethan-1-amine (II-3)

Figure 3:
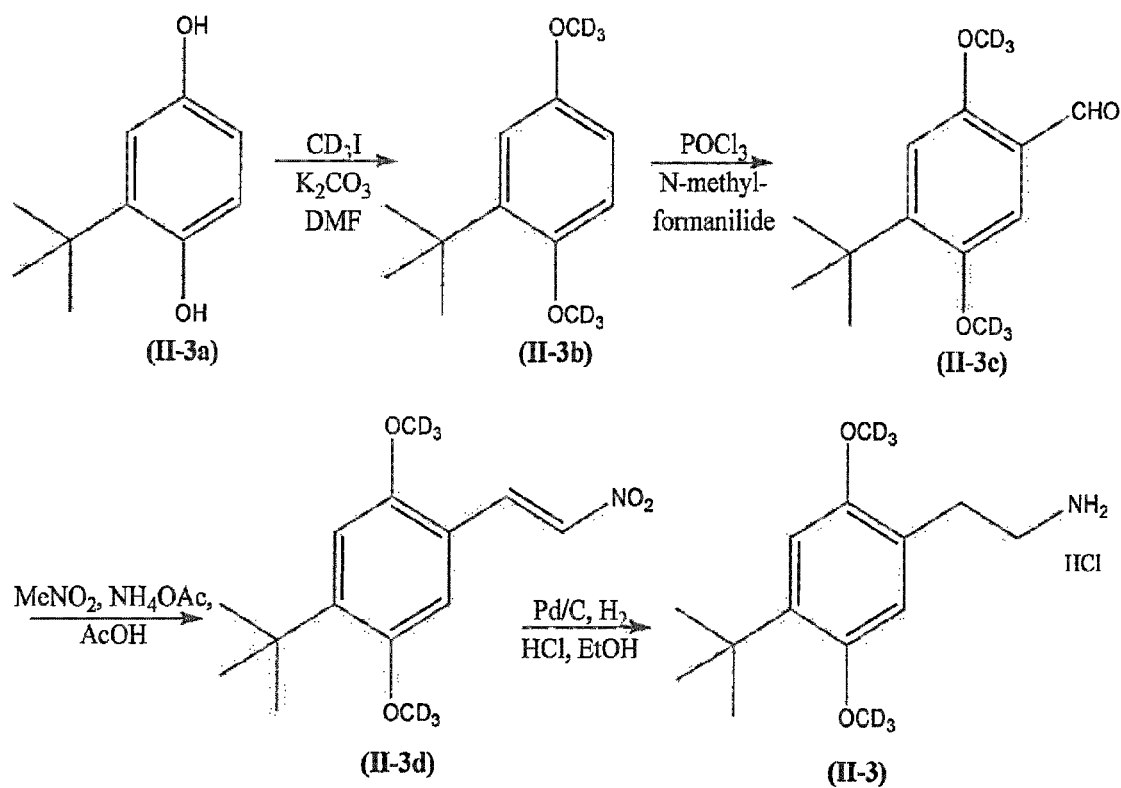
FIG. 3 illustrates the synthetic route for making Compound II-3.

Synthesis of 2-(4-(tert-butyl)-2,5-bis(methoxy-d3)phenyl)ethan-1-amine (II-3) was carried out according to FIG. 3. Bis-alkylation of starting material (II-3a) with CD$_3$I afforded intermediate II-3b (78%). Selective formylation with POCl$_3$ and N-methylformanilide afforded benzaldehyde intermediate II-3c (63%). The resulting benzaldehyde II-3c underwent a nitroaldol condensation with nitromethane in buffered acidic conditions to form the β-nitrostyrene II-3d (72%). Subsequent bis-reduction of the nitro group and alkene with Pd/C, H$_2$, ethanol containing hydrochloric acid yields the final product (II-3, 32%), as an HCl salt. The structure of the product was confirmed by $^1$H NMR.

Example 4

Synthesis of 2-(4-cyclopentyl-2,5-bis(methoxy-d3)phenyl)ethan-1-amine (II-4)

Figure 4:
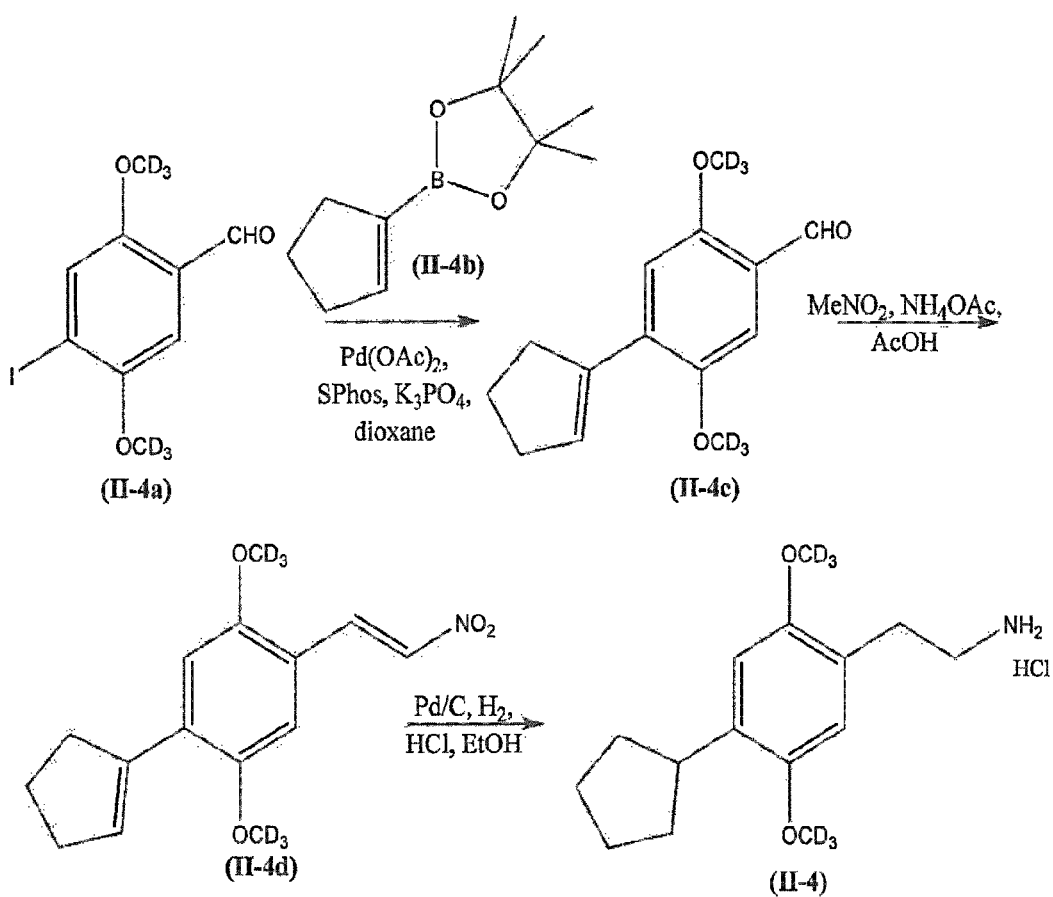
FIG. 4 illustrates the synthetic route for making Compound II-4.

Synthesis of 2-(4-cyclopentyl-2,5-bis(methoxy-d3)phenyl)ethan-1-amine (II-4) was carried out according to FIG. 4. A Pd(OAc)$_2$/Sphos-catalyzed cross coupling between iodobenzaldehyde starting material II-4a and boronic ester II-4b provided intermediate II-4c (78%), which then was subjected to a nitroaldol condensation with nitromethane in buffered acidic conditions to form the β-nitrostyrene II-4d. Multi-site hydrogenation with Pd/C then yielded the final product (II-4, 52%), as an HCl salt. The structure of the product was confirmed by $^1$H NMR.

Example 5

Synthesis of 2-(4-bromo-2,5-bis(methoxy-d3)phenyl)ethan-1,1,2,2-d4-1-amine (II-14)

Figure 5:
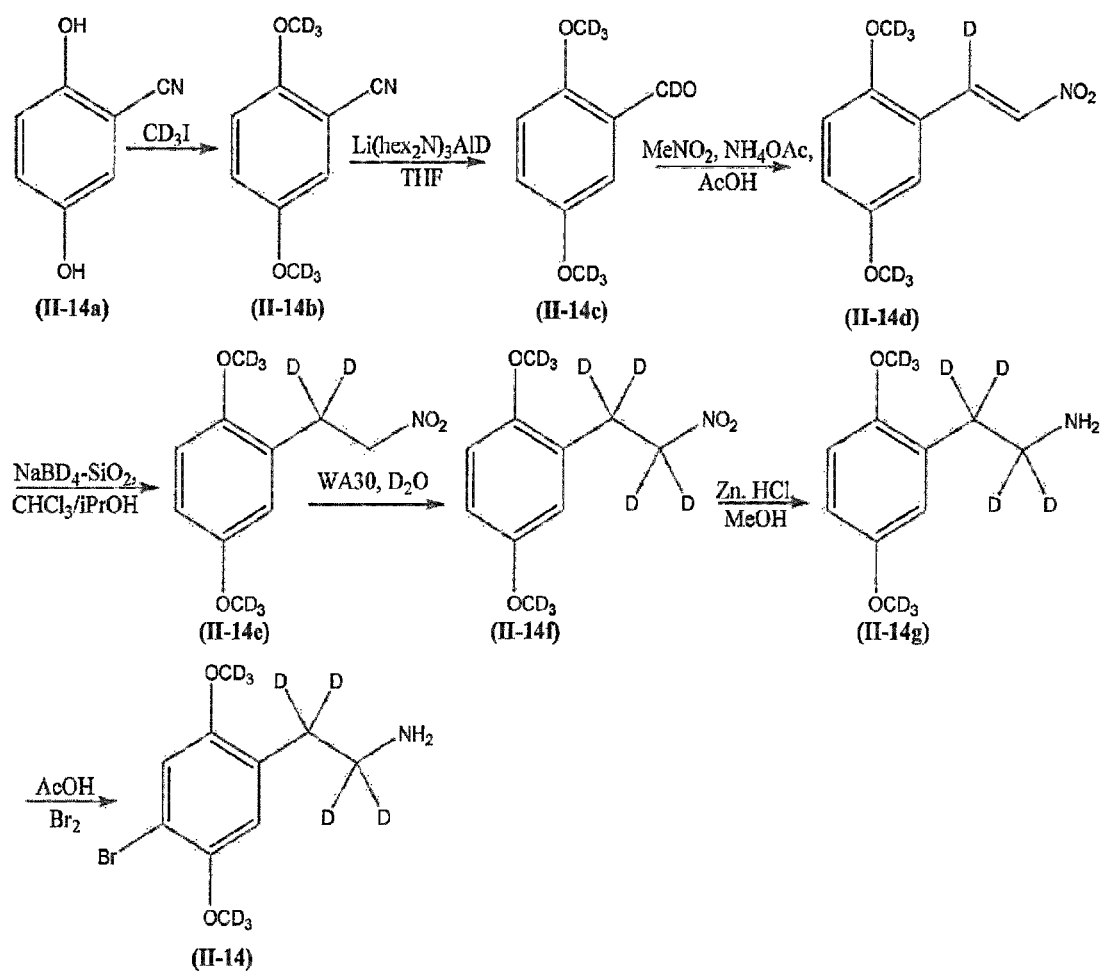
FIG. 5 illustrates the synthetic route for making Compound II-14.

Synthesis of 2-(4-bromo-2,5-bis(methoxy-d3)phenyl)ethan-1,1,2,2-d4-1-amine (II-14) is carried out according to FIG. 5, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). Bis-alkylation of 2,5-dihydroxybenzonitrile (II-14a) with CD$_3$I forms intermediate II-14b, which is then deuterated by reduction using lithium tris(dihexylamino)aluminum deuteride (Li(hex$_2$N)$_3$AlD) to the deuterated benzaldehyde II-14e using a method developed by Cha (Cha, J. S., Lee, S. E., and Lee, H. S., 1992, Selective Conversion of Aromatic Nitriles to Aldehydes by Lithium Tris(Dihexylamino)Aluminum Hydride, *Org Prep Proced Int* 24, 331-334). β-nitrostyrene II-14d is formed using a nitroaldol condensation with nitromethane in buffered acidic conditions. Subsequent treatment with sodium borodeuteride and silicone dioxide selectively reduces the alkene to intermediate II-14e (Sinhababu, A. K., and Borchardt, R. T. (1983) Silica Gel-Assisted Reduction of Nitrostyrenes to 2-Aryl-1-Nitroalkanes with Sodium-Borohydride, *Tetrahedron Letters* 24, 227-230), followed by deuterium exchange at the α-position using the basic resin WA30 and deuterated water developed by Yamada (Yamada, T., Kuwata, M., Takakura, R., Mon chi, Y., Sajiki, H., and Sawama, Y. (2018) Organocatalytic Nitroaldol Reaction Associated with Deuterium-Labeling, *Adv Synth Catal* 360, 637-641), which forms intermediate II-14f. Reduction of the nitro group with zinc dust in methanol containing hydrochloric acid yields intermediate 11-14g. Selective bromination then affords final product (II-14). The structure of the product will be confirmed by $^1$H NMR.

Example 6

Synthesis of 2-(2,5-dimethoxy-4-(methyl-d3)phenyl)ethan-1-amine (III-1)

Figure 6:
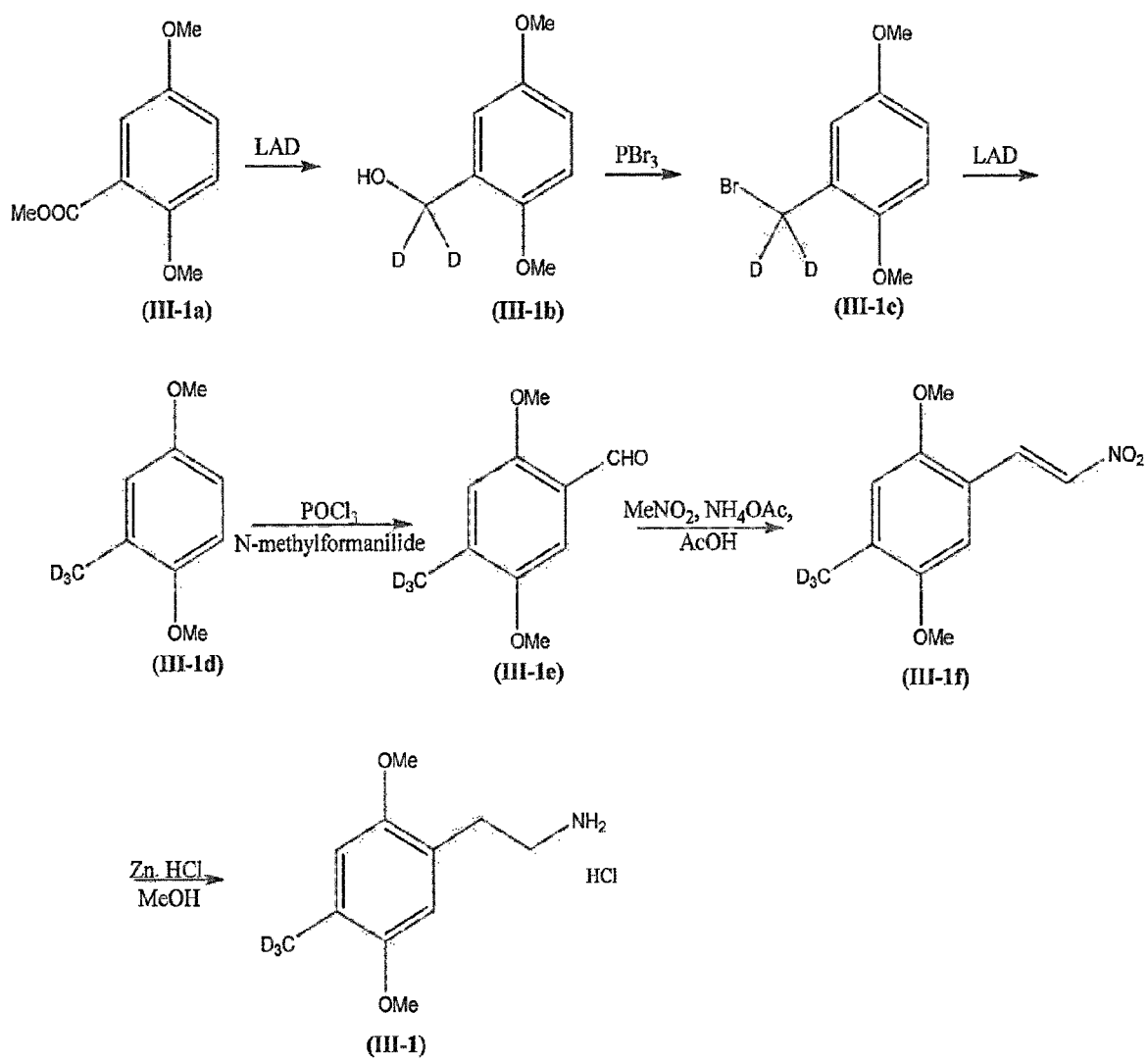
FIG. 6 illustrates the synthetic route for making Compound III-1.

Synthesis of 2-(2,5-dimethoxy-4-(methyl-d3)phenyl)ethan-1-amine (III-1) is carried out according to FIG. 6, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). Reduction of methyl 2,5- dimethoxybenzoate (III-1a) with lithium aluminum deuteride (LAD) provides benzyl alcohol intermediate III-1b, which is subsequently converted to benzyl bromide intermediate III-1c upon reaction with $PBr_3$. Further reaction with LAD provides intermediate III-1d, which is selectively formylated with N-methylformanilide and $POCl_3$. The resulting benzaldehyde III-1e undergoes a nitroaldol condensation with nitromethane in buffered acidic conditions to form the β-nitrostyrene III-1f. Subsequent bis-reduction of the nitro group and alkene with zinc dust in methanol containing hydrochloric acid yields the final product (III-1), as an HCl salt. The structure of the product will be confirmed by $^1H$ NMR.

Example 7

Synthesis of 2-(2,5-dimethoxy-4-(2-(methyl-d3) propan-2-yl-1,1,1,3,3,3-d6)phenyl)ethan-1-amine (III-2)

Figure 7:
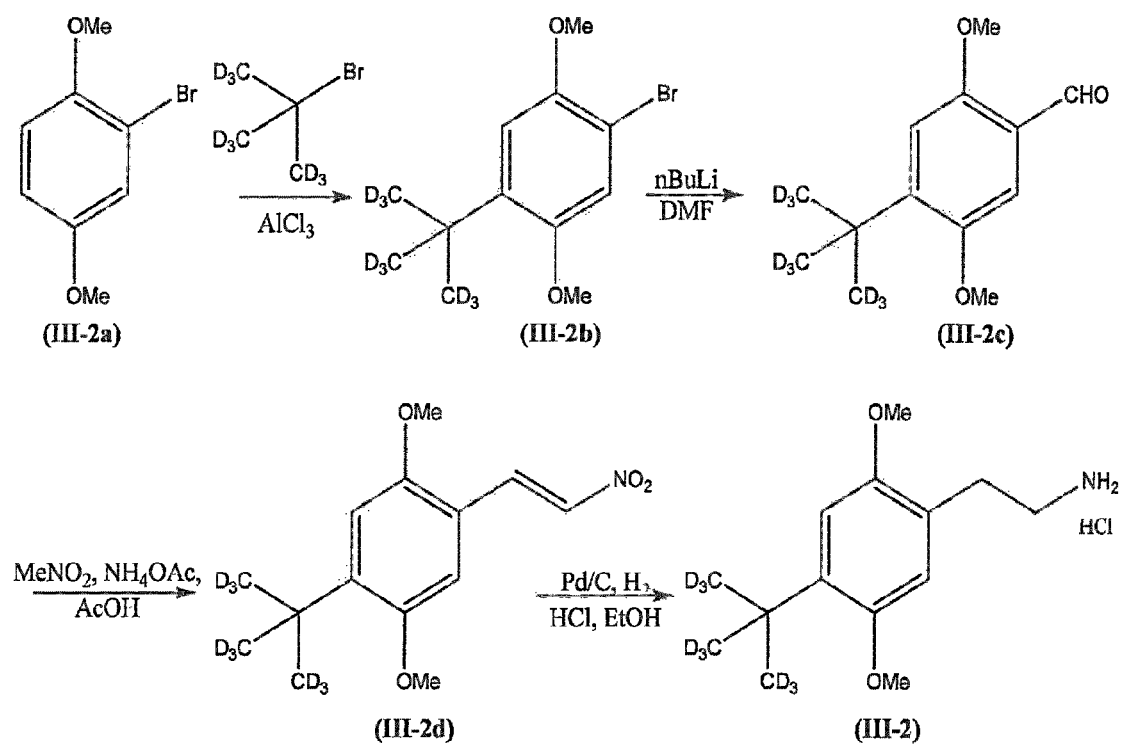
FIG. 7 illustrates the synthetic route for making Compound III-2.

Synthesis of 2-(2,5-dimethoxy-4-(2-(methyl-d3)propan-2-yl-1,1,1,3,3,3-d6)phenyl)ethan-1-amine (III-2) was carried out according to FIG. 7. Friedel-Crafts alkylation of starting material (III-2a) was carried out using t-butyl bromide-d9 and aluminum chloride to afford intermediate III-2b, which was then lithiated with n-butyl lithium and quenched with DMF. The resulting benzaldehyde III-2c underwent a nitroaldol condensation with nitromethane in buffered acidic conditions to form the β-nitrostyrene III-2d. Subsequent bis-reduction of the nitro group and alkene with Pd/C, $H_2$, ethanol containing hydrochloric acid yielded the final product (III-2), as an HCl salt. The structure of the product was confirmed by $^1H$ NMR.

Example 8

Synthesis of 2-(2,5-dimethoxy-4-(methylthio)phenyl)ethan-1,1-d2-1-amine (IV-1)

Figure 8:
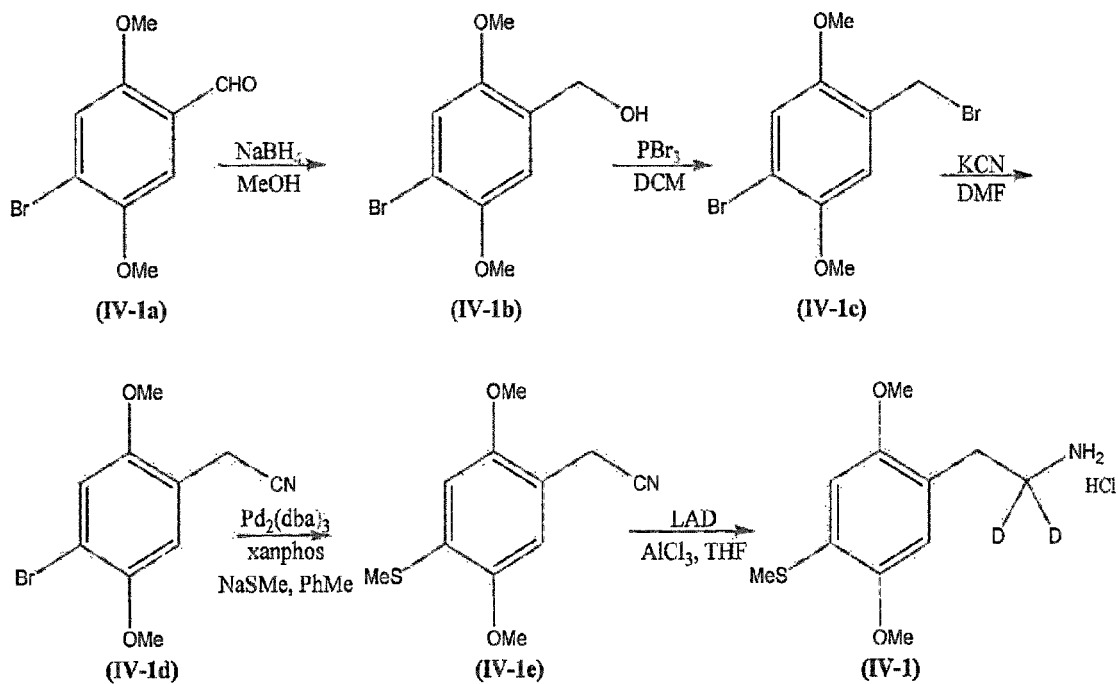
FIG. 8 illustrates the synthetic route for making Compound IV-1.

Synthesis of 2-(2,5-dimethoxy-4-(methylthio)phenyl)ethan-1,1-d2-1-amine (IV-1) was carried out according to FIG. 8. Reduction of starting material IV-1a with sodium borohydride yielded benzyl alcohol (IV-1b, 95%), which was then converted with $PBr_3$ to benzyl bromide (IV-1c, 96%). Displacement with potassium cyanide then yielded the benzyl cyanide (IV-1d, 14%). A $Pd_2(dba)_3$/xanphos-catalyzed cross coupling with sodium methanethiolate provided intermediate IV-1e (44%), which was then reduced with lithium aluminum deuteride in the presence of aluminum chloride to yield final product (IV-1, 27%). The structure of the product was confirmed by H NMR.

Example 9

Synthesis of 2-(2,5-dimethoxy-4-(propylthio)phenyl)ethan-1,1-d2-1-amine (IV-2)

Figure 9:
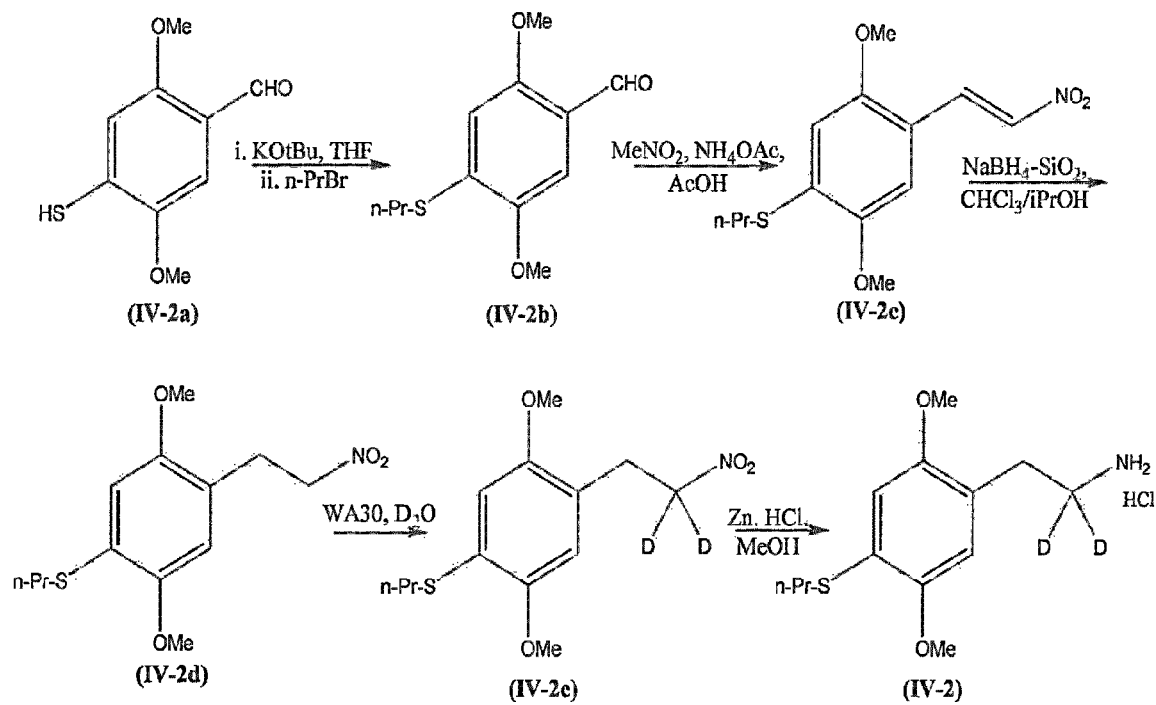
FIG. 9 illustrates the synthetic route for making Compound IV-2.

Synthesis of 2-(2,5-dimethoxy-4-(propylthio)phenyl) ethan-1,1-d2-1-amine (IV-2) is carried out according to FIG. 9, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). 4-mercapto-2,5-dimethoxybenzaldehyde (IV-2a) is alkylated by first deprotonating the thiol using potassium tert-butoxide in THF, followed by the addition of n-propyl bromide. The resulting benzaldehyde IV-2b undergoes a nitroaldol condensation with nitromethane in buffered acidic conditions to form the β-nitrostyrene IV-2c. Subsequent treatment with sodium borohydride and silicone dioxide selectively reduces the alkene, forming intermediate IV-2d, followed by deuterium exchange at the i-position using the basic resin WA30 and deuterated water developed by Yamada (Yamada, T., Kuwata, M., Takakura, R., Monguchi, Y., Sajiki, H., and Sawama, Y. (2018) Organocatalytic Nitroaldol Reaction Associated with Deuterium-Labeling, *Adv Synth Catal* 360, 637-641) to form intermediate IV-2e. Reduction of the nitro group with zinc dust in methanol containing hydrochloric acid yields the final product (IV-2), as an HCl salt. The structure of the product will be confirmed by $^1H$ NMR.

Example 10

Synthesis of 2-(2,5-dimethoxy-4-(trifluoromethyl)phenyl)ethan-1,1-d2-1-amine (IV-3)

Figure 10:
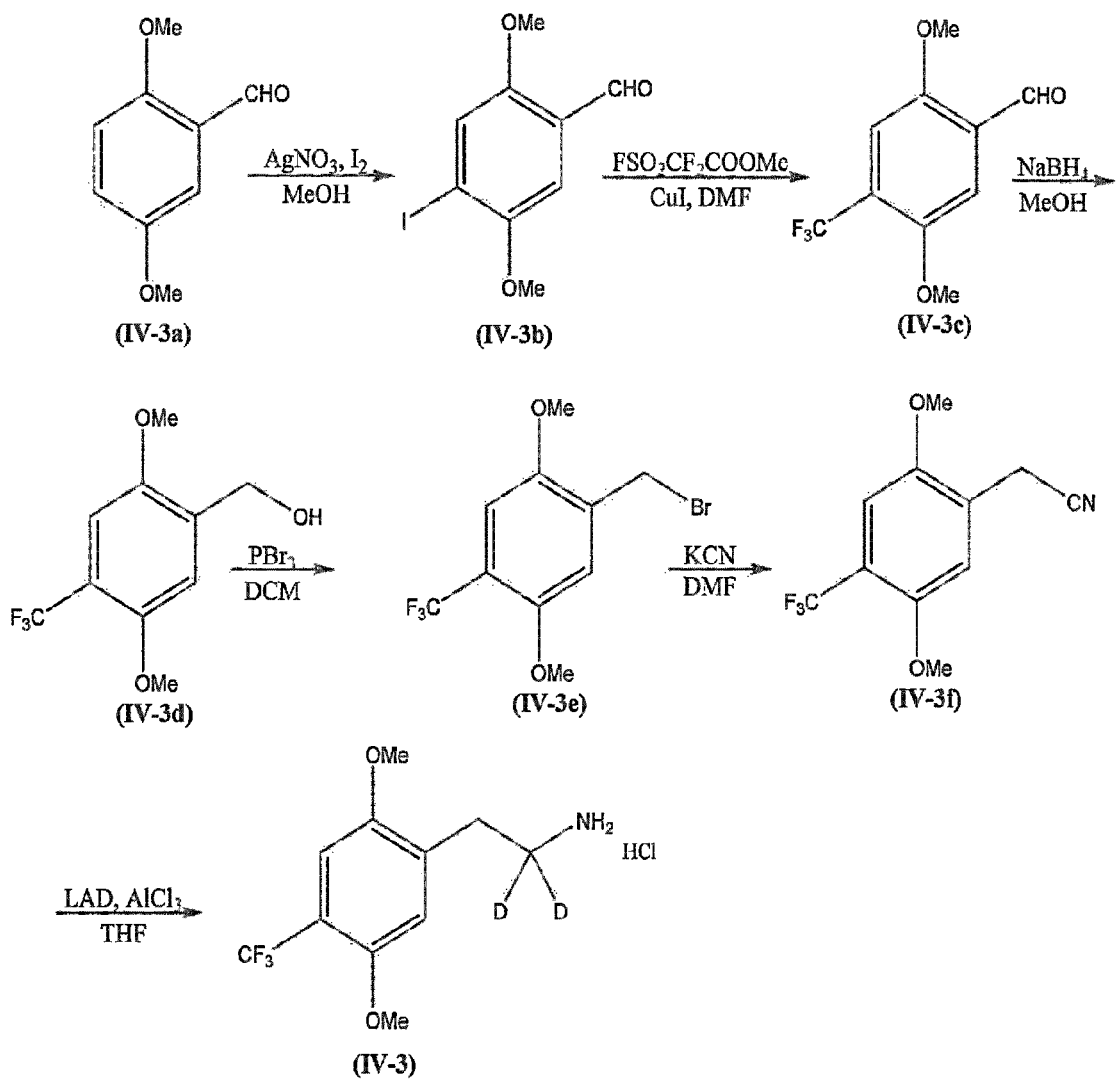
FIG. 10 illustrates the synthetic route for making Compound IV-3.

Synthesis of 2-(2,5-dimethoxy-4-(trifluoromethyl)phenyl)ethan-1,1-d2-1-amine (V-3) was carried out according to FIG. 10. Installation of iodine onto starting material IV-3a was accomplished with $AgNO_3$ and $I_2$ to produce iodoarene intermediate (IV-3b, 81%), which was then catalytically trifluoromethylated with $FSO_2CF_2COOMe$ in DMF at 75° C. in the presence of catalytic amounts of CuI to yield intermediate V-3c (66%). Reduction with sodium borohydride yielded benzyl alcohol (IV-3d, 97%), which was then converted with $PBr_3$ to benzyl bromide (IV-3e, 62%). Displacement with potassium cyanide then yielded the benzyl cyanide (IV-3f, 13%), which was then reduced with lithium aluminum deuteride in the presence of aluminum chloride to yield, after acidic work-up, final product (IV-3, 60%), as an HCl salt. The structure of the product was confirmed by $^1H$ NMR.

Example 11

Synthesis of 2-(4-bromo-2,5-dimethoxyphenyl)ethan-1,1-$d_2$-1-amine (IV-5)

Figure 11:
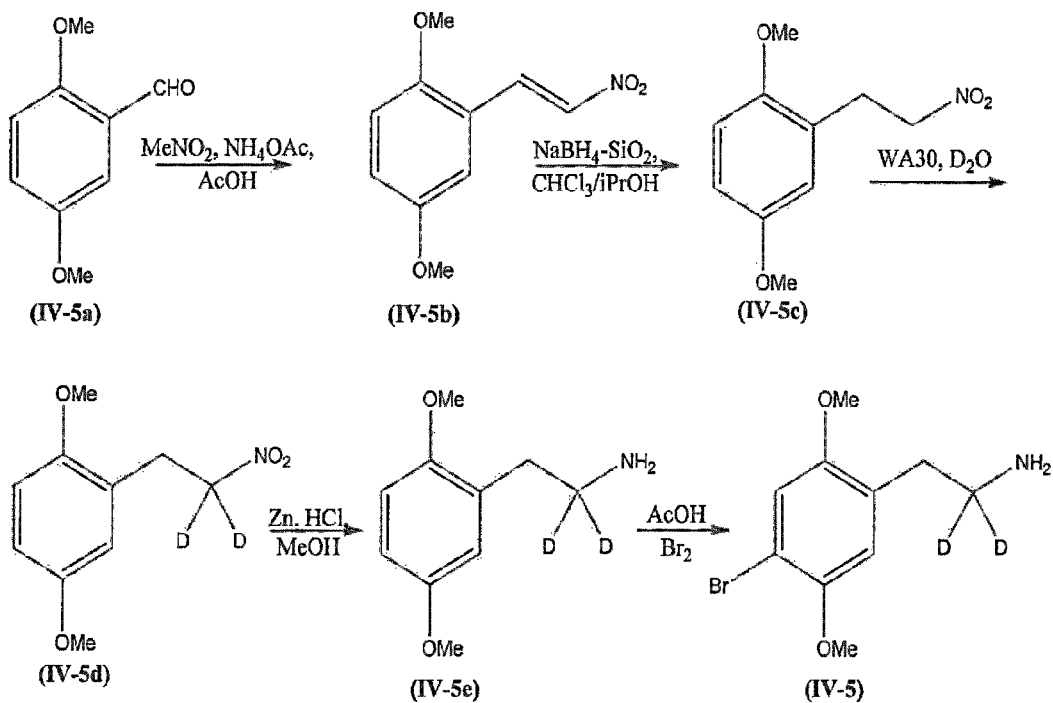
FIG. 11 illustrates the synthetic route for making Compound IV-5.

Synthesis of 2-(4-bromo-2,5-dimethoxyphenyl)ethan-1,1-d2-1-amine (IV-5) is carried out according to FIG. 11, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). 2,5-Dimethoxybenzaldehyde (IV-5a) undergoes a nitroaldol condensation using nitromethane in buffered acidic conditions to form the β-nitrostyrene IV-5b. Subsequent treatment with sodium borohydride and silicone dioxide selectively reduces the alkene to intermediate IV-5c followed by deuterium exchange at the α-position using the basic resin WA30 and deuterated water developed by Yamada (Yamada, T., Kuwata, M., Takakura, R., Monguchi, Y., Sajiki, H., and Sawama, Y. (2018) Organocatalytic Nitroaldol Reaction Associated with Deuterium-Labeling, *Adv Synth Catal* 360,

Example 12

Synthesis of 2-(4-bromo-2,5-dimethoxyphenyl)ethan-1,1,2,2-d4-1-amine (IV-12)

Figure 12:
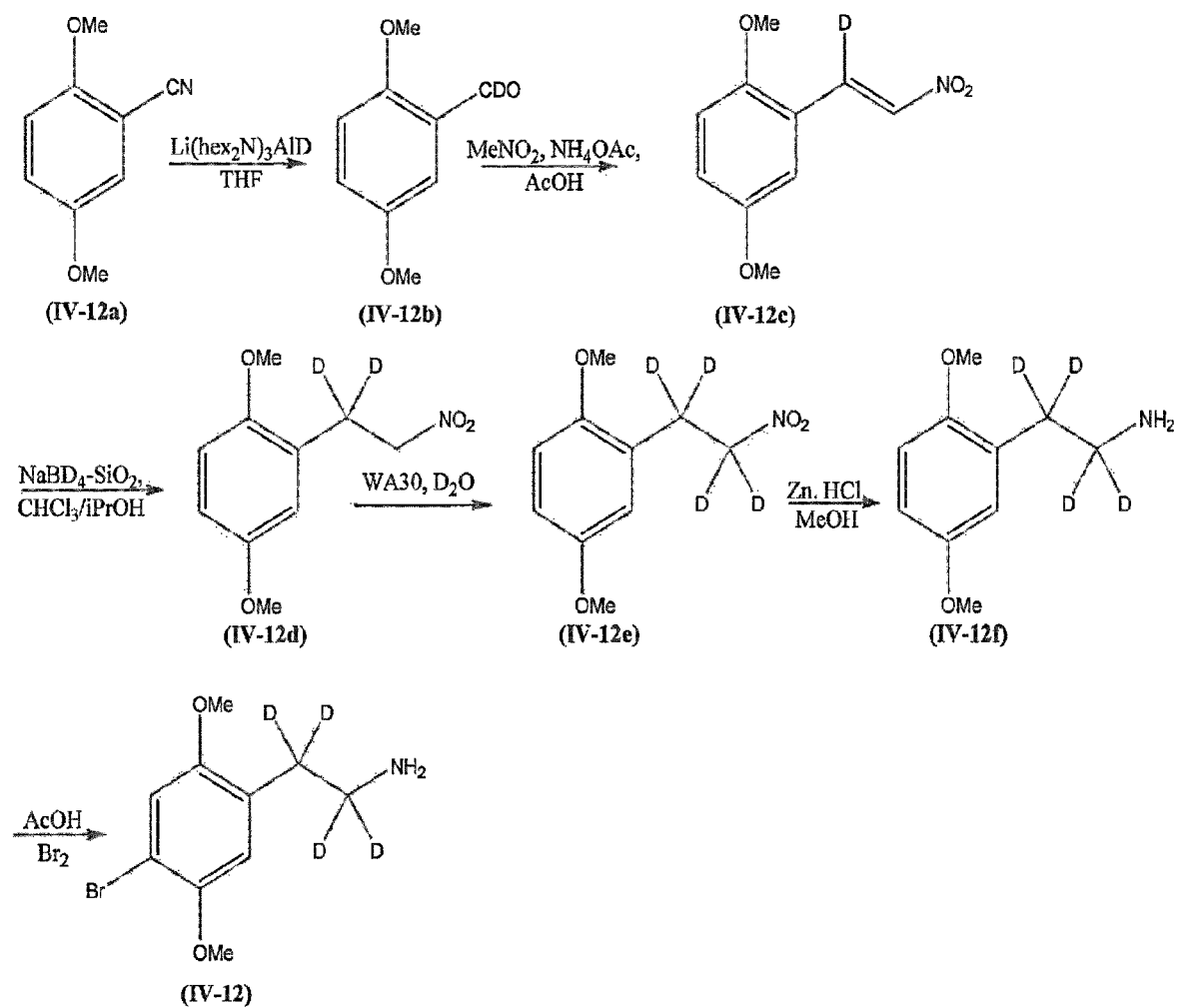
FIG. 12 illustrates the synthetic route for making Compound IV-12.

Synthesis of 2-(4-bromo-2,5-dimethoxyphenyl)ethan-1,1,2,2-d4-1-amine (IV-12) is carried out according to FIG. 12, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). The starting material IV-12a is deuterated by reduction using lithium tris(dihexylamino)aluminum deuteride (Li(hex$_2$N)$_3$AlD) to the deuterated benzaldehyde IV-12b using a method developed by Cha (Cha, J. S., Lee, S. E., and Lee, H. S., 1992, Selective Conversion of Aromatic Nitriles to Aldehydes by Lithium Tris(Dihexylamino)Aluminum Hydride, *Org Prep Proced Int* 24, 331-334). β-nitrostyrene IV-12c is formed using a nitroaldol condensation with nitromethane in buffered acidic conditions. Subsequent treatment with sodium borodeuteride and silicone dioxide selectively reduces the alkene to intermediate IV-12d (Sinhababu, A. K., and Borchardt, R. T. (1983) Silica Gel-Assisted Reduction of Nitrostyrenes to 2-Aryl-1-Nitroalkanes with Sodium-Borohydride, *Tetrahedron Letters* 24, 227-230), followed by deuterium exchange at the α-position using the basic resin WA30 and deuterated water developed by Yamada (Yamada, T., Kuwata, M., Takakura, R., Monguchi, Y., Sajiki, H., and Sawama, Y. (2018) Organocatalytic Nitroaldol Reaction Associated with Deuterium-Labeling, *Adv Synth Catal* 360, 637-641) to form intermediate IV-12e. Reduction of the nitro group with zinc dust in methanol containing hydrochloric acid yields intermediate IV-12f. Selective bromination then affords final product (IV-12). The structure of the product will be confirmed by $^1$H NMR.

Example 13

Synthesis of 2-(2,5-dimethoxy-4-((trifluoromethyl)thio)phenyl)ethan-1-amine (I-1)

Figure 13:
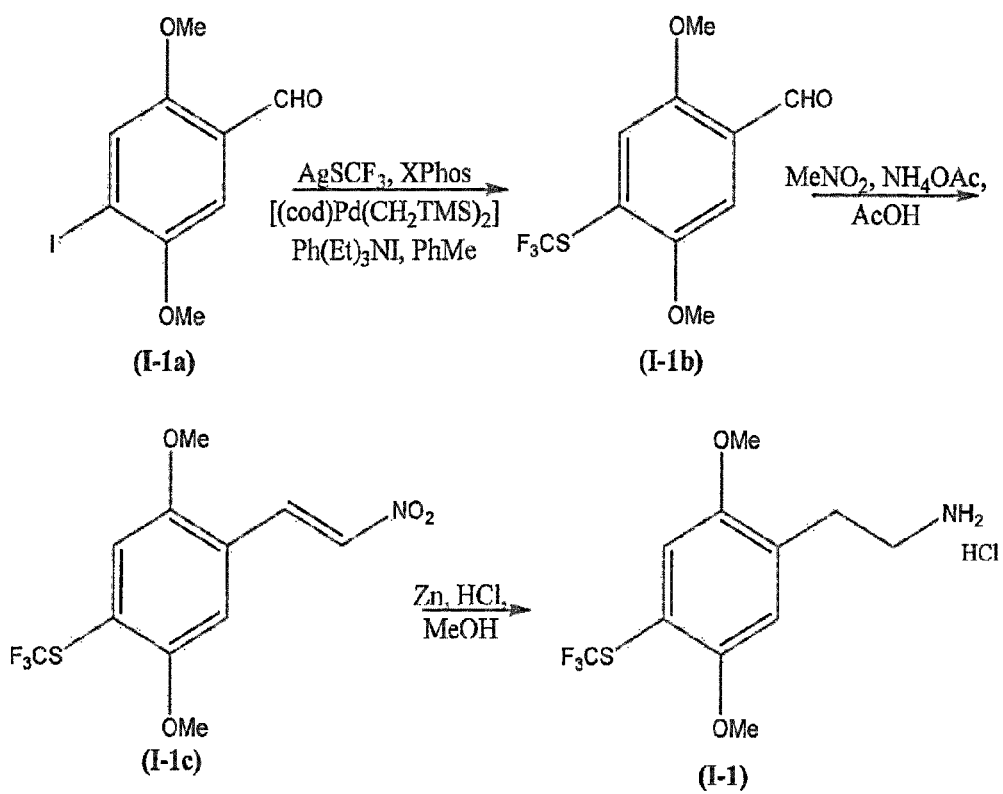
FIG. 13 illustrates the synthetic route for making Compound I-1.

Synthesis of 2-(2,5-dimethoxy-4-((trifluoromethyl)thio)phenyl)ethan-1-amine (I-1) was carried out according to FIG. 13. A Pd/XPhos-catalyzed cross coupling between iodobenzaldehyde starting material I-1a and AgSCF$_3$ was carried out using (1,5-cyclooctadiene)bis(trimethylsilylmethyl)palladium(II) catalyst in the presence of phenyltriethylammonium iodide to provide intermediate (I-1b, 46%). Next, a nitroaldol condensation was performed with nitromethane in buffered acidic conditions to form the β-nitrostyrene (I-1c, 48%). Subsequent bis-reduction of the nitro group and alkene with zinc dust in methanol containing hydrochloric acid yielded the final product (I-1, 33%), as an HCl salt. The structure of the product was confirmed by $^1$H NMR.

Examples 14-25

Figure 14:
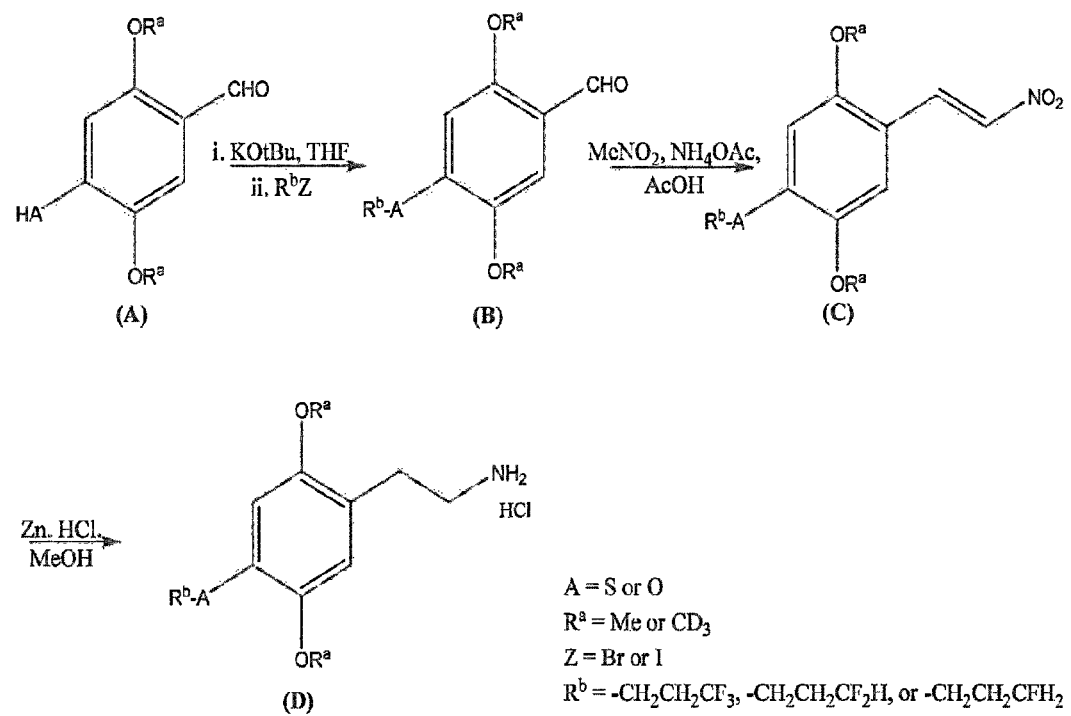
FIG. 14 illustrates the synthetic route for making Compounds of Formula (I) with a fluoropropoxy or fluorothiopropoxy substituent as $R^4$, e.g., Compounds I-2, I-3, I-4, I-5-I-6, I-7, II-16, II-17, I-18, II-19, II-20 and II-21.

Examples 14-25 are prepared according to general FIG. 14, using a modified general procedure as reported by Shulgin (Shulgin, A., and Shulgin, Ann. (1991) *Pihkal: a chemical love story*, Transform Press, Berkeley, CA) and later modified by Maresh (Maresh, J. J., Ralko, A. A., Speltz, T. E., Burke, J. L., Murphy, C. M., Gaskell, Z., Girel, J. K., Terranova, E., Richtscheidt, C., and Krzeszowiec, M. (2014) Chemoselective Zinc/HCl Reduction of Halogenated beta-Nitrostyrenes: Synthesis of Halogenated Dopamine Analogues, *Synlett* 25, 2891-2894). Suitable starting material (A) is alkylated by first deprotonating the thiol using potassium tert-butoxide in THF, followed by the addition of suitable fluoroalkyl halide (R$^b$Z). The resulting intermediate B undergoes a nitroaldol condensation with nitromethane in buffered acidic conditions to form the β-nitrostyrene C. Subsequent bis-reduction of the nitro group and alkene with zinc dust in methanol containing hydrochloric acid yields the final product (D), as an HCl salt.

Example 14

2-(2,5-dimethoxy-4-((3,3,3-trifluoropropyl)thio)phenyl)ethan-1-amine (I-2). The structure of the product will be confirmed by $^1$H NMR.

Example 15

2-(4-((3,3-difluoropropyl)thio)-2,5-dimethoxyphenyl)ethan-1-amine (I-3). The structure of the product will be confirmed by $^1$H NMR.

Example 16

2-(4-((3-fluoropropyl)thio)-2,5-dimethoxyphenyl)ethan-1-amine (I-4). The structure of the product will be confirmed by $^1$H NMR.

Example 17

2-(2,5-dimethoxy-4-(3,3,3-trifluoropropoxy)phenyl)ethan-1-amine (I-5). The structure of the product will be confirmed by $^1$H NMR.

Example 18

2-(4-(3,3-difluoropropoxy)-2,5-dimethoxyphenyl)ethan-1-amine (I-6). The structure of the product will be confirmed by $^1$H NMR.

Example 19

2-(4-(3-fluoropropoxy)-2,5-dimethoxyphenyl)ethan-1-amine (I-7). The structure of the product will be confirmed by $^1$H NMR.

Example 20

2-(2,5-bis(methoxy-d3)-4-((3,3,3-trifluoropropyl)thio)phenyl)ethan-1-amine (II-16). The structure of the product will be confirmed by $^1$H NMR.

Example 21

2-(4-((3,3-difluoropropyl)thio)-2,5-bis(methoxy-d3)phenyl)ethan-1-amine (II-17). The structure of the product will be confirmed by $^1$H NMR.

Example 22

2-(4-((3-fluoropropyl)thio)-2,5-bis(methoxy-d3)phenyl)ethan-1-amine (II-18). The structure of the product will be confirmed by $^1$H NMR.

Example 23

2-(2,5-bis(methoxy-d3)-4-(3,3,3-trifluoropropoxy)phenyl)ethan-1-amine (II-19). The structure of the product will be confirmed by $^1$H NMR.

Example 24

2-(4-(3,3-difluoropropoxy)-2,5-bis(methoxy-d3)phenyl)ethan-1-amine (II-20). The structure of the product will be confirmed by $^1$H NMR.

Example 25

2-(4-(3-fluoropropoxy)-2,5-bis(methoxy-d3)phenyl)ethan-1-amine (II-21). The structure of the product will be confirmed by $^1$H NMR.

Reference Compound 1

Synthesis of 2-(2,5-dimethoxy-4-methylphenyl)ethan-1-amine (Reference Compound 1) ("2C-D")

Figure 15:
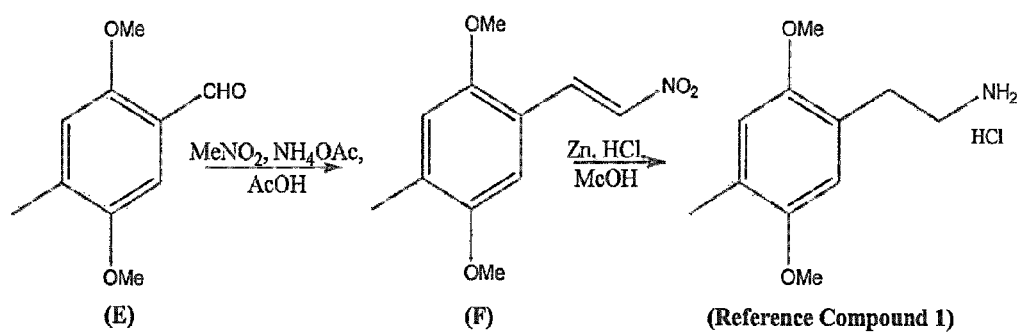
FIG. 15 illustrates the synthetic route for making Reference Compound 1.

Synthesis of 2-(2,5-dimethoxy-4-methylphenyl)ethan-1-amine (Reference Compound 1) is carried out according to FIG. 15. 2,5-dimethoxy-4-methylbenzaldehyde (E) is subjected to a nitroaldol condensation with nitromethane in buffered acidic conditions to form the β-nitrostyrene (F). Subsequent bis-reduction of the nitro group and alkene with zinc dust in methanol containing hydrochloric acid yielded the final product (Reference Compound 1), as an HCl salt. The structure of the product will be confirmed by $^1$H NMR.

Reference Compound 2

2-(4-bromo-2,5-dimethoxyphenyl)ethan-1-amine (Reference Compound 2) ("2C-B") is commercially available and was purchased from Cayman Chemical Co.

II. Formulations

Preparation of Ion-Exchange Resin Complex

Freebase of the compounds are complexed with a strong cation-exchange resin (sodium form, Amberlite IRP69, Rohm & Haas, Sodium Polystyrene Sulfonate, pharmaceutical grade USP, particle size 75-150 microns). The maximum load of the above resin is known to be about 5 meqv/g. Ina typical procedure, the compound free base (10 mmol) is dissolved in 20 ml of ethanol. To this solution, 2 g of the IRP69 resin (washed with 3×50 ml of ethanol) is added at room temperature using a magnetic stirrer and kept stirring for 2 h. The resin is then filtered and washed with ethanol (2×20 ml). Compound release from the resin complex is studied using a Type I (basket) dissolution apparatus at pH 1 (0.1 M HCl) and 7.4 (0.1 M phosphate buffer).

Ion-Exchange Resin Complex with Compound (II-14): An ion-Exchange Resin Complex with Compound (II-14) was prepared and the release profile studies according to the above procedure. In an acidic environment, the release was a fast process, with >90% of the drug leaching out within 30 mi. At neutral pH, the release was substantially slower, with about 50% of the drug released in 1 h and 80% at 2 h. The drug concentration was determined by HPLC using an Agilux 1100 setup and UV detection.

Preparation of Beads of Ion Exchange Resin Complex Coated by Enteric Coating

Seal Coating

Compound-ion-exchange resin Complex beads are seal-coated at a 2% weight gain using Opadry 03K19229 coating (Colorcon, NJ, USA, reconstituted at 6% solids) in a hydro-alcoholic solvent system (88:12, isopropanol:water) on a Niro-Aeromatic STREA 1 fluidized bed machine equipped with a Wurster coating module (bottom feed).

Enteric Coating

The resulting beads are then coated using Opadry Enteric 940 white coating (Colorcon, NJ, USA). Coating dispersions are reconstituted at 10% solids in a hydro-alcoholic solvent system (88:12, isopropanol:water) and applied to either a 5 or 12% weight gain. Enteric coating of placebo tablets is carried out without the preceding seal coating step. Samples are drawn at 5, 6, 7, 8, 10 and 12% weight gains.

Drug Release Testing

Drug release at low pH is determined using a Type I apparatus 1 (basket), at 100 rpm. In the first stage, the dissolution medium is 1000 ml of 0.1 N HCl at 37° C. (±0.5° C.) and the bead load 2 g. After 1 h of operation in this medium, an aliquot is withdrawn and the drug content is determined by HPLC to be less than 1% total, confirming the integrity of the applied enteric coating. Drug release at neutral pH is determined using a Type I apparatus 1 (basket), at 100 rpm. In the second stage, the dissolution medium is 1000 mL of 0.1 M phosphate buffer at pH 7.4 at 37° C. (0.5° C.) and a 2 g bead load. The medium aliquots are withdrawn at 15, 30, 60, 90, and 120 mi, and the drug content is determined by HPLC using an Agilux 1100 setup and UV detection. The release of the drug is found to be ca. 50% at 1 h and 80% at 2 h, with a release profile over time similar to the uncoated resin beads.

Manufacturing of Orally Disintegrating Tablets

Orally disintegrated tablets are designed by incorporating micro-beads of the drug-ion exchange resin complex with extended release characteristics into a matrix of the fast orally disintegrating components that help dispersing active material in the oral cavity and facilitate subsequent swallowing without use of water for more convenient administration of the drug.

Compounds are formulated into an orally disintegrating release tablet form, composition PI-ODT-1 by dry granulation using sugar based, fast-disintegrating matrix Pharmaburst 500 (SPI, PA, USA). 100 g of Pharmaburst 500 is mixed up with 20 g of the enterically coated compound-ion-exchange resin complex beads and sieved via 40 mesh sieves, to break agglomerates, and then the mixture is blended in a 400 ml tube blender for 15 minutes at 200 rev/min. After blending, magnesium stearate (200 mg) is added and blended for additional 3 minutes. The 250 mg convex-shaped tablets containing about 20 mg of active compound are compressed using a TDP tablet press and 9 mm dye. By applying a compression force of 8 kN, tablets of the hardness in the range 10-15 kP are generated. The tablet disintegration time is determined to be 60-75 seconds. The tablet dissolution is carried out in a Type II dissolution apparatus (paddle) (Distek Premiere 5100 Dissolution System, Distek Inc., North Brunswick, USA) at 100 rpm, 37° C., using 1×PBS buffer, pH=6.8 as an immersion media. At predetermined time intervals, 1 ml samples are withdrawn (not replaced), filtered and assayed. The amount of compound released is measured by HPLC using an Agilent 1100 setup (Nagy, J., and Veress, T., 2016, HPLC Analysis of Hallucinogenic Mushroom Alkaloids (Psilocin and Psilocybin) Applying Hydrophilic Interaction Chromatography (HILIC), *J Forensic Res* 7, 356). Solutions of known concentrations of compound are used to calculate the amount of drug released.

Fatty Acid Salts of Compounds

Compound free bases (10 mmol) are dissolved in 30 ml of acetone and 10 mmol of decanoic acid is added and mixed for 5 min. A white crystalline precipitate of the 1:1 salt is formed upon cooling the mixture in a refrigerator overnight. The salt composition will be confirmed by elemental analysis.

Preparation of Transdermal Skin Patches and In Vitro Permeation Studies

Compound I-1 was formulated in a drug-in-adhesive (DIA) patch to enable a steady delivery of the sub-psychedelic dose of the drug over extended periods of time. The formulation was optimized for a once-a-day application (24 h drug release). The DIA patch consisted of the drug, pressure sensitive acrylic-based adhesive, backing film, and release liner. In the preparation, 1.5 g of Compound I-1 and 6.0 g of DURO-TAK 87-900A (acrylate copolymer pressure sensitive adhesive; Henkel) were dissolved in 30 ml of methanol, the solution was agitated at room temperature for 30 mi, and spread on a silicone-coated release liner (SCOTCHPAK; 3M, St. Paul, USA) with a micrometer adjustable film applicator to give a wet film thickness of 300 micron. They were kept at room temperature for 5 min and then in an oven at 75° C. for 30 in to remove any residual solvents. The patches were then laminated with backing membrane (COTRAN; 3M, St. Paul, USA), cut into appropriate sizes, packed in aluminum-foil, and stored at room temperature. The final dry thickness of the DIA matrix was 90 mm.

The in vitro permeation of the drug patch across human cadaver skins (Biopredic, USA) was evaluated using Franz diffusion cells. A circular transdermal patch was pressed on the skin with the adhesive side facing the stratum corneum. The receptor cells were filled with PBS containing 6% (w/v) Brij 98. The diffusion cell area for all in vitro studies was 1.77 cm$^2$. The diffusion cells were maintained at 32° C., and the solution in the receptor cells was stirred continuously at 600 rpm. At designated time points (2, 4, 6, 8, 10, 12, and 24 h), 0.5 ml of the solution in the receptor cell was withdrawn and replaced with an equal volume of fresh receptor medium. The concentrations of FX in the samples were determined by LC-MS/MS analysis. A flux in the range of 20-25 microg/h/cm$^2$ was achieved, which should translate to the therapeutically relevant exposures in human subjects.

III. TESTING

5-HT Serotonin Receptor Pharmacodynamics

Binding affinity ($K_i$) and functional potency ($EC_{50}$) values of the compounds are measured. Deuteration is found to have little effect on the affinity and function at key receptor targets. Receptor Affinity Assays: 5-HT$_{1A}$, 5-HT$_{2(A,B,C)}$ receptor affinities are determined by radioligand competition binding as previously described (Canal, C. E., Cordova-Sintjago, T., Liu, Y., Kim, M. S., Morgan, D., and Booth, R. G., 2013, Molecular pharmacology and ligand docking studies reveal a single amino acid difference between mouse and human serotonin 5-HT$_{2A}$ receptors that impacts behavioral translation of novel 4-phenyl-2-dimethylaminotetralin ligands, *J Pharmacol Exp Ther* 347, 705-716; Armstrong, J. L., Casey, A. B., Saraf, T. S., Mukherjee, M., Booth, R. G., and Canal, C. E., 2020, (S)-5-(2'-Fluorophenyl)-N,N-dimethyl-1,2,3,4-tetrahydronaphthalen-2-amine, a Serotonin Receptor Modulator, Possesses Anticonvulsant, Prosocial, and Anxiolytic-like Properties in an Fmr1 Knockout Mouse Model of Fragile X Syndrome and Autism Spectrum Disorder, *ACS Pharmacol Transl Sci* 3, 509-523). Briefly, membranes from CHO-K1 or HEK293 cells expressing serotonergic receptors are collected and incubated in assay buffer with $K_d$ concentrations of radioligands and tests compounds that compete for receptor binding sites. After equilibration, the reaction is terminated by collecting ligand-receptor-membrane complexes (Microbeta, PerkinElmer), and radioactivity is measured by a scintillation counter (Microbeta2, PerkinElmer). Data are fit to non-linear curves, and K values are calculated per the Cheng-Prusoff equation.

Receptor Function Assays: 5-HT$_{1A}$ receptor-mediated Gi stimulation (reduction in cyclic adenosine monophosphate (cAMP) levels) and 5-HT$_{2(A,B,C)}$ receptor-mediated Gq stimulation (phosphoinositide hydrolysis leading to the production of inositol phosphate 1 (IP1))—canonical signaling pathways—are measured as previously described (Canal, C. E., Cordova-Sintjago, T., Liu, Y., Kim, M. S., Morgan, D., and Booth, R. G., 2013, Molecular pharmacology and ligand docking studies reveal a single amino acid difference between mouse and human serotonin 5-HT$_{2A}$ receptors that impacts behavioral translation of novel 4-phenyl-2-dimethylaminotetralin ligands, *J Pharmacol Exp Ther* 347, 705-716; Canal, C. E., Morgan, D., Felsing, D., Kondabolu, K., Rowland, N. E., Robertson, K. L., Sakhuja, R., and Booth, R. G., 2014, A Novel Aminotetralin-Type Serotonin (5-HT) (2C) Receptor-Specific Agonist and 5-HT$_{2A}$ Competitive Antagonist/5-HT2B Inverse Agonist with Preclinical Efficacy for Psychoses, *J Pharm Exp Ther* 349, 533), for example, with a homogeneous time-resolved fluorescence (HTRF) capable microplate reader (e.g., Mithras LB 940, Berthold) using commercially-available kits employing Fluorescence Resonance Energy Transfer (FRET) technology (e.g., LANCE Ultra cAMP TR-FRET (PerkinElmer) and IP-One HTRF (Cisbio) kits). Briefly, CHO-K1 or HEK293 cells expressing serotonergic receptors are incubated with test compounds in stimulation buffer. After equilibration, the reaction is terminated with the donor and acceptor fluorescent conjugates in lysis buffer, and FRET is measured. Data are fit to non-linear curves to calculate potencies (e.g., EC$_{50}$) and efficacies (e.g., E$_{MAX}$), relative to positive controls (e.g., serotonin).

In Vitro Liver Metabolism and Kinetic Deuterium Isotope Effects Compounds (10 μl of 2 μM solution) are incubated in 200 μl of medium that contains 100 mg rat liver microsomes, NADPH regenerating system (1 mM NADP, 1 unit/ml of isocitrate dehydrogenase, 5 mM isocitric acid, 5 mM magnesium chloride), and 25 mM of phosphate buffer (pH 7.4). The reaction is terminated at different time points (0 to 60 min) by the addition of 300 μl of acetonitrile. For the analyses of products, the precipitated salts and proteins are spun out on a centrifuge, the residual solution diluted with 300 μl of water and injected into the LC/MS (Agilent 1200 system interfaced with an ABS Sciex 4000 QTRAP LC/MS/MS Mass Spectrometer). The metabolic stability may be estimated by evaluating the rate of disappearance of the main parent peak.

Comparison Between Reference Compound 2 (2C—B) and Compound II-14

Following the above protocol, Compound II-14 was found to have 50% longer have life than Reference Compound 2 (2C—B).

PK Studies in Rats and Mice

Pharmacokinetics of the deuterated phenethylamines is studied in rats. In a typical experiment, run as a cassette dosing, two groups of 5 Wistar female rats (200-250 g) with surgically inserted jugular vein catheter (Charles River, Andover, MA) are fasted for 12 h and then administered 5 mg/kg of the deuterated and 5 mg/kg of the related non-deuterated analog, by oral gavage or via a catheter for each group. At time points 0, 15, 30, 60 min, and 2, 4, 8, and 24 h, the resulting plasma is analyzed for the parent molecule using LC/MS spectroscopy. Two separate groups of 5 animals are used for determining blood-to-plasma ratio (BPR). Each group is sacrificed at time points 15 and 30 mi, respectively, and the concentration of the parent drug is determined in the brain and plasma by LC/MS spectroscopy.

Head-Twitch Response (HTR)

The HTR assay was performed in adult, male C57Bl/6J mice, procured from the Jackson Laboratory (Bar Harbor, Maine), as previously described (Canal, C. E., and Morgan, D., 2012, Head-twitch response in rodents induced by the hallucinogen 2,5-dimethoxy-4-iodoamphetamine: a comprehensive history, a re-evaluation of mechanisms, and its utility as a model, *Drug Test Anal* 4, 556-576; Saraf, T. S., Felsing, D. E., Armstrong, J. L., Booth, R. G., and Canal, C. E., 2021, Evaluation of lorcaserin as an anticonvulsant in juvenile Fmr1 knockout mice, *Epilepsy Res* 175, 106677). Mice were housed in standard laboratory cages with ad libitum access to food and water, and were acclimated to the vivarium for at least one week prior to testing in a procedure room. On the day of testing, mice were acclimated to the procedure room in their home cages for ≥60 mi before administration of test compounds. Mice were injected subcutaneously, placed immediately thereafter in a clear, polycarbonate box (46×20×20 cm), and HTRs were counted for 15 consecutive minutes, using hand-held tally counters, by two trained observers who were blind to treatment.

Figure 16:
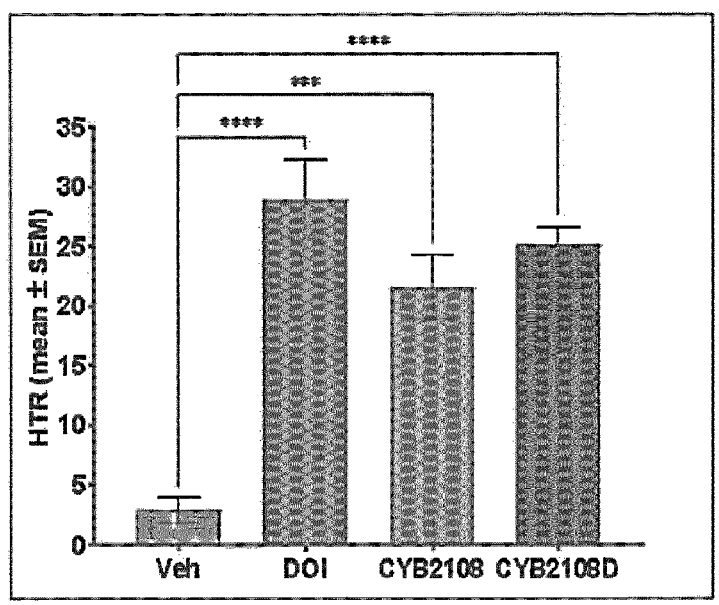
FIG. 16 shows the effects of CYB2108 (Compound I-1, 3 mg/kg) and CYB2108D (Compound II-10, 3 mg/kg) compared to vehicle (Veh) and the positive control, serotonergic psychedelic, (±)2,5-dimethoxy-4-iodoamphetamine (DOI, 1 mg/kg) on the serotonin 5-$HT_{2A}$ receptor-dependent head-twitch response (HTR) in adult, male C57Bl/6J mice-data for each test compound fit best to a two-site model (Graph-Pad Prism 9)

It was found that Compounds I-1 and II-10 elicited a HTR that was statistically different from vehicle, and that was not statistically different from DOI, a positive control (FIG. 16). In addition, the deuteration of the 2,5-methoxy groups increased the HTR response, presumably via improved metabolic stability of the deuterated compounds. These data confirm in vivo engagement and activation of serotonin 5-HT$_{2A}$ receptors by both non-deuterated (Compound I-1) and deuterated (Compound II-10) analogs.

Radioligand Competition Binding

Radioligand competition binding was performed as previously described (Saraf, T. S., Felsing, D. E., Armstrong, J. L., Booth, R. G., and Canal, C. E., 2021, Evaluation of lorcaserin as an anticonvulsant in juvenile Fmr1 knockout mice, *Epilepsy Res* 175, 106677), with minor modifications. Plasmids encoding human serotonin 5-HT$_{2A}$ receptor cDNA were procured from the cDNA Resource Center. Human embryonic kidney cells (HEK293, ATCC CRL-1573) were grown in a cell incubator in 100 mm dishes with antibiotic-free Dulbecco's modified Eagle's medium containing 10% fetal bovine serum. Cells were transfected at ~85% confluency with 5 15 μg cDNA using TransIT-2020 reagent (Mirus Bio, Madison, Wisconsin). After approximately 48 hours, cell membrane was collected via centrifugation. For all experiments, serotonin (5-HT) hydrochloride was used as a positive control, and mianserin hydrochloride (10 μM) was used to define non-specific binding. Each cell membrane homogenate expressing 5-HT$_{2A}$ receptors was incubated in 96-well plates with [$^3$H]Ketanserin (PerkinElmer, Waltham, Massachusetts), ~1.6 nM (its K$_d$ at human 5-HT$_{2A}$ receptors), in the absence or presence of test compounds in a buffer. Following equilibration, each sample was filtered rapidly under vacuum through fiberglass filters presoaked in a buffer and rinsed several times with an ice-cold buffer using a cell harvester. Filters were soaked with scintillation fluid, and counts per minute were detected using photodetectors. IC$_{50}$ values were computed using nonlinear, least squares regression analyses and then converted to K$_i$ values using the Cheng-Prusoff equation (GraphPad Prism 9.0, San Diego, California).

Figure 17:
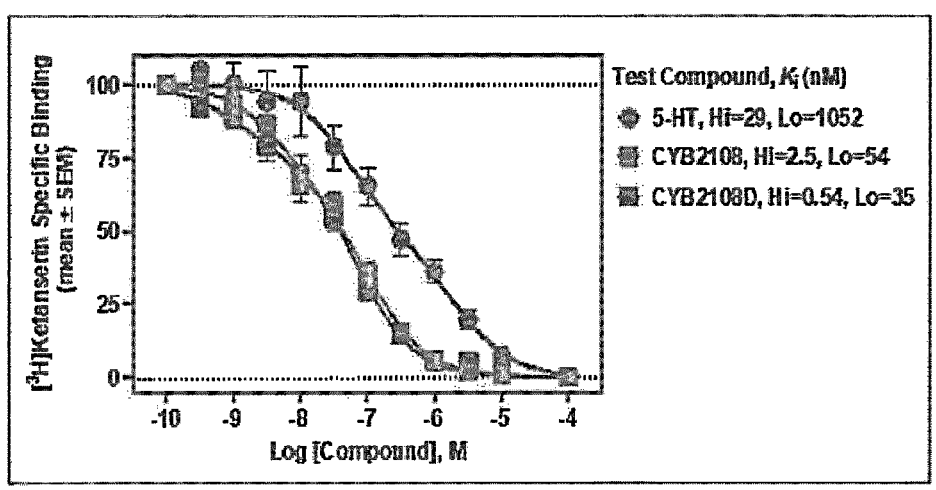
FIG. 17 is a graph of antagonist-labeled human serotonin 5-$HT_{2A}$ receptor radioligand competition binding using CYB2108 (Compound I-1) and CYB2108D (Compound II-10).

It was found that both Compounds I-1 and II-10 are pronounced agonists of serotonin 5-HT$_{2A}$ receptors (FIG. 17). There were no significant differences in affinity between deuterated and non-deuterated compounds, suggesting deuteration does not alter pharmacodynamics.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

Accordingly, the preceding merely illustrates the principles of the methods and compositions. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the following.

The invention claimed is:

1. A compound having a structure of formula (I):

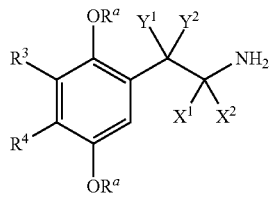

(I)

or a pharmaceutically acceptable salt, solvate, or stereoisomer thereof,
wherein:
$X^1$ and $X^2$ are independently hydrogen or deuterium;
$Y^1$ and $Y^2$ are independently hydrogen or deuterium;
$R^3$ is hydrogen or deuterium,
$R^4$ is —$SCF_3$; and
each $R^a$ is independently a substituted or unsubstituted $C_1$-$C_6$ alkyl,
wherein any position in the compound indicated as having deuterium has a minimum deuterium incorporation of at least 10 atom % at the site of deuteration.

2. The compound of claim 1, wherein $Y^1$ and $Y^2$ are hydrogen.

3. The compound of claim 1, wherein $R^3$ is hydrogen.

4. The compound of claim 1, wherein $X^1$ and $X^2$ are hydrogen.

5. The compound of claim 1, wherein $X^1$ and $X^2$ are deuterium.

6. The compound of claim 1, wherein each $R^a$ is —$CH_3$ or —$CD_3$.

7. The compound of claim 1, having a structure of formula (II):

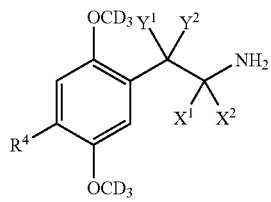

(II)

or a pharmaceutically acceptable salt, solvate, or stereoisomer thereof,
wherein:
$X^1$ and $X^2$ are independently hydrogen or deuterium;
$Y^1$ and $Y^2$ are independently hydrogen or deuterium; and
$R^4$ is —$SCF_3$.

8. The compound of claim 7, wherein $X^1$ and $X^2$ are hydrogen.

9. The compound of claim 1, having a structure of formula (IV):

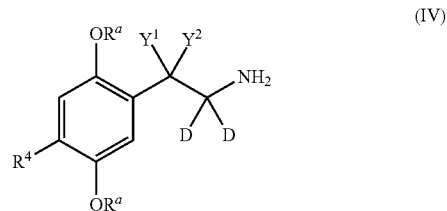

(IV)

or a pharmaceutically acceptable salt, solvate, or stereoisomer thereof,
wherein:
$Y^1$ and $Y^2$ are independently hydrogen or deuterium;
$R^4$ is —$SCF_3$; and
each $R^a$ is independently a substituted or unsubstituted $C_1$-$C_6$ alkyl.

10. The compound of claim 1, which is selected from the group consisting of

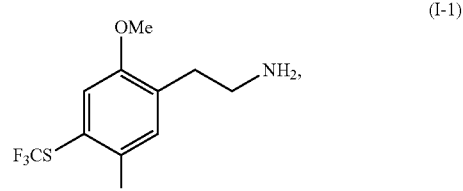

(I-1)

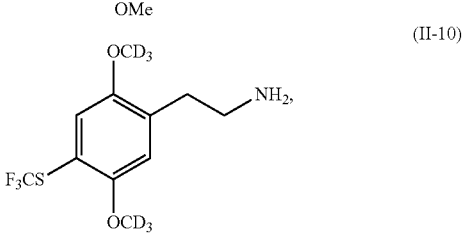

(II-10)

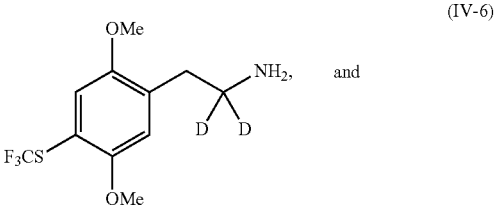

(IV-6)

and

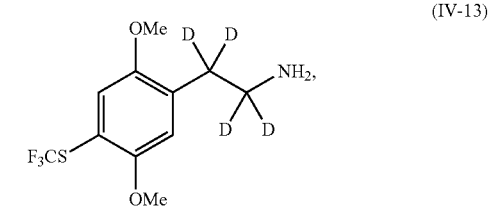

(IV-13)

or a pharmaceutically acceptable salt or solvate thereof.

11. A pharmaceutical composition, comprising the compound of claim 1 and a pharmaceutically acceptable excipient.

12. The pharmaceutical composition of claim 11, which is formulated for oral administration.

13. The pharmaceutical composition of claim 11, which is formulated for administration via inhalation.

* * * * *